United States Patent
Elkouby et al.

(10) Patent No.: US 11,464,872 B2
(45) Date of Patent: Oct. 11, 2022

(54) LENTIVIRAL VECTORS FOR THERAPEUTIC EXPRESSION OF BTK IN HAEMATOPOIETIC CELLS

(71) Applicant: NOGA THERAPEUTICS LTD., Ness-Ziona (IL)

(72) Inventors: Liron Elkouby, Modiin (IL); Noam Diamant, Ein-Vered (IL); Liat Shachnai-Pinkas, Kiryat Ono (IL)

(73) Assignee: NOGA THERAPEUTICS LTD., Ness-Ziona (IL)

( * ) Notice: Subject to any disclaimer, the term of this patent is extended or adjusted under 35 U.S.C. 154(b) by 0 days.

(21) Appl. No.: 17/492,637

(22) Filed: Oct. 3, 2021

(65) Prior Publication Data
US 2022/0175963 A1     Jun. 9, 2022

Related U.S. Application Data

(60) Provisional application No. 63/122,017, filed on Dec. 7, 2020, provisional application No. 63/147,956, filed on Feb. 10, 2021.

(51) Int. Cl.
| | |
|---|---|
| C07H 21/04 | (2006.01) |
| C12N 15/63 | (2006.01) |
| A61K 48/00 | (2006.01) |
| C12N 9/12 | (2006.01) |
| A61P 37/04 | (2006.01) |
| C12N 15/86 | (2006.01) |
| A01K 67/00 | (2006.01) |

(52) U.S. Cl.
CPC ............ *A61K 48/005* (2013.01); *A61P 37/04* (2018.01); *C12N 9/12* (2013.01); *C12N 15/86* (2013.01); *C12N 2740/15043* (2013.01)

(58) Field of Classification Search
CPC .................. A61K 48/005; C12N 15/86; C12N 2740/15043
See application file for complete search history.

(56) References Cited

U.S. PATENT DOCUMENTS

| | | | | |
|---|---|---|---|---|
| 9,587,003 | B2 * | 3/2017 | Bancel | .................... C07K 14/56 |
| 2007/0161031 | A1 * | 7/2007 | Trinklein | ............ C12N 15/1086 |
| | | | | 435/325 |

FOREIGN PATENT DOCUMENTS

| | | |
|---|---|---|
| WO | 2005040383 A1 | 5/2005 |
| WO | 2018195297 A1 | 10/2018 |

OTHER PUBLICATIONS

Rohrer, J. et al., "Transcriptional Regulatory Elements Within the First Intron of Bruton's Tyrosine Kinase" Blood, vol. 91, No. 1: pp. 214-221, 1998. Retrieved Nov. 30, 2021; https://doi.org/10.1182/blood.V91.1.214.

Muller, S. et al., "Synergistic Activation of the Human Btk Promoter by Transcription Factors Sp1/3 and PU.1" Biochemical and Biophysical Research Communications 259, 364-369 (1999). Retrieved Nov. 30, 2021; DOI: 10.1006/bbrc.1999.0677.

Muller-Kuller, U. et al., "A minimal ubiquitous chromatin opening element (UCOE) effectively prevents silencing of iuxtaposed heterologous promoters by epigenetic remodeling in multipotent and pluripotent stem cells" Nucleic Acids Research, vol. 43, No. 3, 1577-1592, 2015. Retrieved Nov. 30, 2021; doi: 10.1093/nar/gkv019.

Sather, B.D., et al., "Development of B-lineage Predominant Lentiviral Vectors for Use in Genetic Therapies for B Cell Disorders" The American Society of Gene & Cell Therapy, vol. 19 No. 3, 515-525, 2011. Retrieved Nov. 30, 2021 from: https://pubmed.ncbi.nlm.nih.gov/21139568/; DOI: 10.1038/mt.2010.259.

Moreau, T. et al., "Development of an enhanced B-specific lentiviral vector expressing BTK: a tool for gene therapy of XLA" Gene Therapy, 15, 942-952, 2008. Retrieved Nov. 30, 2021; https://doi.org/10.1038/gt.2008.17.

Ng, YY et al., "Correction of B-cell development in Btk-deficient mice using lentiviral vectors with codon-optimized human BTK" Leukemia, 24, 1617-1630, 2010. Retrieved Nov. 30, 2021; DOI: 10.1038/leu.2010.140.

Kil, Laurens P. et al., "Btk levels set the threshold for B-cell activation and negative selection of autoreactive B cells in mice" Blood, vol. 119, No. 16, 3744-3756, 2012. Retrieved Nov. 30, 2021; DOI 10.1182/blood-2011-12-397919.

Wang, Y. et al., "Progressive engineering of a homing endonuclease genome editing reagent for the murine X-linked immunodeficiency locus" Nucleic Acids Research, vol. 42, No. 10, 6463-6475, 2014. Retrieved Nov. 30, 2021; doi: 10.1093/nar/gku224.

Yamamoto, H. et al., "BTK gene targeting by homologous recombination using a helper-dependent adenovirus/adeno-associated virus hybrid vector" Gene Therapy, 23, 205-213, 2016. Retrieved Nov. 30, 2021; doi:10.1038/gt.2015.91.

Hendriks, R.W. et al., "Biology and novel treatment options for XLA, the most common monogenetic immunodeficiency in man" Informa Healthcare, Expert Opin. Ther. Targets, 15(8), 1003-1021, 2011. Retrieved Nov. 30, 2021; doi: 10.1517/14728222.2011.585971.

(Continued)

*Primary Examiner* — Quang Nguyen
(74) *Attorney, Agent, or Firm* — The Roy Gross Law Firm, LLC; Roy Gross

(57) ABSTRACT

The present application, in some embodiments, is directed to a polynucleotide including: (a) a first nucleic acid molecule including a sequence of a human endogenous Bruton's tyrosine kinase (BTK) promoter; and (b) a second nucleic acid molecule including a codon optimized sequence encoding a BTK or a functional analog thereof. Further provided are an expression vector, a cell, and a composition, all of which include the polynucleotide of the invention, and a method of using same, such as for treating X-linked Agammaglobulinemia (XLA) in a subject in need thereof.

7 Claims, 5 Drawing Sheets

Specification includes a Sequence Listing.

(56) References Cited

OTHER PUBLICATIONS

Kerns, H.M. et al., "B cell-specific lentiviral gene therapy leads to sustained B-cell functional recovery in a murine model of X-linked agammaglobulinemia" Blood, vol. 115, No. 11, 2146-2155, 2010. Retrieved Nov. 30, 2021; DOI 10.1182/blood-2009-09-241869.

Shillitoe, Benjamin M.J. et al., "An update on X-Linked agammaglobulinaemia: clinical manifestations and management" Curr Opin Allergy Clin Immunol, vol. 19, No. 00, pp. 1-7, 2019. Retrieved Nov. 30, 2021; doi: 10.1097/ACI.0000000000000584.

Rudina, Shireen S. et al., "A Novel Chromatin-Opening Element for Stable Long-term Transgene Expression" bioRxiv preprint first posted online, 23 pages, May 3, 2019. doi: http://dx.doi.org/10.1101/626713.

Singh, Swati, et al. "238. BTK-Promoter LV Vectors Utilizing Conserved Intron Element Mediate Functional Rescue in Murine XLA." Molecular Therapy vol. 23, Supplement 1, (2015): S93. Retrieved from: https://www.cell.com/molecular-therapy-family/molecular-therapy/pdf/S1525-0016(16)33843-6.pdf.

Kerns, H. et al., "Lentiviral Vectors Using a Ubiquitously Acting Chromatin Opening Element and Endogenous Btk Promoter Restore B and Myeloid Cell Defects in Murine X-Linked : Agammaglobulinemia", Molecular Therapy, (2011), vol. 19, No. 1, p. S136. Retrieved from: https://www.cell.com/molecular-therapy-family/molecular-therapy/pdf/S1525-0016(16)36921-0.pdf.

\* cited by examiner

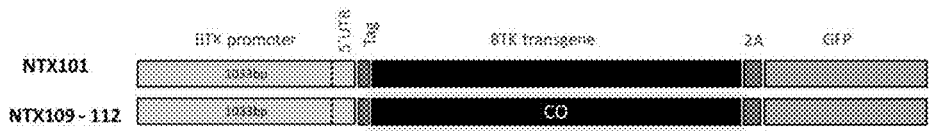
Figure 1A
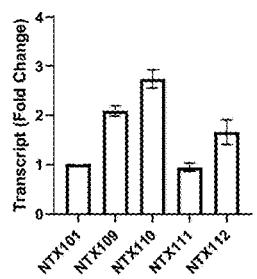 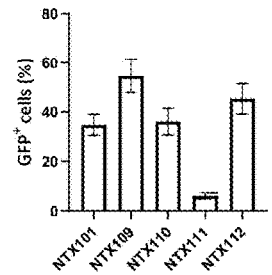 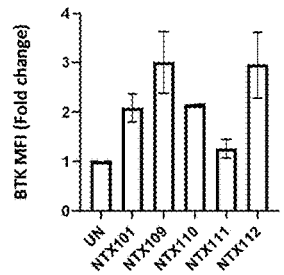
Figure 1B  Figure 1C  Figure 1D
Figure 2A
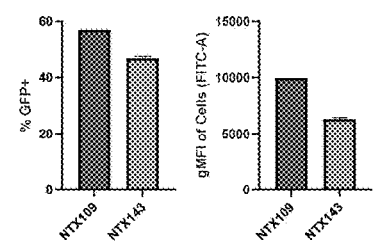
Figure 2C
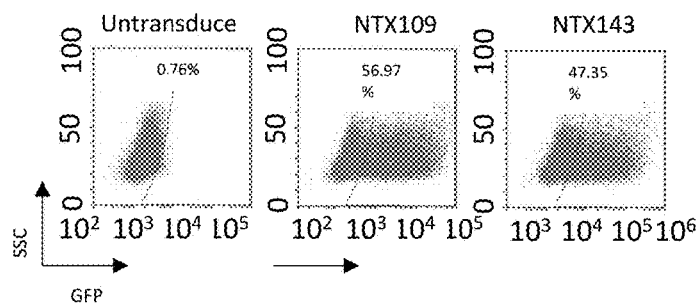
Figure 2B
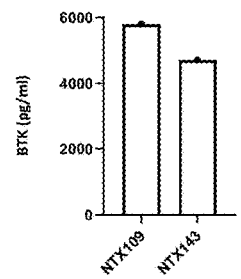
Figure 2D

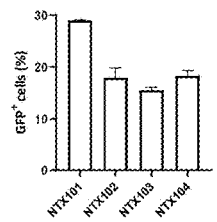
Figure 3A
Figure 3C
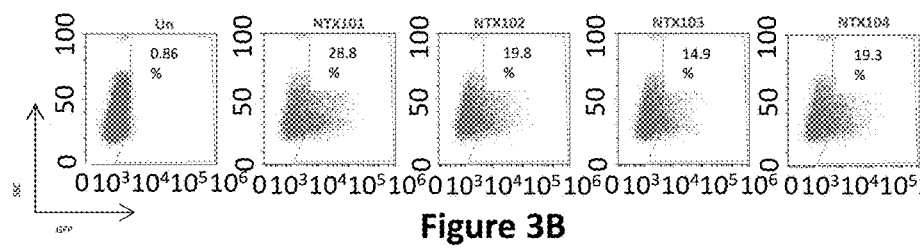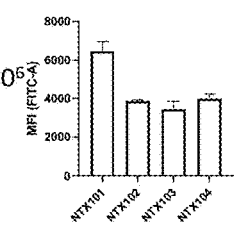
Figure 3B
Figure 3D
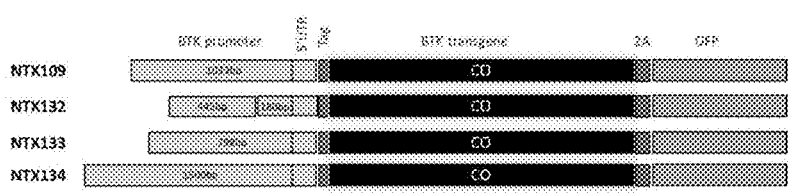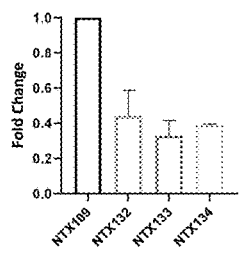
Figure 4A
Figure 4C
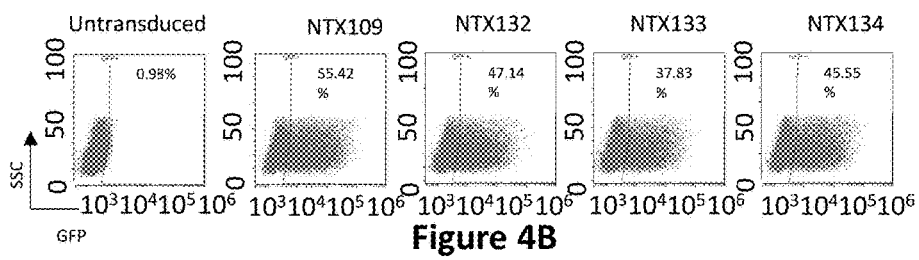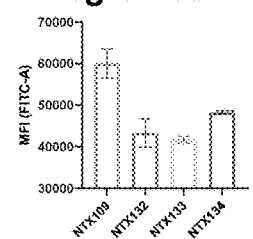
Figure 4B
Figure 4D

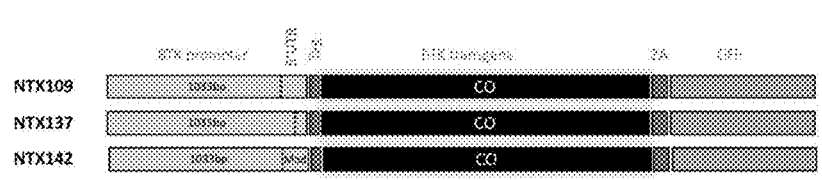
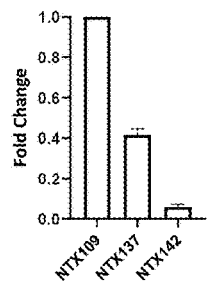
Figure 5A
Figure 5C
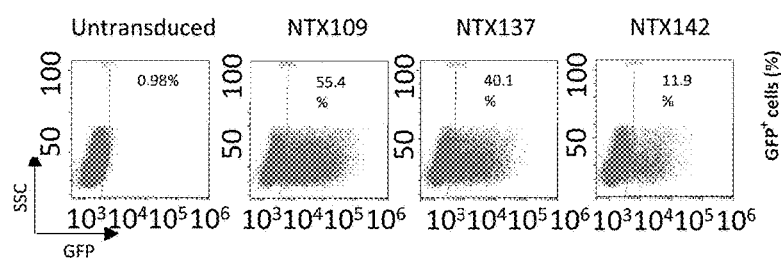
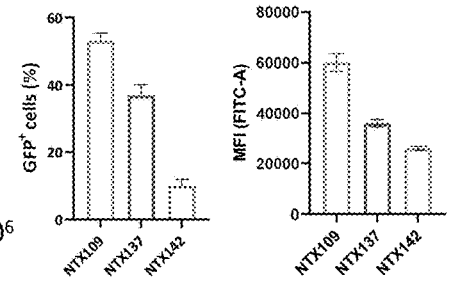
Figure 5B     Figure 5D     Figure 5E
Figure 6A
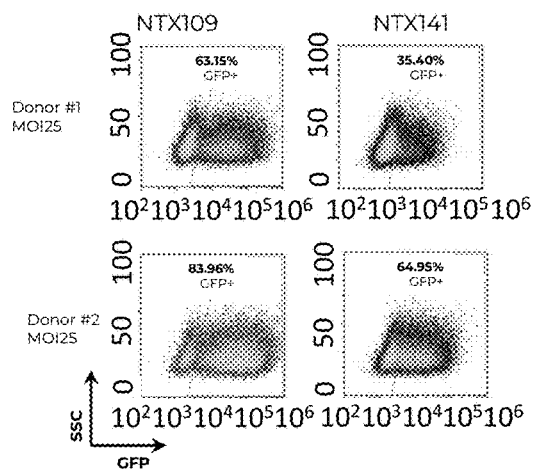
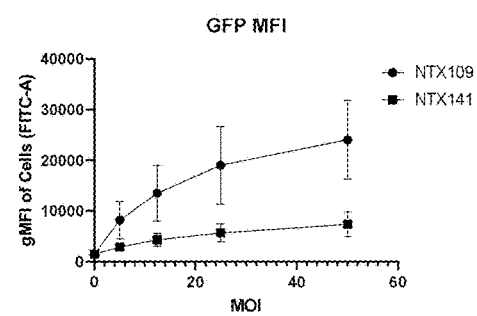
Figure 6C
Figure 6B

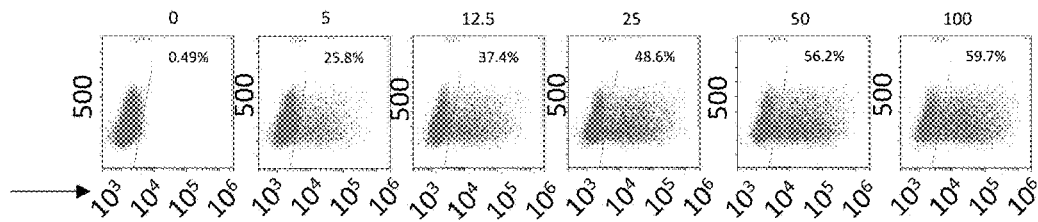
Figure 7A
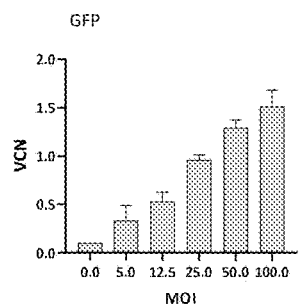
Figure 7B
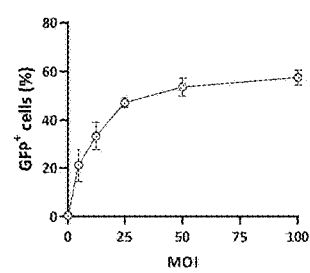
Figure 7C
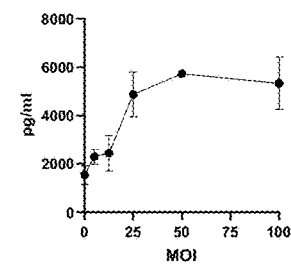
Figure 7D
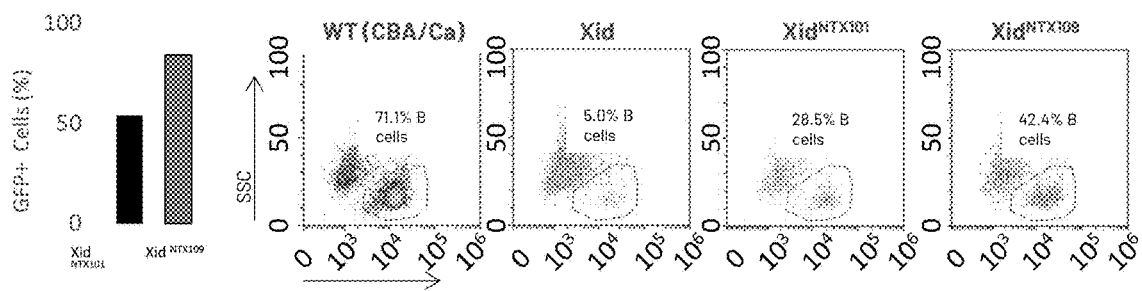
Figure 8A
Figure 8C
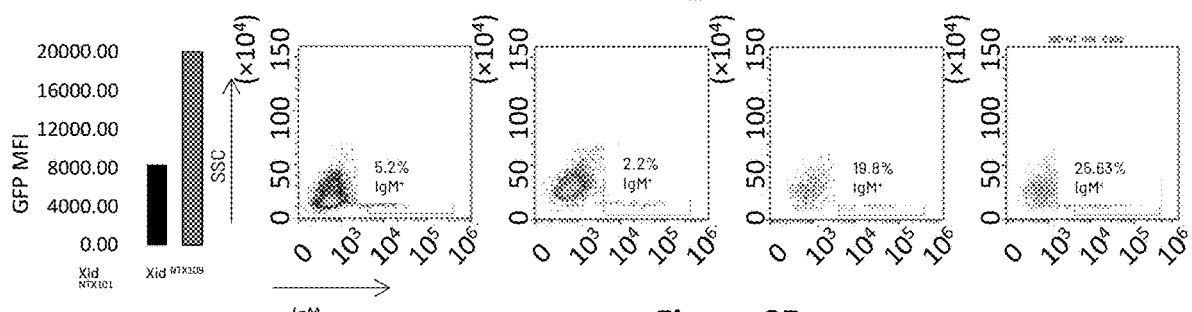
Figure 8B
Figure 8D

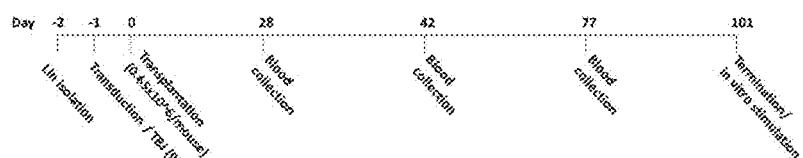
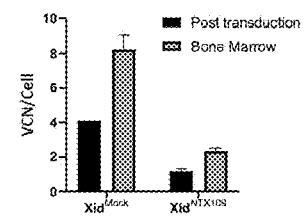
Figure 9A  Figure 9B
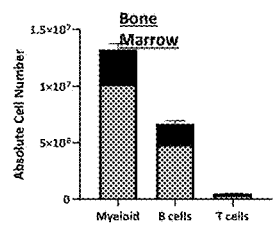 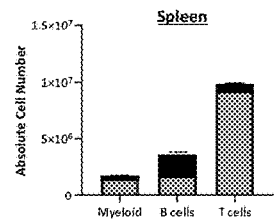 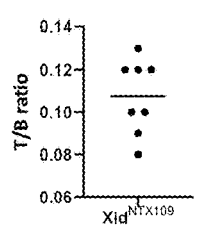
Figure 9C  Figure 9D  Figure 9E
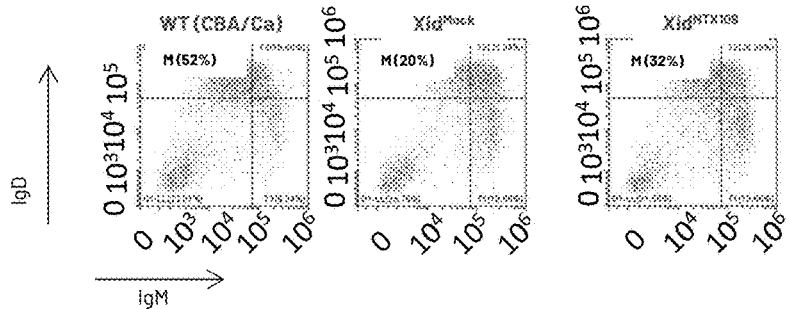 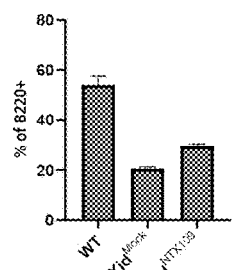
Figure 9F  Figure 9G
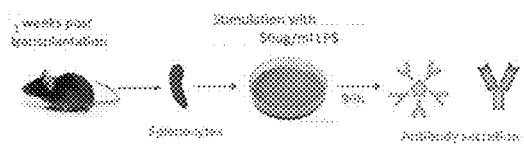
Figure 10A
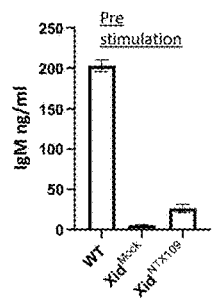 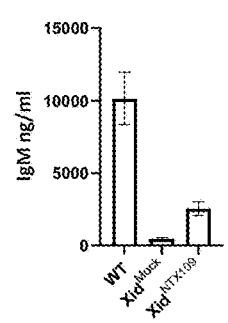 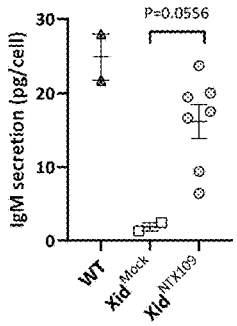
Figure 10B  Figure 10C  Figure 10D

SEQUENCE LISTING

```
<160> NUMBER OF SEQ ID NOS: 46

<210> SEQ ID NO 1
<211> LENGTH: 180
<212> TYPE: DNA
<213> ORGANISM: Artificial Sequence
<220> FEATURE:
<223> OTHER INFORMATION: Synthetic

<400> SEQUENCE: 1
gactcaagat agtagtgtca gaggtcccaa gcaaatgaag ggcggggaca gttgaggggg      60
tggaataggg acggcagcag ggaaccagat agcatgctgc tgagaagaaa aaaagacatt     120
ggtttaggtc aggaagcaaa aaaagggaac tgagtggctg tgaaagggtg gggtttgctc     180

<210> SEQ ID NO 2
<211> LENGTH: 398
<212> TYPE: DNA
<213> ORGANISM: Artificial Sequence
<220> FEATURE:
<223> OTHER INFORMATION: Synthetic

<400> SEQUENCE: 2
gctcttcctg gccagtctct ttgctctgtg tctgccagcc cccagcatct ctcctctttc      60
ctgtaagccc ctctccctgt gctgactgtc ttcatagtac tttaggtatg ttgtcccttt     120
```

```
acctctggga ggatagcttg atgacctgtc tgctcaggcc agccccatct agagtctcag    180
tggccccagt catgttgaga aggttctttt caaagataga ctcaagatag tagtgtcaga    240
ggtcccaagc aaatgaaggg cggggacagt tgaggggtg aatagggac ggcagcaggg     300 aaccagatag catgctgctg agaagaaaaa aagacattgg tttaggtcag gaagcaaaaa   360
aagggaactg agtggctgtg aaagggtggg gtttgctc                           398
```

<210> SEQ ID NO 3
<211> LENGTH: 588
<212> TYPE: DNA
<213> ORGANISM: Artificial Sequence
<220> FEATURE:
<223> OTHER INFORMATION: Synthetic

<400> SEQUENCE: 3

```
gtatttctgt gggcttatat tccgacattt ttatctgtag gggaaaaatg ctttcttaga    60
aaatgactca gcacggggaa gtcttgtctc tacctctgtc ttgttttgtc ctttggggtc   120
ccttcactat caagttcaac tgtgtgtccc tgagactcct ctgccccgga ggacaggaga   180
ctcgaaaaac gctcttcctg ccagtctct ttgctctgtg tctgccagcc ccagcatct    240 ctcctctttc ctgtaagccc ctctccctgt gctgactgtc ttcatagtac tttaggtatg   300
ttgtcccttt acctctggga ggatagcttg atgacctgtc tgctcaggcc agccccatct   360
agagtctcag tggccccagt catgttgaga aggttctttt caaagataga ctcaagatag   420
tagtgtcaga ggtcccaagc aaatgaaggg cggggacagt tgaggggtg aatagggac    480 ggcagcaggg aaccagatag catgctgctg agaagaaaaa aagacattgg tttaggtcag   540
gaagcaaaaa aagggaactg agtggctgtg aaagggtggg gtttgctc                588
```

<210> SEQ ID NO 4
<211> LENGTH: 1033
<212> TYPE: DNA
<213> ORGANISM: Artificial Sequence
<220> FEATURE:
<223> OTHER INFORMATION: Synthetic

<400> SEQUENCE: 4

```
acccccatttt ttttgtttgc ttgtttgttt gttttttaga caaaataaag aaaaaaaaat    60
aaggtcctgt tgacttaaaa cttcggatga aattgtagtg ggacctgtga tctgtttcta   120
cattaggata cagtgccttg gggcaaggaa atatggcagt gcccgaggtg tcaaggtggg   180
caggcagatc agtcagcagg ggctccacca tcatggtctg cattcaatac tggctgcatt   240
tcctaggaga atccctgggg gaatcattgc agttggagca taatgtaggg ggcccctgag   300
aaaacctcca ggcttcaagt gacataccta gtctgcttta ccggtttaca ggactcaaga   360
gaaaggtgga cattgagagt taatccctga ggccaaatct taaatggaga aagtcaacat   420
ccacagaaaa tggggaaggg cacaagtatt tctgtgggct tatattccga cattttatc     480 tgtaggggaa aaatgctttc ttagaaaatg actcagcacg gggaagtctt gtctctacct   540
ctgtcttgtt ttgtcctttg gggtcccttc actatcaagt tcaactgtgt gtccctgaga   600
ctcctctgcc ccggaggaca ggagactcga aaaacgctct tcctggccag tctctttgct   660
ctgtgtctgc cagcccccag catctctcct cttcctgta agcccctctc cctgtgctga   720
ctgtcttcat agtactttag gtatgttgtc cctttacctc tgggaggata gcttgatgac   780
ctgtctgctc aggccagccc catctagagt ctcagtggcc ccagtcatgt tgagaaaggt   840
```

```
tctttcaaag atagactcaa gatagtagtg tcagaggtcc caagcaaatg aagggcgggg    900
acagttgagg gggtggaata gggacggcag cagggaacca gatagcatgc tgctgagaag    960
aaaaaaagac attggtttag gtcaggaagc aaaaaaaggg aactgagtgg ctgtgaaagg   1020
gtggggtttg ctc                                                      1033

<210> SEQ ID NO 5
<211> LENGTH: 592
<212> TYPE: DNA
<213> ORGANISM: Artificial Sequence
<220> FEATURE:
<223> OTHER INFORMATION: Synthetic

<400> SEQUENCE: 5
accccatttt ttttgtttgc ttgtttgttt gttttttaga caaaataaag aaaaaaaaat     60
aaggtcctgt tgacttaaaa cttcggatga aattgtagtg ggacctgtga tctgtttcta    120
cattaggata cagtgccttg ggcaaggaa atatggcagt gcccgaggtg tcaaggtggg    180
caggcagatc agtcagcagg ggctccacca tcatggtctg cattcaatac tggctgcatt   240
tcctaggaga atccctgggg gaatcattgc agttggagca taatgtaggg ggcccctgag    300
aaaacctcca ggcttcaagt gacatacctac gtctgcttta ccggtttaca ggactcaaga   360
gaaaggtgga cattgagagt taatccctga ggccaaatct taaatggaga aagtcaacat    420
ccacagaaaa tggggaaggg cacaagactc aagatagtag tgtcagaggt cccaagcaaa    480
tgaagggcgg ggacagttga gggggtggaa tagggacggc agcagggaac cagatagcat    540
gctgctgaga agaaaaaaag acattggttt aggtcaggaa gcaaaaaaag gg            592

<210> SEQ ID NO 6
<211> LENGTH: 798
<212> TYPE: DNA
<213> ORGANISM: Artificial Sequence
<220> FEATURE:
<223> OTHER INFORMATION: Synthetic

<400> SEQUENCE: 6
gcatttccta ggagaatccc tgggggaatc attgcagttg gagcataatg tagggggccc     60
ctgagaaaac ctccaggctt caagtgacat acctagtctg ctttaccggt ttacaggact    120
caagagaaag gtggacattg agagttaatc cctgaggcca atcttaaat ggagaaagtc    180 aacatccaca gaaaatgggg aagggcacaa gtatttctgt gggcttatat tccgacattt    240
ttatctgtag gggaaaaatg ctttcttaga aaatgactca gcacggggaa gtcttgtctc    300
tacctctgtc ttgttttgtc ctttggggtc ccttcactat caagttcaac tgtgtgtccc    360
tgagactcct ctgccccgga ggacaggaga ctcgaaaaac gctcttcctg gccagtctct    420
ttgctctgtg tctgccagcc cccagcatct ctcctctttc ctgtaagccc ctctccctgt    480
gctgactgtc ttcatagtac tttaggtatg ttgtcccttt acctctggga ggatagcttg    540
atgacctgtc tgctcaggcc agccccatct agagtctcag tggccccagt catgttgaga    600
aaggttcttt caaagataga ctcaagatag tagtgtcaga ggtcccaagc aaatgaaggg    660
cggggacagt tgagggggtg gaatagggac ggcagcaggg aaccagatag catgctgctg    720
agaagaaaaa aagacattgg tttaggtcag gaagcaaaaa aagggaactg agtggctgtg    780
aaagggtggg gtttgctc                                                  798

<210> SEQ ID NO 7
<211> LENGTH: 1533
```

<212> TYPE: DNA
<213> ORGANISM: Artificial Sequence
<220> FEATURE:
<223> OTHER INFORMATION: Synthetic

<400> SEQUENCE: 7

```
caaatgtgag tatcaaccac tctatcatca gtctacaaat actttaaatg tttttattta      60
aagtcctgtt gatggctggg agaggtggct cactcctgta atccctgcat tttgggaggc     120
caaggcagga gtatcgcttg agcccaggag tttgagacca gcctgggcaa catagtgaaa     180
ccccatctct acaaaaagta gaaaaattag cccagcacag tgatgtgtgc ctatagtccc     240
aggtactagg gtgactgagg tgagaggatc acttgagccc aggaggtgga ggctgcagtg     300
agccatgatc acgccactgc actccaacct gggcttcaga gcaagaccct gtctcaaaaa     360
aaaaaaaaaa aaaaaaaggt cccagggcct gttggggctt gggggtgagg ggagggatct     420
tagaggatgg gtcaataggt gcagcaaatc accatgtcac acatatacct atgtaacaaa     480
cttgcacctt ctgcacatat accccatttt ttttgtttgc ttgtttgttt gtttttaga     540
caaaataaag aaaaaaaaat aaggtcctgt tgacttaaaa cttcggatga aattgtagtg     600
ggacctgtga tctgtttcta cattaggata cagtgccttg gggcaaggaa atatggcagt     660
gcccgaggtg tcaaggtggg caggcagatc agtcagcagg ggctccacca tcatggtctg     720
cattcaatac tggctgcatt tcctaggaga atccctgggg gaatcattgc agttggagca     780
taatgtaggg ggcccctgag aaaacctcca ggcttcaagt gacatacctc gtctgcttta     840
ccggtttaca ggactcaaga gaaaggtgga cattgagagt taatccctga ggccaaatct     900
taaatggaga agtcaacat ccacagaaaa tggggaaggg cacaagtatt tctgtgggct     960
tatattccga cattttatc tgtaggggaa aaatgctttc ttagaaaatg actcagcacg    1020
gggaagtctt gtctctacct ctgtcttgtt ttgtcctttg gggtcccttc actatcaagt    1080
tcaactgtgt gtccctgaga ctcctctgcc ccggaggaca ggagactcga aaacgctct    1140
tcctggccag tctctttgct ctgtgtctgc cagcccccag catctctcct ctttcctgta    1200
agcccctctc cctgtgctga ctgtcttcat agtactttag gtatgttgtc cctttacctc    1260
tgggaggata gcttgatgac ctgtctgctc aggccagccc catctagagt ctcagtggcc    1320
ccagtcatgt tgagaaaggt tctttcaaag atagactcaa gatagtagtg tcagaggtcc    1380
caagcaaatg aagggcgggg acagttgagg gggtggaata gggacggcag cagggaacca    1440
gatagcatgc tgctgagaag aaaaaaagac attggtttag gtcaggaagc aaaaaagggg    1500
aactgagtgg ctgtgaaagg gtggggttg ctc                                  1533
```

<210> SEQ ID NO 8
<211> LENGTH: 1980
<212> TYPE: DNA
<213> ORGANISM: Artificial Sequence
<220> FEATURE:
<223> OTHER INFORMATION: Synthetic

<400> SEQUENCE: 8

```
atggccgcag tgattctgga gagcatcttt ctgaagcgat cccaacagaa aaagaaaaca      60
tcacctctaa acttcaagaa gcgcctgttt ctcttgaccg tgcacaaact ctcctactat    120
gagtatgact ttgaacgtgg gagaagaggc agtaagaagg gttcaataga tgttgagaag    180
atcacttgtg ttgaaacagt ggttcctgaa aaaaatcctc ctccagaaag acagattccg    240
agaagaggtg aagagtccag tgaaatggag caaatttcaa tcattgaaag gttcccttat    300
```

```
cccttccagg ttgtatatga tgaagggcct ctctacgtct tctccccaac tgaagaacta    360
aggaagcggt ggattcacca gctcaaaaac gtaatccggt acaacagtga tctggttcag    420
aaatatcacc cttgcttctg gatcgatggg cagtatctct gctgctctca gacagccaaa    480
aatgctatgg gctgccaaat tttggagaac aggaatggaa gcttaaaacc tgggagttct    540
caccggaaga caaaaaagcc tcttccccca acgcctgagg aggaccagat cttgaaaaag    600
ccactaccgc ctgagccagc agcagcacca gtctccacaa gtgagctgaa aaaggttgtg    660
gccctttatg attacatgcc aatgaatgca aatgatctac agctgcggaa gggtgatgaa    720
tattttatct tggaggaaag caacttacca tggtggagag cacgagataa aaatgggcag    780
gaaggctaca ttcctagtaa ctatgtcact gaagcagaag actccataga aatgtatgag    840
tggtattcca acacatgac tcggagtcag gctgagcaac tgctaaagca gaggggaaa     900 gaaggaggtt tcattgtcag agactccagc aaagctggca atatacagt gtctgtgttt     960 gctaaatcca caggggaccc tcaagggagt atacgtcatt atgttgtgtg ttccacacct   1020
cagagccagt attacctggc tgagaagcac ctttcagca ccatccctga gctcattaac   1080
taccatcagc acaactctgc aggactcata tccaggctca aatatccagt gtctcaacaa   1140
aacaagaatg caccttccac tgcaggcctg ggatacggat catgggaaat tgatccaaag   1200
gacctgacct tcttgaagga gctggggact ggacaatttg gggtagtgaa gtatgggaaa   1260
tggagaggcc agtacgacgt ggccatcaag atgatcaaag aaggctccat gtctgaagat   1320
gaattcattg aagaagccaa agtcatgatg aatctttccc atgagaagct ggtgcagttg   1380 tatgcgtct gcaccaagca gcgccccatc ttcatcatca ctgagtacat ggccaatggc   1440
tgcctcctga actacctgag ggagatgcgc caccgcttcc agactcagca gctgctagag   1500
atgtgcaagg atgtctgtga agccatggaa tacctggagt caaagcagtt ccttcaccga   1560
gacctggcag ctcgaaactg tttggtaaac gatcaaggag ttgttaaagt atctgatttc   1620
ggcctgtcca ggtatgtcct ggatgatgaa tacacaagct cagtaggctc caaatttcca   1680
gtccggtggt ccccaccgga agtcctgatg tatagcaagt tcagcagcaa atctgacatt   1740
tgggcttttg gggttttgat gtgggaaatt tactccctgg ggaagatgcc atatgagaga   1800
tttactaaca gtgagactgc tgaacacatt gcccaaggcc tacgtctcta caggcctcat   1860
ctggcttcag agaaggtata taccatcatg tacagttgct ggcatgagaa agcagatgag   1920
cgtcccactt tcaaaattct tctgagcaat attctagatg tcatggatga agaatcctga   1980
```

`<210>` SEQ ID NO 9
`<211>` LENGTH: 1980
`<212>` TYPE: DNA
`<213>` ORGANISM: Artificial Sequence
`<220>` FEATURE:
`<223>` OTHER INFORMATION: Synthetic

`<400>` SEQUENCE: 9

```
atggccgccg tcatcctaga gagcatcttc ctgaagagat ctcagcaaaa gaagaaaacc     60
tcccctctga acttcaagaa gcggctgttc ctgctgaccg tgcacaaact gagctactac    120
gagtacgatt cgagcggggg aagaagagga agcaagaagg gctctatcga cgtggaaaaa    180
atcacatgcg tggagaccgt ggtgcccgag aagaaccctc accagaacg gcagatcccc    240 agaagggggg aggaatctag cgagatggaa cagatcagca tcatcgagag gtttccttat    300 ccttccagg tggtttacga cgaaggtcct ctgtatgtgt tcagccccac agaagaactg    360
cggaagcgct ggatccacca gctgaagaac gtgatcgat acaacagcga cctggtgcag    420
```

| | |
|---|---|
| aaataccacc cctgcttctg gatcgacggc cagtacctct gctgcagcca aacagccaag | 480 |
| aatgctatgg gctgccagat cctggaaaac cgaaacggct ctctgaaacc tggcagcagc | 540 |
| catcggaaga ccaagaagcc cctgcctcct accccgaag aggaccaaat cctgaagaaa | 600 |
| cctctgccac ctgagccagc cgctgctcct gtgagcacct ccgagctgaa aaaggtggtc | 660 |
| gccctgtacg attacatgcc tatgaacgcc aacgacctcc agttgcgcaa gggcgacgag | 720 |
| tacttcattc tggaagagtc caacctgcct tggtggcggg ccagagataa gaacggccaa | 780 |
| gagggctata tccccagcaa ttacgtgacc gaggccgaag attcgatcga gatgtacgag | 840 |
| tggtacagca agcacatgac cagaagccag gccgagcagc tgctgaagca ggagggcaag | 900 |
| gaaggcggct tcatcgttag agattcttct aaagccggca agtacacagt gtccgtgttc | 960 |
| gccaagagca caggcgatcc ccagggagtc attcggcact acgtggtgtg tagtaccccct | 1020 |
| cagagccagt actacctggc tgagaagcac ctgttctcta caatccctga gctgatcaac | 1080 |
| taccaccagc acaacagcgc cggcctgatc agcagactga aatacccccgt gagccaacag | 1140 |
| aacaagaacg ccccctctac agccggcctg ggatatggaa gctgggagat cgaccccaag | 1200 |
| gacctgacct tcctgaagga actgggcacc ggccagtttg gagtggtcaa gtacggcaaa | 1260 |
| tggagaggcc agtacgatgt ggccatcaag atgatcaagg agggctctat gagcgaagat | 1320 |
| gagttcatag aggaagcgaa agtgatgatg aatctgtctc atgagaagct ggtgcagctg | 1380 |
| tacggcgtgt gtacaaaaca gagacctatc tttattatca ccgagtacat ggctaacggc | 1440 |
| tgtctgctga attacctgcg ggaaatgaga cacagattcc agacacagca actgctggag | 1500 |
| atgtgcaagg acgtgtgcga ggccatggaa tacctggaat ccaagcagtt cctgcaccgg | 1560 |
| gacctggccg ccagaaattg tctggtgaac gaccagggcg tggtcaaggt gtccgacttc | 1620 |
| ggcctgagca gatacgtgct ggacgacgaa tacaccagca gcgtgggcag caaattccct | 1680 |
| gtcagatgga gccctcctga agtgctgatg tacagcaagt tcagcagcaa gagcgacatc | 1740 |
| tgggcctttg gagtgctgat gtgggaaatc tactctctgg gcaagatgcc ttacgagaga | 1800 |
| ttcaccaaca gcgaaaccgc cgagcacatc gcccagggcc tgcggctgta tcggcctcac | 1860 |
| ctggccagcg agaaagtgta caccatcatg tatagctgct ggcacgagaa ggccgacgag | 1920 |
| agacctacct ttaagatcct gctgtccaac atcctggatg tgatggacga ggaatcctga | 1980 |

<210> SEQ ID NO 10
<211> LENGTH: 1980
<212> TYPE: DNA
<213> ORGANISM: Artificial Sequence
<220> FEATURE:
<223> OTHER INFORMATION: Synthetic

<400> SEQUENCE: 10

| | |
|---|---|
| atggccgctg tgattctgga gagcatcttc ctcaagaggt cccagcagaa gaagaagacc | 60 |
| agcccctca acttcaagaa gaggctgttc ctcctcaccg tccataagct gagctactac | 120 |
| gagtacgact tcgaaagggg aagaaggggc tccaaaaagg gctccatcga cgtggagaag | 180 |
| atcacatgcg tggaaaccgt ggtccccgaa aaaaatcccc cccccgaaag gcagatcccc | 240 |
| agaagggag aggagtccag cgaaatggag cagatctcca tcatcgaaag gttccccctac | 300 |
| cccttccaag tggtgtacga cgaaggccct ctgtacgtgt ctcccccac cgaagaactg | 360 |
| agaaagaggt ggatccacca gctgaagaac gtcattagat acaactccga cctcgtgcag | 420 |
| aaataccacc cttgcttctg gatcgacggc cagtatctgt gttgcagcca aacagccaag | 480 |

```
aacgctatgg gctgccagat tctggagaat agaaacggca gcctcaagcc cggcagcagc    540
cataggaaga ccaaaaagcc tctgcctccc accccccgagg aggatcagat tctgaagaag    600
```

```
aacgctatgg gctgccagat tctggagaat agaaacggca gcctcaagcc cggcagcagc    540
cataggaaga ccaaaaagcc tctgcctccc accccgagg aggatcagat tctgaagaag    600
cctctgcctc ccgagcccgc cgctgctccc gtgagcacat ccgagctgaa gaaggtggtc    660
gctctgtacg actacatgcc catgaacgcc aatgacctcc aactgagaaa gggagacgag    720
tactttattc tggaggagag caacctccct tggtggagag ctagggataa gaatggccaa    780
gagggataca tccccagcaa ctatgtgacc gaggccgagg acagcattga gatgtacgag    840
tggtacagca agcatatgac aagatcccaa gccgagcaac tgctgaagca gagggcaag    900
gagggcggct tcattgtgag agacagctcc aaggctggca atacaccgt gagcgtgttc    960
gccaagagca ccggcgatcc ccaaggcgtg atcagacatt acgtcgtgtg cagcaccct   1020
cagtcccagt actacctcgc cgagaaacac ctcttctcca caatcccga gctgattaac   1080
taccaccagc acaactccgc cggcctcatt tctagactga agtaccccgt cagccagcag   1140
aataagaatg ctccctccac agctggactg gctacggaa gctgggagat cgaccccaaa   1200
gatctgacct ttctgaaaga actgggcacc ggccaatttg gcgtggtgaa gtacggcaag   1260
tggaggggcc agtacgacgt ggctattaag atgatcaagg agggaagcat gtccgaggac   1320
gagttcatcg aggaagctaa ggtgatgatg aatctgagcc acgagaagct ggtgcagctc   1380
tacggcgtgt gtaccaagca aaggcccatc ttcattatca cagagtatat ggccaatggc   1440
tgcctcctca actatctgag agagatgagg catagattcc agacccaaca gctgctggag   1500
atgtgcaaag atgtgtgcga ggccatggag tacctcgaaa gcaagcagtt tctgcataga   1560
gacctcgccg ctagaaattg tctggtgaac gatcaaggcg tcgtgaaggt gagcgatttt   1620
ggactgagca gatacgtgct ggacgatgag tacaccagca gcgtcggatc caagttcccc   1680
gtgagatgga gccctcccga ggtgctgatg tactccaagt tcagctccaa gtccgacatc   1740
tgggccttg cgtgctgat gtgggagatt tactctctgg caagatgcc ctacgagagg   1800
tttaccaaca gcgagacagc cgaacacatc gcccaaggac tgaggctgta taggcccac   1860
ctcgcctccg agaaggtgta caccattatg tacagctgct ggcacgagaa ggccgacgag   1920
aggcccacat tcaagattct gctgtccaac attctggacg tgatggacga agagtcctga   1980
```

<210> SEQ ID NO 11
<211> LENGTH: 1980
<212> TYPE: DNA
<213> ORGANISM: Artificial Sequence
<220> FEATURE:
<223> OTHER INFORMATION: Synthetic

<400> SEQUENCE: 11

```
atggcggcag tgattttgga atccatcttc ctgaaacgca gtcagcagaa gaaaaaaact     60
agtccgctta actttaagaa aaggcttttc ttgttgacag tccacaagct gagttattat    120
gaatacgatt ttgaaagggg aaggaggggc tccaagaaag ggagtataga cgtcgagaag    180
attacatgcg ttgaaactgt tgtgccggag aagaatcccc cgccggaaag acaaattcct    240
cgacggggcg aagagtccag tgaaatggag caaatttcta ttatcgagcg cttcccttac    300
ccattccagg tagtatatga cgaagggccc ttgtacgtgt tctctccgac agaagaactc    360
cggaaacgct ggatccatca gttgaaaaat gtaatacgct acaatagtga cctggtacag    420
aaataccacc cttgtttttg gattgatggc caatacttgt gttgtagtca gacggcaaag    480
aatgcaatgg gttgccaaat tttggagaat cgaaacggga gcctcaagcc aggaagctct    540
catcgcaaaa caaaaaaacc cttgccaccg actcccgagg aagatcagat cctgaagaaa    600
```

```
cctcttcccc ctgagcctgc agcagctcct gtcagcacgt ccgagcttaa gaaagtggtc      660
gcattgtacg attacatgcc gatgaacgct aacgatctgc agctgagaaa aggcgacgag      720
tactttatcc tcgaggaatc taacctcccg tggtggagag caagagataa aaacggacaa      780 gagggtaca tcccctcaaa ttatgtgaca gaggcggagg attccatcga gatgtacgag       840
tggtattcaa agcacatgac tcggagccag gccgagcaat tgcttaaaca ggagggaaaa      900
gaaggtggct ttatagtgag ggactctagc aaggctggaa atacacggt gagcgtattt       960 gccaagtcta cgggagatcc ccaaggggtt ataaggcact acgtagtctg ttcaactccc     1020
cagagccagt actatcttgc ggaaaagcac ctcttctcca ctattcctga gctgataaat     1080
taccatcaac ataacagcgc gggcctgata agcaggctca aatacccggt ctcccaacag     1140
aacaagaacg caccttctac cgcagggctc ggttatggct catgggaaat tgacccgaaa     1200
gatcttactt tcctgaagga actcggcact ggccagttcg gcgttgtaaa gtacggaaaa     1260 tggagggac aatatgacgt cgcgataaaa atgatcaaag aggggtccat gagtgaggac      1320
gaatttattg aggaggcgaa agtaatgatg aatctcagtc atgaaaaact cgtacaattg     1380
tatggtgttt gcaccaaaca acgaccaatt tttatcataa ccgagtacat ggccaacggt     1440
tgtttgctta attacctgag agaaatgcga catcggttcc aaacacaaca actgcttgag     1500
atgtgtaagg atgtctgcga agcaatggag tacctcgaat caaaacagtt ccttcacaga     1560
gatcttgcgg cgcggaactg tctggttaac gatcagggcg tagttaaggt cagcgacttt     1620
gggctctcac gatatgttct tgatgatgag tataccagca gtgttggatc aaagttccct     1680
gttaggtggt caccgccaga ggttctgatg tatagcaagt tctcttctaa gagtgacatc     1740
tgggccttcg gagtactcat gtgggagatc tattccctgg gcaagatgcc ttacgagaga     1800
ttcaccaata gcgaaactgc ggaacacatc gcccaaggcc ttagactcta tcggccgcac     1860
ctcgcgagcg aaaaggtcta caatcatg tactcctgtt ggcatgagaa agctgatgag       1920
cgcccaacgt tcaagatact tctcagtaat atccttgacg taatggatga ggaatcctga     1980
```

<210> SEQ ID NO 12
<211> LENGTH: 1980
<212> TYPE: DNA
<213> ORGANISM: Artificial Sequence
<220> FEATURE:
<223> OTHER INFORMATION: Synthetic

<400> SEQUENCE: 12

```
atggccgcag tgattctgga gagcatcttt ctgaagcggt cccagcagaa aaagaaaaca       60
agccctctga acttcaagaa gcggctgttt ctcctgaccg tgcacaaact ctcctactac      120
gagtacgact tgaacggggg gcggcggggc agcaagaagg gcagcatcga tgtggagaag      180
atcacctgcg tggaaacagt ggtgcctgaa aagaatcctc ctccagaacg gcagattccc      240
cggcggggca agagtccag cgaaatggag cagattagca tcattgaacg gttcccttac       300
cccttccagg tggtgtacga tgaagggcct ctctacgtct ctcccccaac cgaagaactg      360
cggaagcggt ggattcacca gctcaaaaac gtgatccggt acaacagcga tctggtgcag      420
aaataccacc cttgcttctg gatcgatggg cagtacctct gctgctctca gacagccaaa      480
aatgctatgg gctgccagat tctggagaac cggaatggaa gcctgaaacc tgggagctct      540
caccggaaga caaagaagcc tctgccccca acccctgagg aggaccagat cctgaaaaag      600
ccactgcccc ctgagccagc agcagcacca gtctccacaa gcgagctgaa aaaggtggtg      660
```

```
gccctgtacg attacatgcc aatgaatgca aatgatctgc agctgcggaa gggcgatgaa      720
tactttatcc tggaggaaag caacctgcca tggtggcggg cacgggataa aaatgggcag      780
gaaggctaca ttcctagcaa ctacgtcacc gaagcagaag actccatcga aatgtacgag      840
tggtactcca acacatgac ccggagccag gctgagcagc tgctgaagca ggaggggaaa       900
gaaggaggct tcattgtccg ggactccagc aaagctggca atacacagt gtctgtcttt       960 gctaaatcca caggggaccc tcaggggta atccggcact acgtggtgtg ctccacacct      1020
cagagccagt actacctggc tgagaagcac ctgttcagca ccatccctga gctcattaac     1080
taccaccagc acaactctgc aggactcatc tcccggctca ataccccagt gtctcagcag     1140
aacaagaatg caccttccac cgcaggcctg ggatacggaa gctgggaaat tgatccaaag     1200
gacctgacct tcctgaagga gctggggacc ggacagttg gggtggtgaa gtacgggaaa      1260
tggcggggcc agtacgacgt ggccatcaag atgatcaaag aaggctccat gtctgaagat     1320
gaattcattg aagaagccaa agtcatgatg aatctgtccc acgagaagct ggtgcagctg     1380
tacggcgtct gcaccaagca gcggcccatc ttcatcatca ccgagtacat ggccaatggc     1440
tgcctcctga actacctgcg ggagatgcgg caccggttcc agacccagca gctgctggag     1500
atgtgcaagg atgtctgcga agccatgaa tacctggaga gcaagcagtt cctgcaccgg     1560
gacctggcag ctcggaactg cctggtgaac gatcagggag tggtgaaagt gtctgatttc     1620
ggcctgtccc ggtacgtcct ggatgatgaa tacacaagca gcgtgggctc caaatttcca     1680
gtccggtggt ccccacccga agtcctgatg tacagcaagt tcagcagcaa atctgacatt     1740
tgggcttttg ggtgctgat gtgggaaatc tattccctgg ggaagatgcc atacgagcgg     1800
tttaccaaca gcgagaccgc tgaacacatt gcccagggcc tgcggctcta ccggcctcac     1860
ctggctagcg agaaggtgta caccatcatg tacagctgct ggcacgagaa agcagatgag     1920
cggcccacct tcaaaattct gctgagcaat attctggatg tcatggatga agaatcctga     1980
```

<210> SEQ ID NO 13
<211> LENGTH: 1980
<212> TYPE: DNA
<213> ORGANISM: Artificial Sequence
<220> FEATURE:
<223> OTHER INFORMATION: Synthetic

<400> SEQUENCE: 13

```
atggccgctg tgatcctgga gagcattttc ctgaagaggt cccagcagaa aaagaaaacc       60
tctcccctga actttaagaa agactgttc ctgctgacag tgcacaagct gtcttactat       120
gagtacgact ttgagcgggg ccgccgagga tcaaaaaagg ggagcatcga tgtggagaag      180
attacatgcg tggagaccgt ggtccctgaa aagaatccac cccctgagag gcagatccca      240
agacggggcg aggagtcctc tgagatggag cagattagta tcattgagcg cttcccctat      300
ccttttcagg tggtgtacga cgagggacca ctgtatgtgt tctcacccac agaggagctg      360
agaaagaggt ggattcacca gctgaagaac gtgattagat acaatagcga tctggtgcag      420
aagtatcacc cttgttttttg gatcgacggg cagtacctgt gctgttccca gacagctaag      480
aacgctatgg gatgccagat tctggaaaat cggaacggat ctctgaaacc agggagttca      540
caccgcaaga ccaaaaagcc cctgcctcca acacccgagg aggatcagat cctgaaaaag      600
cctctgccac ccgagcctgc tgcagcccca gtcagcactt ccgaactgaa aaaggtggtg      660
gctctgtatg actacatgcc catgaatgct aacgatctgc agctgagaaa gggcgacgag      720
tatttcattc tggaagagtc taatctgcct tggtggaggg ccagagataa gaacggacag      780
```

```
gaggggtaca tcccatctaa ttatgtgacc gaggctgagg actctattga gatgtacgag    840
tggtatagca agcacatgac acggtcccag gctgagcagc tgctgaagca ggagggcaaa    900
gagggagggt ttatcgtgcg cgattctagt aaggccggca atacactgt gtcagtgttc     960 gctaagagca ccgagaccc ccagggcgtg atcagacact atgtggtgtg ttccacacct    1020
cagtctcagt actatctggc tgagaagcac ctgtttagta caatcccaga gctgattaac   1080
taccaccagc acaattctgc cggcctgatc agcaggctga agtatcccgt ctcccagcag   1140
aacaaaaatg ctccttctac cgctggactg gggtacggca gttgggagat tgatccaaag   1200
gacctgacat tcctgaagga gctgggaact gggcagtttg gcgtggtgaa gtatggaaaa   1260
tggagagggc agtacgatgt ggccatcaag atgatcaagg agggctcaat gagcgaggac   1320
gagttcatcg aggaggctaa ggtcatgatg aacctgtccc acgagaaact ggtgcagctg   1380
tatggagtgt gcaccaagca gcggcccatt tttatcatta cagagtacat ggctaatggg   1440
tgtctgctga actatctgcg cgagatgaga cacagattcc agacacagca gctgctggaa   1500
atgtgcaagg atgtgtgtga ggctatggag tacctggagt ctaagcagtt tctgcaccgg   1560
gacctggctg ctcgcaattg cctggtgaac gatcagggcg tggtgaaggt gagtgacttc   1620
ggactgtcaa ggtatgtgct ggatgacgag tacaccagct ccgtgggctc taagtttcct   1680
gtgagatggt ctccacccga ggtgctgatg tatagcaagt tctcctctaa gagcgatatc   1740
tgggcctttg gcgtgctgat gtgggaaatc tacagcctgg gcaagatgcc ttacgagcgg   1800
ttcacaaatt ccgagacagc tgagcacatc gcccagggcc tgcgcctgta ccggccacat   1860
ctggcctctg agaaggtgta caccatcatg tacagctgtt ggcacgagaa ggccgacgag   1920
agacccacat tcaagatcct gctgtccaac attctagatg tgatggacga ggagagctga   1980

<210> SEQ ID NO 14
<211> LENGTH: 160
<212> TYPE: DNA
<213> ORGANISM: Artificial Sequence
<220> FEATURE:
<223> OTHER INFORMATION: Synthetic

<400> SEQUENCE: 14
agactgtcct tcctctctgg actgtaagaa tatgtctcca gggccagtgt ctgctgcgat    60
cgagtcccac cttccaagtc ctggcatctc aatgcatctg gaagctacc tgcattaagt    120 caggactgag cacacaggtg aactccagaa agaagaagct                          160

<210> SEQ ID NO 15
<211> LENGTH: 31
<212> TYPE: DNA
<213> ORGANISM: Artificial Sequence
<220> FEATURE:
<223> OTHER INFORMATION: Synthetic

<400> SEQUENCE: 15
agactgtcct tcctctctgg actgtaagaa t                                    31

<210> SEQ ID NO 16
<211> LENGTH: 160
<212> TYPE: DNA
<213> ORGANISM: Artificial Sequence
<220> FEATURE:
<223> OTHER INFORMATION: Synthetic

<400> SEQUENCE: 16
```

```
agactgtcct tcctctctca actgtaacaa tatgtctcca gggccagtgt ctgctgcgat    60
cgagtcccac cttccaagtc ctggcatctc aatgcatctg gcaagctacc tgcaataagt   120
caccactgag cacacacaac aactccacaa acaacaagct                         160
```

<210> SEQ ID NO 17
<211> LENGTH: 41
<212> TYPE: DNA
<213> ORGANISM: Artificial Sequence
<220> FEATURE:
<223> OTHER INFORMATION: Synthetic

<400> SEQUENCE: 17

```
agactgtcct tcctctctgg actgtaagaa ttagtctcga g                        41
```

<210> SEQ ID NO 18
<211> LENGTH: 668
<212> TYPE: DNA
<213> ORGANISM: Artificial Sequence
<220> FEATURE:
<223> OTHER INFORMATION: Synthetic

<400> SEQUENCE: 18

```
cgcaaacacc cgaatcaact tctagtcaaa ttattgttca cgccgcaatg acccacccct    60
ggcccgcgtc tgtggaactg acccctggtg tacaggagag ttcgctgctg aaagtggtcc   120
caaaggggta ctagttttta agctcccaac tcccccctcc ccagcgtctg gaggattcca   180
caccctcgca ccgcaggggc gaggaagtgg gcggagtccg gttttggcgc cagccgctga   240
ggctgccaag cagaaaagcc accgctgagg agactccggt cactgtcctc gccccgcctc   300
ccccttccct ccccttgggg accaccgggc gccacgccgc gaacggtaag tgccgcggtc   360
gtcggcgcct ccgccctccc cctagggccc caattcccag cgggcgcggc gcgcggcccc   420 tcccccgcc gggcgcgcgc ccgctgcccc gcccttcgtg gccgcccggc gtgggcggtg     480 ccaccccctcc ccccagcggc cccgcgcgca gctcccggct ccctcccccct tcggatgtgg   540 cttgagctgt aggcgcggag ggccggagac gctgcagacc cgcgacccgg agcagctcgg   600
aggcggtgaa gtcggtggct ttccttctct ctagctctcg ctcgctggtg gtgcttcaga   660
tgccacac                                                           668
```

<210> SEQ ID NO 19
<211> LENGTH: 2333
<212> TYPE: DNA
<213> ORGANISM: Artificial Sequence
<220> FEATURE:
<223> OTHER INFORMATION: Synthetic

<400> SEQUENCE: 19

```
gactcaagat agtagtgtca gaggtcccaa gcaaatgaag ggcggggaca gttgaggggg    60
tggaataggg acggcagcag ggaaccagat agcatgctgc tgagaagaaa aaagacatt   120 ggtttaggtc aggaagcaaa aaagggaac tgagtggctg tgaaagggtg gggtttgctc    180
agactgtcct tcctctctgg actgtaagaa tatgtctcca gggccagtgt ctgctgcgat   240
cgagtcccac cttccaagtc ctggcatctc aatgcatctg ggaagctacc tgcattaagt   300
caggactgag cacacaggtg aactccagaa agaagaagct gccgccrcca tggatggccg   360
cagtgattct ggagagcatc tttctgaagc gatcccaaca gaaaaagaaa acatcacctc   420
taaacttcaa gaagcgcctg tttctcttga ccgtgcacaa actctcctac tatgagtatg   480
actttgaacg tgggagaaga ggcagtaaga agggttcaat agatgttgag aagatcactt   540
```

```
gtgttgaaac agtggttcct gaaaaaaatc ctcctccaga aagacagatt ccgagaagag      600
gtgaagagtc cagtgaaatg gagcaaattt caatcattga aaggttccct tatcccttcc      660
aggttgtata tgatgaaggg cctctctacg tcttctcccc aactgaagaa ctaaggaagc      720
ggtggattca ccagctcaaa aacgtaatcc ggtacaacag tgatctggtt cagaaatatc      780
acccttgctt ctggatcgat gggcagtatc tctgctgctc tcagacagcc aaaaatgcta      840
tgggctgcca aattttggag aacaggaatg gaagcttaaa acctgggagt ctcaccgga       900 agacaaaaaa gcctcttccc ccaacgcctg aggaggacca gatcttgaaa agccactac       960 cgcctgagcc agcagcagca ccagtctcca caagtgagct gaaaaaggtt gtggcccttt     1020
atgattacat gccaatgaat gcaaatgatc tacagctgcg gaagggtgat gaatatttta     1080
tcttggagga aagcaactta ccatggtgga gagcacgaga taaaaatggg caggaaggct     1140
acattcctag taactatgtc actgaagcag aagactccat agaaatgtat gagtggtatt     1200
ccaaacacat gactcggagt caggctgagc aactgctaaa gcaagagggg aaagaaggag     1260
gtttcattgt cagagactcc agcaaagctg gcaaatatac agtgtctgtg tttgctaaat     1320
ccacagggga ccctcaaggg gtgatacgtc attatgttgt gtgttccaca cctcagagcc     1380
agtattacct ggctgagaag caccttttca gcaccatccc tgagctcatt aactaccatc     1440
agcacaactc tgcaggactc atatccaggc tcaaatatcc agtgtctcaa caaaacaaga     1500
atgcaccttc cactgcaggc ctgggatacg gatcatggga aattgatcca aaggacctga     1560
ccttcttgaa ggagctgggg actggacaat tggggtagt gaagtatggg aaatggagag      1620
gccagtacga cgtggccatc aagatgatca agaaggctc catgtctgaa gatgaattca     1680
ttgaagaagc caaagtcatg atgaatcttt cccatgagaa gctggtgcag ttgtatggcg     1740
tctgcaccaa gcagcgcccc atcttcatca tcactgagta catggccaat ggctgcctcc     1800
tgaactacct gagggagatg cgccaccgct tccagactca gcagctgcta gagatgtgca     1860
aggatgtctg tgaagccatg gaatacctgg agtcaaagca gttccttcac cgagacctgg     1920
cagctcgaaa ctgtttggta aacgatcaag gagttgttaa agtatctgat ttcggcctgt     1980
ccaggtatgt cctggatgat gaatacacaa gctcagtagg ctccaaattt ccagtccggt     2040
ggtccccacc ggaagtcctg atgtatagca agttcagcag caaatctgac atttgggctt     2100 ttgggggtttt gatgtgggaa atttactccc tggggaagat gccatgagag agatttacta     2160
acagtgagac tgctgaacac attgcccaag gcctacgtct ctacaggcct catctggctt     2220
cagagaaggt ataccatcc atgtacagtt gctggcatga aaagcagat gagcgtccca      2280 cttttcaaaat tcttctgagc aatattctag atgtcatgga tgaagaatcc tga           2333
```

<210> SEQ ID NO 20
<211> LENGTH: 2551
<212> TYPE: DNA
<213> ORGANISM: Artificial Sequence
<220> FEATURE:
<223> OTHER INFORMATION: Synthetic

<400> SEQUENCE: 20

```
gctcttcctg ccagtctct ttgctctgtg tctgccagcc cccagcatct ctcctctttc       60
ctgtaagccc ctctccctgt gctgactgtc ttcatagtac tttaggtatg ttgtcccttt      120
acctctggga ggatagcttg atgacctgtc tgctcaggcc agccccatct agagtctcag      180
tggccccagt catgttgaga aaggttcttt caaagataga ctcaagatag tagtgtcaga      240
```

```
ggtcccaagc aaatgaaggg cggggacagt tgagggggtg gaatagggac ggcagcaggg      300
aaccagatag catgctgctg agaagaaaaa aagacattgg tttaggtcag gaagcaaaaa      360
aagggaactg agtggctgtg aaagggtggg gtttgctcag actgtccttc ctctctggac      420
tgtaagaata tgtctccagg gccagtgtct gctgcgatcg agtcccacct tccaagtcct      480
ggcatctcaa tgcatctggg aagctacctg cattaagtca ggactgagca cacaggtgaa      540
ctccagaaag aagaagctgc cgccrccaug gatggccgca gtgattctgg agagcatctt      600
tctgaagcga tcccaacaga aaagaaaaac atcacctcta aacttcaaga agcgcctgtt      660
tctcttgacc gtgcacaaac tctcctacta tgagtatgac tttgaacgtg ggagaagagg      720
cagtaagaag ggttcaatag atgttgagaa gatcacttgt gttgaaacag tggttcctga      780
aaaaaatcct cctccagaaa gacagattcc gagaagaggt gaagagtcca gtgaaatgga      840
gcaaatttca atcattgaaa ggttcccctta tcccttccag gttgtatatg atgaagggcc      900
tctctacgtc ttctccccaa ctgaagaact aaggaagcgg tggattcacc agctcaaaaa      960
cgtaatccgg tacaacagtg atctggttca gaaatatcac ccttgcttct ggatcgatgg     1020
gcagtatctc tgctgctctc agacagccaa aaatgctatg ggctgccaaa ttttggagaa     1080
caggaatgga agcttaaaac ctgggagttc tcaccggaag acaaaaaagc ctcttccccc     1140
aacgcctgag gaggaccaga tcttgaaaaa gccactaccg cctgagccag cagcagcacc     1200
agtctccaca agtgagctga aaaaggttgt ggcccttttat gattacatgc caatgaatgc     1260
aaatgatcta cagctgcgga agggtgatga atattttatc ttggaggaaa gcaacttacc     1320
atggtggaga gcacgagata aaaatgggca ggaaggctac attcctagta actatgtcac     1380
tgaagcagaa gactccatag aaatgtatga gtggtattcc aaacacatga ctcggagtca     1440
ggctgagcaa ctgctaaagc aagaggggaa agaaggaggt tcattgtca gagactccag     1500 caaagctggc aaatatacag tgtctgtgtt tgctaaatcc acaggggacc ctcaagggt     1560 gatacgtcat tatgttgtgt gttccacacc tcagagccag tattacctgg ctgagaagca     1620 cctttttcagc accatccctg agctcattaa ctaccatcag cacaactctg caggactcat     1680
atccaggctc aaatatccag tgtctcaaca aaacaagaat gcaccttcca ctgcaggcct     1740
gggatacgga tcatgggaaa ttgatccaaa ggacctgacc ttcttgaagg agctggggac     1800
tggacaattt ggggtagtga agtatgggaa atggagaggc cagtacgacg tggccatcaa     1860
gatgatcaaa gaaggctcca tgtctgaaga tgaattcatt gaagaagcca agtcatgat      1920 gaatcttttcc catgagaagc tggtgcagtt gtatggcgtc tgcaccaagc agcgccccat     1980
cttcatcatc actgagtaca tggccaatgg ctgcctcctg aactacctga gggagatgcg     2040
ccaccgcttc cagactcagc agctgctaga gatgtgcaag gatgtctgtg aagccatgga     2100
atacctggag tcaaagcagt tccttcaccg agacctggca gctcgaaact gtttggtaaa     2160
cgatcaagga gttgttaaag tatctgattt cggcctgtcc aggtatgtcc tggatgatga     2220
atacacaagc tcagtaggct ccaaatttcc agtccggtgg tccccaccgg aagtcctgat     2280
gtatagcaag ttcagcagca atctgacat ttgggctttt ggggttttga tgtgggaaat      2340
ttactccctg gggaagatgc catatgagag atttactaac agtgagactg ctgaacacat     2400
tgcccaaggc ctacgtctct acaggcctca tctggcttca gagaaggtat ataccatcat     2460
gtacagttgc tggcatgaga aagcagatga gcgtcccact ttcaaaattc ttctgagcaa     2520
tattctagat gtcatggatg aagaatcctg a                                    2551
```

<210> SEQ ID NO 21
<211> LENGTH: 2741
<212> TYPE: DNA
<213> ORGANISM: Artificial Sequence
<220> FEATURE:
<223> OTHER INFORMATION: Synthetic

<400> SEQUENCE: 21

| | | | | | |
|---|---|---|---|---|---|
| gtatttctgt | gggcttatat | tccgacattt | ttatctgtag | gggaaaaatg | ctttcttaga | 60 |
| aaatgactca | gcacgggaa | gtcttgtctc | tacctctgtc | ttgttttgtc | ctttggggtc | 120 |
| ccttcactat | caagttcaac | tgtgtgtccc | tgagactcct | ctgccccgga | ggacaggaga | 180 |
| ctcgaaaaac | gctcttcctg | gccagtctct | ttgctctgtg | tctgccagcc | ccagcatct | 240 |
| ctcctctttc | ctgtaagccc | ctctccctgt | gctgactgtc | ttcatagtac | tttaggtatg | 300 |
| ttgtcccttt | acctctggga | ggatagcttg | atgacctgtc | tgctcaggcc | agccccatct | 360 |
| agagtctcag | tggccccagt | catgttgaga | aaggttcttt | caaagataga | ctcaagatag | 420 |
| tagtgtcaga | ggtcccaagc | aaatgaaggg | cggggacagt | tgaggggtg | gaatagggac | 480 |
| ggcagcaggg | aaccagatag | catgctgctg | agaagaaaaa | aagacattgg | tttaggtcag | 540 |
| gaagcaaaaa | aagggaactg | agtggctgtg | aaagggtggg | gtttgctcag | actgtccttc | 600 |
| ctctctggac | tgtaagaata | tgtctccagg | gccagtgtct | gctgcgatcg | agtcccacct | 660 |
| tccaagtcct | ggcatctcaa | tgcatctggg | aagctacctg | cattaagtca | ggactgagca | 720 |
| cacaggtgaa | ctccagaaag | aagaagctgc | cgccrccaug | gatggccgca | gtgattctgg | 780 |
| agagcatctt | tctgaagcga | tcccaacaga | aaaagaaaac | atcacctcta | aacttcaaga | 840 |
| agcgcctgtt | tctcttgacc | gtgcacaaac | tctcctacta | tgagtatgac | tttgaacgtg | 900 |
| ggagaagagg | cagtaagaag | ggttcaatag | atgttgagaa | gatcacttgt | gttgaaacag | 960 |
| tggttcctga | aaaaatcct | cctccagaaa | gacagattcc | gagaagaggt | gaagagtcca | 1020 |
| gtgaaatgga | gcaaatttca | atcattgaaa | ggttcccttta | tcccttccag | gttgtatatg | 1080 |
| atgaagggcc | tctctacgtc | ttctccccaa | ctgaagaact | aaggaagcgg | tggattcacc | 1140 |
| agctcaaaaa | cgtaatccgg | tacaacagtg | atctggttca | gaaatatcac | ccttgcttct | 1200 |
| ggatcgatgg | gcagtatctc | tgctgctctc | agacagccaa | aaatgctatg | ggctgccaaa | 1260 |
| ttttggagaa | caggaatgga | agcttaaaac | ctgggagttc | tcaccggaag | acaaaaaagc | 1320 |
| ctcttccccc | aacgcctgag | gaggaccaga | tcttgaaaaa | gccactaccg | cctgagccag | 1380 |
| cagcagcacc | agtctccaca | agtgagctga | aaaaggttgt | ggccctttat | gattacatgc | 1440 |
| caatgaatgc | aaatgatcta | cagctgcgga | agggtgatga | atattttatc | ttggaggaaa | 1500 |
| gcaacttacc | atggtggaga | gcacgagata | aaaatgggca | ggaaggctac | attcctagta | 1560 |
| actatgtcac | tgaagcagaa | gactccatag | aaatgtgatga | gtggtattcc | aaacacatga | 1620 |
| ctcggagtca | ggctgagcaa | ctgctaaagc | aagagggaa | agaaggaggt | ttcattgtca | 1680 |
| gagactccag | caaagctggc | aaatatacag | tgtctgtgtt | tgctaaatcc | acaggggacc | 1740 |
| ctcaaggggt | gatacgtcat | tatgttgtgt | gttccacacc | tcagagccag | tattacctgg | 1800 |
| ctgagaagca | ccttttcagc | accatccctg | agctcattaa | ctaccatcag | cacaactctg | 1860 |
| caggactcat | atccaggctc | aaatatccag | tgtctcaaca | aaacaagaat | gcaccttcca | 1920 |
| ctgcaggcct | gggatacgga | tcatgggaaa | ttgatccaaa | ggacctgacc | ttcttgaagg | 1980 |
| agctggggac | tggacaattt | ggggtagtga | agtatgggaa | atggagaggc | cagtacgacg | 2040 |
| tggccatcaa | gatgatcaaa | gaaggctcca | tgtctgaaga | tgaattcatt | gaagaagcca | 2100 |

| | |
|---|---:|
| aagtcatgat gaatctttcc catgagaagc tggtgcagtt gtatggcgtc tgcaccaagc | 2160 |
| agcgccccat cttcatcatc actgagtaca tggccaatgg ctgcctcctg aactacctga | 2220 |
| gggagatgcg ccaccgcttc cagactcagc agctgctaga gatgtgcaag gatgtctgtg | 2280 |
| aagccatgga atacctggag tcaaagcagt tccttcaccg agacctggca gctcgaaact | 2340 |
| gtttggtaaa cgatcaagga gttgttaaag tatctgattt cggcctgtcc aggtatgtcc | 2400 |
| tggatgatga atacacaagc tcagtaggct ccaaatttcc agtccggtgg tccccaccgg | 2460 |
| aagtcctgat gtatagcaag ttcagcagca aatctgacat ttgggctttt ggggttttga | 2520 |
| tgtgggaaat ttactccctg gggaagatgc catatgagag atttactaac agtgagactg | 2580 |
| ctgaacacat tgcccaaggc ctacgtctct acaggcctca tctggcttca gagaaggtat | 2640 |
| ataccatcat gtacagttgc tggcatgaga aagcagatga gcgtcccact ttcaaaattc | 2700 |
| ttctgagcaa tattctagat gtcatggatg aagaatcctg a | 2741 |

<210> SEQ ID NO 22
<211> LENGTH: 3186
<212> TYPE: DNA
<213> ORGANISM: Artificial Sequence
<220> FEATURE:
<223> OTHER INFORMATION: Synthetic

<400> SEQUENCE: 22

| | |
|---|---:|
| accccatttt ttttgtttgc ttgtttgttt gttttttaga caaaataaag aaaaaaaaat | 60 |
| aaggtcctgt tgacttaaaa cttcggatga aattgtagtg ggacctgtga tctgtttcta | 120 |
| cattaggata cagtgccttg gggcaaggaa atatggcagt gcccgaggtg tcaaggtggg | 180 |
| caggcagatc agtcagcagg ggctccacca tcatggtctg cattcaatac tggctgcatt | 240 |
| tcctaggaga atccctgggg gaatcattgc agttggagca taatgtaggg ggcccctgag | 300 |
| aaaacctcca ggcttcaagt gacatacctc gtctgcttta ccggtttaca ggactcaaga | 360 |
| gaaaggtgga cattgagagt taatccctga ggccaaatct taaatggaga aagtcaacat | 420 |
| ccacagaaaa tggggaaggg cacaagtatt tctgtgggct tatattccga cattttttatc | 480 |
| tgtagggaaa aaatgctttc ttagaaaatg actcagcacg gggaagtctt gtctctacct | 540 |
| ctgtcttgtt ttgtccttg gggtcccttc actatcaagt tcaactgtgt gtccctgaga | 600 |
| ctcctctgcc ccggaggaca ggagactcga aaaacgctct tcctggccag tctcttgct | 660 |
| ctgtgtctgc cagcccccag catctctcct cttttcctgta agcccctctc cctgtgctga | 720 |
| ctgtcttcat agtactttag gtatgttgtc ccttttacctc tgggaggata gcttgatgac | 780 |
| ctgtctgctc aggccagccc catctagagt ctcagtggcc ccagtcatgt tgagaaaggt | 840 |
| tctttcaaag atagactcaa gatagtagtg tcagaggtcc caagcaaatg aagggcgggg | 900 |
| acagttgagg gggtggaata gggacggcag cagggaacca gatagcatgc tgctgagaag | 960 |
| aaaaaaagac attggtttag gtcaggaagc aaaaaagggg aactgagtgg ctgtgaaagg | 1020 |
| gtggggtttg ctcagactgt ccttcctctc tggactgtaa gaatatgtct ccagggccag | 1080 |
| tgtctgctgc gatcgagtcc caccttccaa gtcctggcat ctcaatgcat ctgggaagct | 1140 |
| acctgcatta agtcaggact gagcacacag gtgaactcca gaagaagaa gctgccgccr | 1200 |
| ccauggatgg ccgcagtgat tctggagagc atctttctga agcgatccca acagaaaaag | 1260 |
| aaaacatcac ctctaaactt caagaagcgc ctgtttctct tgaccgtgca caaactctcc | 1320 |
| tactatgagt atgactttga acgtgggaga agaggcagta agaagggttc aatagatgtt | 1380 |
| gagaagatca cttgtgttga aacagtggtt cctgaaaaaa atcctcctcc agaaagacag | 1440 |

| | | | | |
|---|---|---|---|---|
| attccgagaa | gaggtgaaga | gtccagtgaa | atggagcaaa | tttcaatcat tgaaaggttc | 1500 |
| ccttatccct | tccaggttgt | atatgatgaa | gggcctctct | acgtcttctc cccaactgaa | 1560 |
| gaactaagga | agcggtggat | tcaccagctc | aaaaacgtaa | tccggtacaa cagtgatctg | 1620 |
| gttcagaaat | atcacccttg | cttctggatc | gatgggcagt | atctctgctg ctctcagaca | 1680 |
| gccaaaaatg | ctatgggctg | ccaaattttg | gagaacagga | atggaagctt aaaacctggg | 1740 |
| agttctcacc | ggaagacaaa | aaagcctctt | ccccccaacgc | ctgaggagga ccagatcttg | 1800 |
| aaaaagccac | taccgcctga | gccagcagca | gcaccagtct | ccacaagtga gctgaaaaag | 1860 |
| gttgtggccc | tttatgatta | catgccaatg | aatgcaaatg | atctacagct gcggaagggt | 1920 |
| gatgaatatt | ttatcttgga | ggaaagcaac | ttaccatggt | ggagagcacg agataaaaat | 1980 |
| gggcaggaag | gctacattcc | tagtaactat | gtcactgaag | cagaagactc catagaaatg | 2040 |
| tatgagtggt | attccaaaca | catgactcgg | agtcaggctg | agcaactgct aaagcaagag | 2100 |
| gggaaagaag | gaggtttcat | tgtcagagac | tccagcaaag | ctggcaaata tacagtgtct | 2160 |
| gtgtttgcta | atccacagg | ggaccctcaa | ggggtgatac | gtcattatgt tgtgtgttcc | 2220 |
| acacctcaga | gccagtatta | cctggctgag | aagcaccttt | tcagcaccat ccctgagctc | 2280 |
| attaactacc | atcagcacaa | ctctgcagga | ctcatatcca | ggctcaaata tccagtgtct | 2340 |
| caacaaaaca | agaatgcacc | ttccactgca | ggcctgggat | acggatcatg ggaaattgat | 2400 |
| ccaaaggacc | tgaccttctt | gaaggagctg | gggactggac | aatttggggt agtgaagtat | 2460 |
| gggaaatgga | gaggccagta | cgacgtggcc | atcaagatga | tcaaagaagg ctccatgtct | 2520 |
| gaagatgaat | tcattgaaga | agccaaagtc | atgatgaatc | tttcccatga aagctggtg | 2580 |
| cagttgtatg | gcgtctgcac | caagcagcgc | cccatcttca | tcatcactga gtacatggcc | 2640 |
| aatggctgcc | tcctgaacta | cctgagggag | atgcgccacc | gcttccagac tcagcagctg | 2700 |
| ctagagatgt | gcaaggatgt | ctgtgaagcc | atggaatacc | tggagtcaaa gcagttcctt | 2760 |
| caccgagacc | tggcagctcg | aaactgtttg | gtaaacgatc | aaggagttgt taaagtatct | 2820 |
| gatttcggcc | tgtccaggta | tgtcctggat | gatgaataca | caagctcagt aggctccaaa | 2880 |
| tttccagtcc | ggtggtcccc | accggaagtc | ctgatgtata | gcaagttcag cagcaaatct | 2940 |
| gacatttggg | cttttgggt | tttgatgtgg | gaaatttact | ccctggggaa gatgccatat | 3000 |
| gagagattta | ctaacagtga | gactgctgaa | cacattgccc | aaggcctacg tctctacagg | 3060 |
| cctcatctgg | cttcagagaa | ggtatatacc | atcatgtaca | gttgctggca tgagaaagca | 3120 |
| gatgagcgtc | ccactttcaa | aattcttctg | agcaatattc | tagatgtcat ggatgaagaa | 3180 |
| tcctga | | | | | 3186 |

<210> SEQ ID NO 23
<211> LENGTH: 3186
<212> TYPE: DNA
<213> ORGANISM: Artificial Sequence
<220> FEATURE:
<223> OTHER INFORMATION: Synthetic

<400> SEQUENCE: 23

| | | | | |
|---|---|---|---|---|
| accccatttt | ttttgtttgc | ttgtttgttt | gttttttaga | caaaataaag aaaaaaaaat | 60 |
| aaggtcctgt | tgacttaaaa | cttcggatga | aattgtagtg | ggacctgtga tctgtttcta | 120 |
| cattaggata | cagtgccttg | gggcaaggaa | atatggcagt | gcccgaggtg tcaaggtggg | 180 |
| caggcagatc | agtcagcagg | ggctccacca | tcatggtctg | cattcaatac tggctgcatt | 240 |

```
tcctaggaga atccctgggg gaatcattgc agttggagca taatgtaggg ggcccctgag        300
aaaacctcca ggcttcaagt gacataccta gtctgcttta ccggtttaca ggactcaaga        360
gaaaggtgga cattgagagt taatccctga ggccaaatct taaatggaga agtcaacat         420 ccacagaaaa tggggaaggg cacaagtatt tctgtgggct tatattccga cattttatc         480 tgtaggggaa aaatgctttc ttagaaaatg actcagcacg gggaagtctt gtctctacct        540
ctgtcttgtt ttgtcctttg ggtcccttc actatcaagt tcaactgtgt gtccctgaga         600
ctcctctgcc ccggaggaca ggagactcga aaaacgctct tcctggccag tctctttgct        660
ctgtgtctgc cagcccccag catctctcct ctttcctgta agcccctctc cctgtgctga        720
ctgtcttcat agtactttag gtatgttgtc ccttttacctc tgggaggata gcttgatgac       780
ctgtctgctc aggccagccc catctagagt ctcagtggcc ccagtcatgt tgagaaaggt        840
tctttcaaag atagactcaa gatagtagtg tcagaggtcc caagcaaatg aagggcgggg       900
acagttgagg gggtggaata gggacggcag cagggaacca gatagcatgc tgctgagaag       960
aaaaaaagac attggtttag gtcaggaagc aaaaaagggg aactgagtgg ctgtgaaagg      1020
gtggggtttg ctcagactgt ccttcctctc tggactgtaa gaatatgtct ccagggccag       1080
tgtctgctgc gatcgagtcc caccttccaa gtcctggcat ctcaatgcat ctgggaagct      1140
acctgcatta agtcaggact gagcacacag gtgaactcca gaaagaagaa gctgccgccr       1200
ccauggatgg ccgccgtcat cctagagagc atcttcctga agagatctca gcaaaagaag      1260
aaaacctccc ctctgaactt caagaagcgg ctgttcctgc tgaccgtgca caaactgagc      1320
tactacgagt acgatttcga gcggggaaga agaggaagca agaagggctc tatcgacgtg      1380
gaaaaaatca catgcgtgga gaccgtggtg cccgagaaga accctccacc agaacggcag      1440
atccccagaa gggggggagga atctagcgag atggaacaga tcagcatcat cgagaggttt      1500
ccttatcctt tccaggtggt ttacgacgaa ggtcctctgt atgtgttcag ccccacagaa      1560
gaactgcgga agcgctggat ccaccagctg aagaacgtga tcagatacaa cagcgacctg      1620
gtgcagaaat accacccctg cttctggatc gacggccagt acctgctgcag agccaaaaca      1680 gccaagaatg ctatgggctg ccagatcctg aaaaccgaa acggctctct gaaacctggc      1740
agcagccatc ggaagaccaa gaagcccctg cctcctaccc ccgaagagga ccaaatcctg      1800
aagaaacctc tgccacctga gccagccgct gctcctgtga gcacctccga gctgaaaaag      1860
gtggtcgccc tgtacgatta catgcctatg aacgccaacg acctccagtt gcgcaagggc      1920
gacgagtact tcattctgga agagtccaac ctgcctggt ggcgggccag agataagaac       1980
ggccaagagg gctatatccc cagcaattac gtgaccgagg ccgaagattc gatcgagatg      2040
tacgagtggt acagcaagca catgaccaga agccaggccg agcagctgct gaagcaggag      2100
ggcaaggaag gcggcttcat cgttagagat tcttctaaag ccggcaagta cacagtgtcc      2160
gtgttcgcca agagcacagg cgatcccag ggagtcattc ggcactacgt ggtgtgtagt      2220 accccctcaga gccagtacta cctggctgag aagcacctgt tctctacaat ccctgagctg      2280
atcaactacc accagcacaa cagcgccggc ctgatcagca gactgaaata ccccgtgagc      2340
caacagaaca gaacgcccc ctctacagcc ggcctgggat atggaagctg ggagatcgac      2400
cccaaggacc tgaccttcct gaaggaactg ggcaccggcc agtttggagt ggtcaagtac      2460
ggcaaatgga gaggccagta cgatgtggcc atcaagatga tcaaggaggg ctctatgagc      2520
gaagatgagt tcatagagga agcgaaagtg atgatgaatc tgtctcatga aagctggtg      2580 cagctgtacg gcgtgtgtac aaaacagaga cctatcttta ttatcaccga gtacatggct      2640
```

```
aacggctgtc tgctgaatta cctgcgggaa atgagacaca gattccagac acagcaactg    2700
ctggagatgt gcaaggacgt gtgcgaggcc atggaatacc tggaatccaa gcagttcctg    2760
caccgggacc tggccgccag aaattgtctg gtgaacgacc agggcgtggt caaggtgtcc    2820
gacttcggcc tgagcagata cgtgctggac gacgaataca ccagcagcgt gggcagcaaa    2880
ttccctgtca gatggagccc tcctgaagtg ctgatgtaca gcaagttcag cagcaagagc    2940
gacatctggg cctttggagt gctgatgtgg gaaatctact ctctgggcaa gatgccttac    3000
gagagattca ccaacagcga aaccgccgag cacatcgccc agggcctgcg gctgtatcgg    3060
cctcacctgg ccagcgagaa agtgtacacc atcatgtata gctgctggca cgagaaggcc    3120
gacgagagac ctacctttaa gatcctgctg tccaacatcc tggatgtgat ggacgaggaa    3180
tcctga                                                               3186

<210> SEQ ID NO 24
<211> LENGTH: 3186
<212> TYPE: DNA
<213> ORGANISM: Artificial Sequence
<220> FEATURE:
<223> OTHER INFORMATION: Synthetic

<400> SEQUENCE: 24
accccatttt ttttgtttgc ttgtttgttt gttttttaga caaaataaag aaaaaaaaat      60
aaggtcctgt tgacttaaaa cttcggatga aattgtagtg ggacctgtga tctgtttcta     120
cattaggata cagtgccttg ggcaaggaa atatggcagt gcccgaggtg tcaaggtggg      180
caggcagatc agtcagcagg ggctccacca tcatggtctg cattcaatac tggctgcatt     240
tcctaggaga atccctgggg gaatcattgc agttggagca taatgtaggg gcccctgag     300 aaaacctcca ggcttcaagt gacatacta gtctgcttta ccggtttaca ggactcaaga     360
gaaaggtgga cattgagagt taatccctga ggccaaatct taaatggaga aagtcaacat    420
ccacagaaaa tggggaaggg cacaagtatt tctgtgggct tatattccga cattttatc     480 tgtaggggaa aaatgctttc ttagaaaatg actcagcacg gggaagtctt gtctctacct     540
ctgtcttgtt ttgtccttg gggtcccttc actatcaagt tcaactgtgt gtccctgaga     600
ctcctctgcc ccggaggaca ggagactcga aaaacgctct tcctggccag tctctttgct     660
ctgtgtctgc cagcccccag catctctcct ctttcctgta gcccctctc cctgtgctga     720 ctgtcttcat agtactttag gtatgttgtc cctttacctc tgggaggata gcttgatgac     780
ctgtctgctc aggccagccc catctagagt ctcagtggcc ccagtcatgt tgagaaaggt     840
tctttcaaag atagactcaa gatagtagtg tcagaggtcc caagcaaatg aagggcgggg     900
acagttgagg gggtggaata gggacggcag caggaaccaa gatagcatgc tgctgagaag    960
aaaaaaagac attggtttag gtcaggaagc aaaaaagg aactgagtgg ctgtgaaagg    1020
gtggggtttg ctcagactgt ccttcctctc tggactgtaa gaatatgtct ccagggccag   1080
tgtctgctgc gatcgagtcc caccttccaa gtcctggcat ctcaatgcat ctgggaagct   1140
acctgcatta agtcaggact gagcacacag gtgaactcca gaaagaagaa gctgccgccr   1200
ccauggatgg ccgctgtgat tctggagagc atcttcctca agaggtccca gcagaagaag   1260
aagaccagcc ccctcaactt caagaagagg ctgttcctcc tcaccgtcca taagctgagc   1320
tactacgagt acgacttcga aaggggaaga aggggctcca aaaagggctc catcgacgtg   1380
gagaagatca catgcgtgga aaccgtggtc cccgaaaaaa atccccccccc cgaaaggcag   1440
```

| | |
|---|---|
| atccccagaa ggggagagga gtccagcgaa atggagcaga tctccatcat cgaaaggttc | 1500 |
| ccctacccct tccaagtggt gtacgacgaa ggccctctgt acgtgttctc ccccaccgaa | 1560 |
| gaactgagaa agaggtggat ccaccagctg aagaacgtca ttagatacaa ctccgacctc | 1620 |
| gtgcagaaat accacccttg cttctggatc gacggccagt atctgtgttg cagccaaaca | 1680 |
| gccaagaacg ctatgggctg ccagattctg gagaatagaa acggcagcct caagcccggc | 1740 |
| agcagccata ggaagaccaa aaagcctctg cctcccaccc cgaggagga tcagattctg | 1800 |
| aagaagcctc tgcctcccga gcccgccgct gctcccgtga gcacatccga gctgaagaag | 1860 |
| gtggtcgctc tgtacgacta catgcccatg aacgccaatg acctccaact gagaaaggga | 1920 |
| gacgagtact ttattctgga ggagagcaac ctcccttggt ggagagctag ggataagaat | 1980 |
| ggccaagagg gatacatccc cagcaactat gtgaccgagg ccgaggacag cattgagatg | 2040 |
| tacgagtggt acagcaagca tatgacaaga tcccaagccg agcaactgct gaagcaagag | 2100 |
| ggcaaggagg gcggcttcat tgtgagagac agctccaagg ctggcaaata caccgtgagc | 2160 |
| gtgttcgcca agagcaccgg cgatcccaa ggcgtgatca gacattacgt cgtgtgcagc | 2220 |
| accctcagt cccagtacta cctcgccgag aaacacctct tctccacaat ccccgagctg | 2280 |
| attaactacc accagcacaa ctccgccggc ctcatttcta gactgaagta ccccgtcagc | 2340 |
| cagcagaata agaatgctcc ctccacagct ggactgggct acggaagctg ggagatcgac | 2400 |
| cccaaagatc tgaccttct gaaagaactg gcaccggcc aatttggcgt ggtgaagtac | 2460 |
| ggcaagtgga ggggccagta cgacgtggct attaagatga tcaaggaggg aagcatgtcc | 2520 |
| gaggacgagt tcatcgagga agctaaggtg atgatgaatc tgagccacga gaagctggtg | 2580 |
| cagctctacg gcgtgtgtac caagcaaagg cccatcttca ttatcacaga gtatatggcc | 2640 |
| aatggctgcc tcctcaacta tctgagagag atgaggcata gattccagac caacagctg | 2700 |
| ctggagatgt gcaaagatgt gtgcgaggcc atggagtacc tcgaaagcaa gcagtttctg | 2760 |
| catagagacc tcgccgctag aaattgtctg gtgaacgatc aaggcgtcgt gaaggtgagc | 2820 |
| gattttggac tgagcagata cgtgctggac gatgagtaca ccagcagcgt cggatccaag | 2880 |
| ttccccgtga gatggagccc tcccgaggtg ctgatgtact ccaagttcag ctccaagtcc | 2940 |
| gacatctggg cctttggcgt gctgatgtgg gagatttact ctctgggcaa gatgccctac | 3000 |
| gagaggttta ccaacagcga gacagccgaa cacatcgccc aaggactgag gctgtatagg | 3060 |
| ccccacctcg cctccgagaa ggtgtacacc attatgtaca gctgctggca cgagaaggcc | 3120 |
| gacgagaggc ccacattcaa gattctgctg tccaacattc tggacgtgat ggacgaagag | 3180 |
| tcctga | 3186 |

<210> SEQ ID NO 25
<211> LENGTH: 3186
<212> TYPE: DNA
<213> ORGANISM: Artificial Sequence
<220> FEATURE:
<223> OTHER INFORMATION: Synthetic

<400> SEQUENCE: 25

| | |
|---|---|
| acccccatttt ttttgtttgc ttgtttgttt gttttttaga caaaataaag aaaaaaaat | 60 |
| aaggtcctgt tgacttaaaa cttcggatga aattgtagtg ggacctgtga tctgtttcta | 120 |
| cattaggata cagtgccttg gggcaaggaa atatggcagt gcccgaggtg tcaaggtggg | 180 |
| caggcagatc agtcagcagg ggctccacca tcatggtctg cattcaatac tggctgcatt | 240 |
| tcctaggaga atccctgggg gaatcattgc agttggagca taatgtaggg ggcccctgag | 300 |

```
aaaacctcca ggcttcaagt gacatatccta gtctgcttta ccggtttaca ggactcaaga    360
gaaaggtgga cattgagagt taatccctga ggccaaatct taaatggaga aagtcaacat    420
ccacagaaaa tggggaaggg cacaagtatt tctgtgggct tatattccga catttttatc    480
tgtagtggaa aaatgctttc ttagaaaatg actcagcacg gggaagtctt gtctctacct    540
ctgtcttgtt ttgtccttttg gggtcccttc actatcaagt tcaactgtgt gtccctgaga    600
ctcctctgcc ccgaggaca ggagactcga aaaacgctct tcctggccag tctctttgct    660
ctgtgtctgc cagcccccag catctctcct ctttcctgta agcccctctc cctgtgctga    720
ctgtcttcat agtactttag gtatgttgtc cctttacctc tgggaggata gcttgatgac    780
ctgtctgctc aggccagccc catctagagt ctcagtggcc ccagtcatgt tgagaaaggt    840
tctttcaaag atagactcaa gatagtagtg tcagaggtcc caagcaaatg aagggcgggg    900
acagttgagg gggtggaata gggacggcag cagggaacca gatagcatgc tgctgagaag    960
aaaaaaagac attggtttag gtcaggaagc aaaaaaaggg aactgagtgg ctgtgaaagg   1020
gtggggtttg ctcagactgt ccttcctctc tggactgtaa gaatatgtct ccagggccag   1080
tgtctgctgc gatcgagtcc caccttccaa gtcctggcat ctcaatgcat ctgggaagct   1140
acctgcatta agtcaggact gagcacacag gtgaactcca gaaagaagaa gctgccgccr   1200
ccauggatgg cggcagtgat tttggaatcc atcttcctga aacgcagtca gcagaagaaa   1260
aaaactagtc cgcttaactt taagaaaagg cttttcttgt tgacagtcca caagctgagt   1320
tattatgaat acgattttga aaggggaagg aggggctcca agaaagggag tatagacgtc   1380
gagaagatta catgcgttga aactgttgtg ccggagaaga atcccccgcc ggaaagacaa   1440
attcctcgac ggggcgaaga gtccagtgaa atggagcaaa tttctattat cgagcgcttc   1500
ccttacccat tccaggtagt atatgacgaa gggcccttgt acgtgttctc tccgacagaa   1560
gaactccgga aacgctggat ccatcagttg aaaaatgtaa tacgctacaa tagtgacctg   1620
gtacagaaat accaccccttg ttttttggatt gatggccaat acttgtgttg tagtcagacg   1680
gcaaagaatg caatgggttg ccaaattttg gagaatcgaa acgggagcct caagccagga   1740
agctctcatc gcaaaacaaa aaaacccttg ccaccgactc ccgaggaaga tcagatcctg   1800
aagaaacctc ttccccctga gcctgcagca gctcctgtca gcacgtccga gcttaagaaa   1860
gtggtcgcat tgtacgatta catgccgatg aacgctaacg atctgcagct gagaaaaggc   1920
gacgagtact ttatcctcga ggaatctaac ctcccgtggt ggagagcaag agataaaaac   1980
ggacaagagg ggtacatccc ctcaaattat gtgacagagg cggaggattc catcgagatg   2040
tacgagtggt attcaaagca catgactcgg agccaggccg agcaattgct taaacaggag   2100
ggaaaagaag gtggctttat agtgagggac tctagcaagg ctggaaaata cacggtgagc   2160
gtatttgcca agtctacggg agatccccaa ggggttataa ggcactacgt agtctgttca   2220
actccccaga gccagtacta tcttgcgaaa aagcacctct tctccactat tcctgagctg   2280
ataaattacc atcaacataa cagcgcgggc ctgataagca ggctcaaata cccggtctcc   2340
caacagaaca agaacgcacc ttctaccgca gggctcggtt atggctcatg ggaaattgac   2400
ccgaaagatc ttactttcct gaaggaactc ggcactggca agttcggcgt tgtaaagtac   2460
ggaaaatgga ggggacaata tgacgtcgcg ataaaaatga tcaaagaggg gtccatgagt   2520
gaggacgaat ttattgagga ggcgaaagta atgatgaatc tcagtcatga aaaactcgta   2580
caattgtatg gtgtttgcac caaacaacga ccaatttta tcataaccga gtacatggcc   2640
```

```
aacggttgtt tgcttaatta cctgagagaa atgcgacatc ggttccaaac acaacaactg    2700
cttgagatgt gtaaggatgt ctgcgaagca atggagtacc tcgaatcaaa acagttcctt    2760
cacagagatc ttgcggcgcg gaactgtctg gttaacgatc agggcgtagt taaggtcagc    2820
gactttgggc tctcacgata tgttcttgat gatgagtata ccagcagtgt tggatcaaag    2880
ttccctgtta ggtggtcacc gccagaggtt ctgatgtata gcaagttctc ttctaagagt    2940
gacatctggg ccttcggagt actcatgtgg gagatctatt ccctgggcaa gatgccttac    3000
gagagattca ccaatagcga aactgcggaa cacatcgccc aaggccttag actctatcgg    3060
ccgcacctcg cgagcgaaaa ggtctataca atcatgtact cctgttggca tgagaaagct    3120
gatgagcgcc caacgttcaa gatacttctc agtaatatcc ttgacgtaat ggatgaggaa    3180
tcctga                                                              3186

<210> SEQ ID NO 26
<211> LENGTH: 3186
<212> TYPE: DNA
<213> ORGANISM: Artificial Sequence
<220> FEATURE:
<223> OTHER INFORMATION: Synthetic

<400> SEQUENCE: 26
accccatttt ttttgtttgc ttgtttgttt gtttttttaga caaaataaag aaaaaaaaat      60
aaggtcctgt tgacttaaaa cttcggatga aattgtagtg ggacctgtga tctgtttcta     120
cattaggata cagtgccttg gggcaaggaa atatggcagt gcccgaggtg tcaaggtggg     180
caggcagatc agtcagcagg ggctccacca tcatggtctg cattcaatac tggctgcatt     240
tcctaggaga atccctgggg gaatcattgc agttggagca taatgtaggg ggcccctgag     300
aaaacctcca ggcttcaagt gacataccta gtctgcttta ccggtttaca ggactcaaga     360
gaaaggtgga cattgagagt taatccctga ggccaaatct taaatggaga aagtcaacat     420
ccacagaaaa tggggaaggg cacaagtatt tctgtgggct tatattccga cattttatc      480 tgtaggggaa aaatgctttc ttagaaaatg actcagcacg gggaagtctt gtctctacct     540
ctgtcttgtt ttgtcctttg gggtccctc actatcaagt tcaactgtgt gtccctgaga      600
ctcctctgcc ccggaggaca ggagactcga aaacgctct tcctggccag tctctttgct     660
ctgtgtctgc cagcccccag catctctcct cttcctgta agcccctctc cctgtgctga     720
ctgtcttcat agtactttag gtatgttgtc cctttacctc tgggaggata gcttgatgac     780
ctgtctgctc aggccagccc catctagagt ctcagtggcc ccagtcatgt tgagaaaggt     840
tctttcaaag atagactcaa gatagtagtg tcagaggtcc caagcaaatg aagggcgggg     900
acagttgagg gggtggaata gggacggcag cagggaacca gatagcatgc tgctgagaag     960
aaaaaaagac attggtttag gtcaggaagc aaaaaaaggg aactgagtgg ctgtgaaagg    1020
gtggggtttg ctcagactgt ccttcctctc tggactgtaa gaatatgtct ccagggccag    1080
tgtctgctgc gatcgagtcc caccttccaa gtcctggcat ctcaatgcat ctgggaagct    1140
acctgcatta agtcaggact gagcacacag gtgaactcca gaaagaagaa gctgccgccr    1200
ccauggatgg ccgctgtgat cctggagagc attttcctga agaggtccca gcagaaaaag    1260
aaaacctctc ccctgaactt taagaaaaga ctgttcctgc tgacagtgca aagctgtct     1320 tactatgagt acgactttga gcggggccgc cgaggatcaa aaaagggag catcgatgtg    1380 gagaagatta catgcgtgga gaccgtggtc cctgaaaaga tccaccccc tgagaggcag    1440 atcccaagac ggggcgagga gtcctctgag atggagcaga ttagtatcat tgagcgcttc    1500
```

```
ccctatcctt ttcaggtggt gtacgacgag ggaccactgt atgtgttctc acccacagag    1560
gagctgagaa agaggtggat tcaccagctg aagaacgtga ttagatacaa tagcgatctg    1620
gtgcagaagt atcacccttg tttttggatc gacgggcagt acctgtgctg ttcccagaca    1680
gctaagaacg ctatgggatg ccagattctg gaaaatcgga acggatctct gaaaccaggg    1740
agttcacacc gcaagaccaa aaagcccctg cctccaacac ccgaggagga tcagatcctg    1800
aaaaagcctc tgccacccga gcctgctgca gccccagtca gcacttccga actgaaaaag    1860
gtggtggctc tgtatgacta catgcccatg aatgctaacg atctgcagct gagaaagggc    1920
gacgagtatt tcattctgga agagtctaat ctgccttggt ggagggccag agataagaac    1980
ggacaggagg ggtacatccc atctaattat gtgaccgagg ctgaggactc tattgagatg    2040
tacgagtggt atagcaagca catgacacgg tcccaggctg agcagctgct gaagcaggag    2100
ggcaaagagg gagggtttat cgtgcgcgat tctagtaagg ccggcaaata cactgtgtca    2160
gtgttcgcta agagcaccgg agaccccag ggcgtgatca gacactatgt ggtgtgttcc    2220
acacctcagt ctcagtacta tctggctgag aagcacctgt ttagtacaat cccagagctg    2280
attaactacc accagcacaa ttctgccggc ctgatcagca ggctgaagta tcccgtctcc    2340
cagcagaaca aaaatgctcc ttctaccgct ggactggggt acggcagttg ggagattgat    2400
ccaaaggacc tgacattcct gaaggagctg gaactgggc agtttggcgt ggtgaagtat    2460
ggaaaatgga gagggcagta cgatgtggcc atcaagatga tcaaggaggg ctcaatgagc    2520
gaggacgagt tcatcgagga ggctaaggtc atgatgaacc tgtcccacga gaaactggtg    2580
cagctgtatg gagtgtgcac caagcagcgg cccatttta tcattacaga gtacatggct    2640
aatgggtgtc tgctgaacta tctgcgcgag atgagacaca gattccagac acagcagctg    2700
ctggaaatgt gcaaggatgt gtgtgaggct atggagtacc tggagtctaa gcagtttctg    2760
caccgggacc tggctgctcg caattgcctg gtgaacgatc agggcgtggt gaaggtgagt    2820
gacttcggac tgtcaaggta tgtgctggat gacgagtaca ccagctccgt gggctctaag    2880
tttcctgtga gatggtctcc acccgaggtg ctgatgtata gcaagttctc ctctaagagc    2940
gatatctggg cctttggcgt gctgatgtgg gaaatctaca gcctgggcaa gatgccttac    3000
gagcggttca caaattccga gacagctgag cacatcgccc agggcctgcg cctgtaccgg    3060
ccacatctgg cctctgagaa ggtgtacacc atcatgtaca gctgttggca cgagaaggcc    3120
gacgagagac ccacattcaa gatcctgctg tccaacattc tagatgtgat ggacgaggag    3180
agctga                                                               3186

<210> SEQ ID NO 27
<211> LENGTH: 2745
<212> TYPE: DNA
<213> ORGANISM: Artificial Sequence
<220> FEATURE:
<223> OTHER INFORMATION: Synthetic

<400> SEQUENCE: 27
accccatttt ttttgtttgc ttgtttgttt gttttttaga caaaataaag aaaaaaaaat      60
aaggtcctgt tgacttaaaa cttcggatga aattgtagtg ggacctgtga tctgtttcta     120
cattaggata cagtgccttg gggcaaggaa atatggcagt gcccgaggtg tcaaggtggg     180
caggcagatc agtcagcagg ggctccacca tcatggtctg cattcaatac tggctgcatt     240
tcctaggaga atccctgggg gaatcattgc agttggagca taatgtaggg ggcccctgag     300
```

```
aaaacctcca ggcttcaagt gacataccta gtctgcttta ccggtttaca ggactcaaga    360
gaaaggtgga cattgagagt taatccctga ggccaaatct taaatggaga aagtcaacat    420
ccacagaaaa tggggaaggg cacaagactc aagatagtag tgtcagaggt cccaagcaaa    480
tgaagggcgg ggacagttga gggggtggaa tagggacggc agcagggaac cagatagcat    540
gctgctgaga agaaaaaaag acattggttt aggtcaggaa gcaaaaaaag ggagactgtc    600
cttcctctct ggactgtaag aatatgtctc cagggccagt gtctgctgcg atcgagtccc    660
accttccaag tcctggcatc tcaatgcatc tgggaagcta cctgcattaa gtcaggactg    720
agcacacagg tgaactccag aaagaagaag ctgccgcccrc cauggatggc cgccgtcatc    780
ctagagagca tcttcctgaa gagatctcag caaaagaaga aaacctcccc tctgaacttc    840
aagaagcggc tgttcctgct gaccgtgcac aaactgagct actacgagta cgatttcgag    900
cggggaagaa gaggaagcaa aagggctct atcgacgtgg aaaaaatcac atgcgtggag    960
accgtggtgc ccgagaagaa ccctccacca gaacggcaga tccccagaag ggggaggaa    1020 tctagcgaga tggaacagat cagcatcatc gagaggtttc cttatccttt ccaggtggtt    1080
tacgacgaag gtcctctgta tgtgttcagc cccacagaag aactgcggaa gcgctggatc    1140
caccagctga agaacgtgat cagatacaac agcgacctgg tgcagaaata ccaccctgc    1200 ttctggatcg acggccagta cctctgctgc agccaaacag ccaagaatgc tatgggctgc    1260
cagatcctgg aaaaccgaaa cggctctctg aaacctggca gcagccatcg gaagaccaag    1320 aagccctgc ctcctacccc cgaagaggac caaatcctga gaaacctct gccacctgag    1380 ccagccgctg ctcctgtgag cacctccgag ctgaaaaagg tggtcgccct gtacgattac    1440
atgcctatga acgccaacga cctccagttg cgcaagggcg acgagtactt cattctggaa    1500
gagtccaacc tgccttggtg gcgggccaga gataagaacg gccaagaggg ctatatcccc    1560
agcaattacg tgaccgaggc cgaagattcg atcgagatgt acgagtggta cagcaagcac    1620
atgaccagaa gccaggccga gcagctgctg aagcaggagg gcaaggaagg cggcttcatc    1680
gttagagatt cttctaaagc cggcaagtac acagtgtccg tgttcgccaa gagcacaggc    1740
gatccccagg gagtcattcg gcactacgtg gtgtgtagta cccctcagag ccagtactac    1800
ctggctgaga agcacctgtt ctctacaatc cctgagctga tcaactacca ccagcacaac    1860
agcgccggcc tgatcagcag actgaaatac cccgtgagcc aacagaacaa gaacgccccc    1920
tctacagccg gcctgggata tggaagctgg gagatcgacc ccaaggacct gaccttcctg    1980
aaggaactgg gcaccggcca gtttggagtg gtcaagtacg gcaaatggag aggccagtac    2040
gatgtggcca tcaagatgat caaggagggc tctatgagcg aagatgagtt catagaggaa    2100
gcgaaagtga tgatgaatct gtctcatgag aagctggtgc agctgtacgg cgtgtgtaca    2160
aaacagagac ctatctttat tatcaccgag tacatggcta acggctgtct gctgaattac    2220
ctgcgggaaa tgagacacag attccagaca cagcaactgc tggagatgtg caaggacgtg    2280
tgcgaggcca tggaatacct ggaatccaag cagttcctgc accgggacct ggccgccaga    2340
aattgtctgg tgaacgacca gggcgtggtc aaggtgtccg acttcggcct gagcagatac    2400
gtgctggacg acgaatacac cagcagcgtg ggcagcaaat ccctgtcag atggagccct    2460 cctgaagtgc tgatgtacag caagttcagc agcaagagcg acatctgggc ctttggagtg    2520
ctgatgtggg aaatctactc tctgggcaag atgccttacg agagattcac caacagcgaa    2580
accgccgagc acatcgccca gggcctgcgg ctgtatcggc ctcacctggc cagcgagaaa    2640
gtgtacacca tcatgtatag ctgctggcac gagaaggccg acgagagacc tacctttaag    2700
```
atcctgctgt ccaacatcct ggatgtgatg gacgaggaat cctga         2745

<210> SEQ ID NO 28
<211> LENGTH: 2951
<212> TYPE: DNA
<213> ORGANISM: Artificial Sequence
<220> FEATURE:
<223> OTHER INFORMATION: Synthetic

<400> SEQUENCE: 28
gcatttccta ggagaatccc tgggggaatc attgcagttg gagcataatg tagggggccc     60
ctgagaaaac ctccaggctt caagtgacat acctagtctg ctttaccggt ttacaggact    120
caagagaaag gtggacattg agagttaatc cctgaggcca atcttaaat ggagaaagtc     180
aacatccaca gaaatggggg aagggcacaa gtatttctgt gggcttatat tccgacattt    240
ttatctgtag gggaaaaatg ctttcttaga aaatgactca gcacggggaa gtcttgtctc    300
tacctctgtc ttgttttgtc ctttgggtc ccttcactat caagttcaac tgtgtgtccc     360
tgagactcct ctgccccgga ggacaggaga ctcgaaaaac gctcttcctg ccagtctct    420
ttgctctgtg tctgccagcc cccagcatct ctcctctttc ctgtaagccc ctctccctgt    480
gctgactgtc ttcatagtac tttaggtatg ttgtcccttt acctctggga ggatagcttg    540
atgacctgtc tgctcaggcc agccccatct agagtctcag tggccccagt catgttgaga    600
aaggttcttt caaagataga ctcaagatag tagtgtcaga ggtcccaagc aaatgaaggg    660
cggggacagt tgagggggtg aataggggac ggcagcaggg aaccagatag catgctgctg    720
agaagaaaaa aagacattgg tttaggtcag gaagcaaaaa aagggaactg agtggctgtg    780
aaagggtggg gtttgctcag actgtccttc ctctctggac tgtaagaata tgtctccagg    840
gccagtgtct gctgcgatcg agtcccacct tccaagtcct ggcatctcaa tgcatctggg    900
aagctacctg cattaagtca ggactgagca cacaggtgaa ctccagaaag aagaagctgc    960
cgccrccaug gatggccgcc gtcatcctag agagcatctt cctgaagaga tctcagcaaa   1020
agaagaaaac ctcccctctg aacttcaaga agcggctgtt cctgctgacc gtgcacaaac   1080
tgagctacta cgagtacgat ttcgagcggg gaagaagagg aagcaagaag ggctctatcg   1140
acgtggaaaa aatcacatgc gtggagaccg tggtcccga agaaccct ccaccagaac       1200
ggcagatccc cagaaggggg gaggaatcta gcgagatgga acagatcagc atcatcgaga   1260
ggtttcctta ccttttccag gtggtttacg acgaaggtcc tctgtatgtg ttcagcccca   1320
cagaagaact gcggaagcgc tggatccacc agctgaagaa cgtgatcaga tacaacagcg   1380
acctggtgca gaaataccac ccctgcttct ggatcgacgg ccagtacctc tgctgcagcc   1440
aaacagccaa gaatgctatg gctgccaga tcctggaaaa ccgaaacggc tctctgaaac    1500
ctggcagcag ccatcggaag accaagaagc ccctgcctcc tacccccgaa gaggaccaaa   1560
tcctgaagaa acctctgcca cctgagccag ccgctgctcc tgtgagcacc tccgagctga   1620
aaaaggtggt cgccctgtac gattacatgc ctatgaacgc caacgacctc cagttgcgca   1680
agggcgacga gtacttcatt ctggaagagt ccaacctgcc ttggtggcgg gccagagata   1740
agaacggcca agagggctat atccccagca attacgtgac cgaggccgaa gattcgatcg   1800
agatgtacga gtggtacagc aagcacatga ccagaagcca ggccgagcag ctgctgaagc   1860
aggagggcaa ggaaggcggc ttcatcgtta gagattcttc taaagccggc aagtacacag   1920
tgtccgtgtt cgccaagagc acaggcgatc ccagggagt cattcggcac tacgtggtgt    1980

| | |
|---|---:|
| gtagtacccc tcagagccag tactacctgg ctgagaagca cctgttctct acaatccctg | 2040 |
| agctgatcaa ctaccaccag cacaacagcg ccggcctgat cagcagactg aaataccccg | 2100 |
| tgagccaaca gaacaagaac gcccctcta cagccggcct gggatatgga agctgggaga | 2160 |
| tcgaccccaa ggacctgacc ttcctgaagg aactgggcac cggccagttt ggagtggtca | 2220 |
| agtacggcaa atggagaggc cagtacgatg tggccatcaa gatgatcaag gagggctcta | 2280 |
| tgagcgaaga tgagttcata gaggaagcga agtgatgat gaatctgtct catgagaagc | 2340 |
| tggtgcagct gtacggcgtg tgtacaaaac agagacctat ctttattatc accgagtaca | 2400 |
| tggctaacgg ctgtctgctg aattacctgc gggaaatgag acacagattc cagacacagc | 2460 |
| aactgctgga gatgtgcaag gacgtgtgcg aggccatgga atacctggaa tccaagcagt | 2520 |
| tcctgcaccg ggacctggcc gccagaaatt gtctggtgaa cgaccaggc gtggtcaagg | 2580 |
| tgtccgactt cggcctgagc agatacgtgc tggacgacga atacaccagc agcgtgggca | 2640 |
| gcaaattccc tgtcagatgg agccctcctg aagtgctgat gtacagcaag ttcagcagca | 2700 |
| agagcgacat ctgggccttt ggagtgctga tgtgggaaat ctactctctg gcaagatgc | 2760 |
| cttacgagag attcaccaac agcgaaaccg ccgagcacat cgcccagggc ctgcggctgt | 2820 |
| atcggcctca cctggccagc gagaaagtgt acaccatcat gtatagctgc tggcacgaga | 2880 |
| aggccgacga gagacctacc tttaagatcc tgctgtccaa catcctggat gtgatggacg | 2940 |
| aggaatcctg a | 2951 |

<210> SEQ ID NO 29
<211> LENGTH: 3686
<212> TYPE: DNA
<213> ORGANISM: Artificial Sequence
<220> FEATURE:
<223> OTHER INFORMATION: Synthetic

<400> SEQUENCE: 29

| | |
|---|---:|
| caaatgtgag tatcaaccac tctatcatca gtctacaaat actttaaatg tttttattta | 60 |
| aagtcctgtt gatggctggg agaggtggct cactcctgta atccctgcat tttgggaggc | 120 |
| caaggcagga gtatcgcttg agcccaggag tttgagacca gcctgggcaa catagtgaaa | 180 |
| ccccatctct acaaaaagta gaaaaattag cccagcacag tgatgtgtgc ctatagtccc | 240 |
| aggtactagg gtgactgagg tgagaggatc acttgagccc aggaggtgga ggctgcagtg | 300 |
| agccatgatc acgccactgc actccaacct gggcttcaga gcaagaccct gtctcaaaaa | 360 |
| aaaaaaaaaa aaaaaaaggt cccagggcct gttgggggctt gggggtgagg ggagggatct | 420 |
| tagaggatgg gtcaataggt gcagcaaatc accatgtcac acatataccct atgtaacaaa | 480 |
| cttgcaccctt ctgcacatat accccatttt ttttgtttgc ttgtttgttt gttttttaga | 540 |
| caaaataaag aaaaaaaat aaggtcctgt tgacttaaaa cttcggatga aattgtagtg | 600 |
| ggacctgtga tctgtttcta cattaggata cagtgcttg gggcaaggaa atatggcagt | 660 |
| gcccgaggtg tcaaggtggg caggcagatc agtcagcagg ggctccacca tcatggtctg | 720 |
| cattcaatac tggctgcatt tcctaggaga atccctgggg gaatcattgc agttggagca | 780 |
| taatgtaggg ggcccctgag aaaacctcca ggcttcaagt gacataccta gtctgcttta | 840 |
| ccggtttaca ggactcaaga gaaaggtgga cattgagagt taatccctga ggccaaatct | 900 |
| taaatggaga aagtcaacat ccacagaaaa tggggaaggg cacaagtatt tctgtgggct | 960 |
| tatattccga cattttttatc tgtaggggaa aaatgctttc ttagaaaatg actcagcacg | 1020 |
| gggaagtctt gtctctacct ctgtcttgtt ttgtcctttg gggtcccttc actatcaagt | 1080 |

```
tcaactgtgt gtccctgaga ctcctctgcc ccggaggaca ggagactcga aaaacgctct    1140
tcctggccag tctctttgct ctgtgtctgc cagcccccag catctctcct ctttcctgta    1200
agcccctctc cctgtgctga ctgtcttcat agtactttag gtatgttgtc cctttacctc    1260
tgggaggata gcttgatgac ctgtctgctc aggccagccc catctagagt ctcagtggcc    1320
ccagtcatgt tgagaaaggt tctttcaaag atagactcaa gatagtagtg tcagaggtcc    1380
caagcaaatg aagggcgggg acagttgagg ggtggaata gggacggcag cagggaacca    1440
gatagcatgc tgctgagaag aaaaaaagac attggtttag gtcaggaagc aaaaaaaggg    1500
aactgagtgg ctgtgaaagg gtggggtttg ctcagactgt ccttcctctc tggactgtaa    1560
gaatatgtct ccagggccag tgtctgctgc gatcgagtcc caccttccaa gtcctggcat    1620
ctcaatgcat ctgggaagct acctgcatta agtcaggact gagcacacag gtgaactcca    1680
gaaagaagaa gctgccgccr ccauggatgg ccgccgtcat cctagagagc atcttcctga    1740 agatctca gcaaaagaag aaaacctccc ctctgaactt caagaagcgg ctgttcctgc    1800
tgaccgtgca caaactgagc tactacgagt acgatttcga gcggggaaga gaggaagca    1860 agaagggctc tatcgacgtg gaaaaaatca catgcgtgga gaccgtggtg cccgagaaga    1920
accctccacc agaacggcag atccccagaa gggggaggga atctagcgag atggaacaga    1980
tcagcatcat cgagaggttt ccttatcctt ccaggtggt ttacgacgaa ggtcctctgt    2040
atgtgttcag ccccacagaa gaactgcgga agcgctggat ccaccagctg aagaacgtga    2100
tcagatacaa cagcgacctg gtgcagaaat accacccctg cttctggatc gacggccagt    2160
acctctgctg cagccaaaca gccaagaatg ctatgggctg ccagatcctg gaaaaccgaa    2220
acggctctct gaaacctggc agcagccatc ggaagaccaa gaagcccctg cctcctaccc    2280
ccgaagagga ccaaatcctg aagaaacctc tgccacctga gccagcgct gctcctgtga    2340 gcacctccga gctgaaaaag gtggtcgccc tgtacgatta catgcctatg aacgccaacg    2400
acctccagtt gcgcaagggc gacgagtact tcattctgga gagtccaac ctgccttggt    2460 ggcgggccag agataagaac ggccaagagg gctatatccc cagcaattac gtgaccgagg    2520
ccgaagattc gatcgagatg tacgagtggt acagcaagca catgaccaga agccaggccg    2580
agcagctgct gaagcaggag ggcaaggaag gcggcttcat cgttagagat tcttctaaag    2640
ccggcaagta cacagtgtcc gtgttcgcca agagcacagg cgatcccag ggagtcattc    2700 ggcactacgt ggtgtgtagt accccctcaga gccagtacta cctggctgag aagcacctgt    2760
tctctacaat ccctgagctg atcaactacc accagcacaa cagcgccggc ctgatcagca    2820
gactgaaata ccccgtgagc caacagaaca gaacgcccc ctctacagcc ggcctgggat    2880
atggaagctg gagatcgac cccaaggacc tgaccttcct gaaggaactg gcaccggcc    2940 agtttggagt ggtcaagtac ggcaaatgga gaggccagta cgatgtggcc atcaagatga    3000
tcaaggaggg ctctatgagc gaagatgagt tcatagagga agcgaaagtg atgatgaatc    3060
tgtctcatga gaagctggtg cagctgtacg gcgtgtgtac aaaacagaga cctatcttta    3120
ttatcaccga gtacatggct aacggctgtc tgctgaatta cctgcgggaa atgagacaca    3180
gattccagac acagcaactg ctggagatgt gcaaggacgt gtgcgaggcc atggaatacc    3240
tggaatccaa gcagttcctg caccgggacc tggccgccag aaattgtctg gtgaacgacc    3300
agggcgtggt caaggtgtcc gacttcggcc tgagcagata cgtgctggac gacgaataca    3360
ccagcagcgt gggcagcaaa ttccctgtca gatggagccc tcctgaagtg ctgatgtaca    3420
```

| | |
|---|---|
| gcaagttcag cagcaagagc gacatctggg cctttggagt gctgatgtgg gaaatctact | 3480 |
| ctctgggcaa gatgccttac gagagattca ccaacagcga aaccgccgag cacatcgccc | 3540 |
| agggcctgcg gctgtatcgg cctcacctgg ccagcgagaa agtgtacacc atcatgtata | 3600 |
| gctgctggca cgagaaggcc gacgagagac ctacctttaa gatcctgctg tccaacatcc | 3660 |
| tggatgtgat ggacgaggaa tcctga | 3686 |

<210> SEQ ID NO 30
<211> LENGTH: 3057
<212> TYPE: DNA
<213> ORGANISM: Artificial Sequence
<220> FEATURE:
<223> OTHER INFORMATION: Synthetic

<400> SEQUENCE: 30

| | |
|---|---|
| accccatttt ttttgtttgc ttgtttgttt gttttttaga caaaataaag aaaaaaaaat | 60 |
| aaggtcctgt tgacttaaaa cttcggatga aattgtagtg ggacctgtga tctgtttcta | 120 |
| cattaggata cagtgccttg gggcaaggaa atatggcagt gcccgaggtg tcaaggtggg | 180 |
| caggcagatc agtcagcagg ggctccacca tcatggtctg cattcaatac tggctgcatt | 240 |
| tcctaggaga atccctgggg gaatcattgc agttggagca taatgtaggg ggcccctgag | 300 |
| aaaacctcca ggcttcaagt gacataccta gtctgcttta ccggtttaca ggactcaaga | 360 |
| gaaaggtgga cattgagagt taatccctga ggccaaatct taaatggaga aagtcaacat | 420 |
| ccacagaaaa tggggaaggg cacaagtatt tctgtgggct tatattccga cattttatc | 480 |
| tgtaggggaa aaatgctttc ttagaaaatg actcagcacg gggaagtctt gtctctacct | 540 |
| ctgtcttgtt ttgtcctttg gggtcccttc actatcaagt tcaactgtgt gtccctgaga | 600 |
| ctcctctgcc ccgaggacaa ggagactcga aaacgctct tcctggccag tctctttgct | 660 |
| ctgtgtctgc cagcccccag catctctcct cttttcctgta agcccctctc cctgtgctga | 720 |
| ctgtcttcat agtactttag gtatgttgtc ccttttacctc tgggaggata gcttgatgac | 780 |
| ctgtctgctc aggccagccc catctagagt tcagtggcc ccagtcatgt tgagaaaggt | 840 |
| tctttcaaag atagactcaa gatagtagtg tcagaggtcc caagcaaatg aagggcgggg | 900 |
| acagttgagg gggtggaata gggacggcag cagggaacca gatagcatgc tgctgagaag | 960 |
| aaaaaaagac attggtttag gtcaggaagc aaaaaagggg aactgagtgg ctgtgaaagg | 1020 |
| gtggggtttg ctcagactgt ccttcctctc tggactgtaa gaatgccgcc rccauggatg | 1080 |
| gccgccgtca tcctagagag catcttcctg aagagatctc agcaaaagaa gaaaacctcc | 1140 |
| cctctgaact tcaagaagcg gctgttcctg ctgaccgtgc acaaactgag ctactacgag | 1200 |
| tacgatttcg agcggggaag aagaggaagc aagaagggct ctatcgacgt ggaaaaaatc | 1260 |
| acatgcgtgg agaccgtggt gcccgagaag aaccctccac cagaacggca gatccccaga | 1320 |
| agggggggag aatctagcga gatggaacag atcagcatca tcgagaggtt tccttatcct | 1380 |
| ttccaggtgg tttacgacga aggtcctctg tatgtgttca gccccacaga gaactgcgg | 1440 |
| aagcgctgga tccaccagct gaagaacgtg atcagataca acagcgacct ggtgcagaaa | 1500 |
| taccaccccct gcttctggat cgacggccag tacctctgct gcagccaaac agccaagaat | 1560 |
| gctatgggct gccagatcct ggaaaaccga aacggctctc tgaaacctgg cagcagccat | 1620 |
| cggaagacca agaagcccct gcctcctacc cccgaagagg accaaatcct gaagaaacct | 1680 |
| ctgccacctg agccagccgc tgctcctgtg agcacctccg agctgaaaaa ggtggtcgcc | 1740 |
| ctgtacgatt acatgcctat gaacgccaac gacctccagt tgcgcaaggg cgacgagtac | 1800 |

```
ttcattctgg aagagtccaa cctgccttgg tggcgggcca gagataagaa cggccaagag    1860
ggctatatcc ccagcaatta cgtgaccgag gccgaagatt cgatcgagat gtacgagtgg    1920
tacagcaagc acatgaccag aagccaggcc gagcagctgc tgaagcagga gggcaaggaa    1980
ggcggcttca tcgttagaga ttcttctaaa gccggcaagt acacagtgtc cgtgttcgcc    2040
aagagcacag gcgatcccca gggagtcatt cggcactacg tggtgtgtag taccccctcag   2100 agccagtact acctggctga gaagcacctg ttctctacaa tccctgagct gatcaactac    2160
caccagcaca acagcgccgg cctgatcagc agactgaaat accccgtgag ccaacagaac    2220
aagaacgccc cctctacagc cggcctggga tatggaagct gggagatcga ccccaaggac    2280
ctgaccttcc tgaaggaact gggcaccggc cagtttggag tggtcaagta cggcaaatgg    2340
agaggccagt acgatgtggc catcaagatg atcaaggagg gctctatgag cgaagatgag    2400
ttcatagagg aagcgaaagt gatgatgaat ctgtctcatg agaagctggt gcagctgtac    2460
ggcgtgtgta caaaacagag acctatcttt attatcaccg agtacatggc taacggctgt    2520
ctgctgaatt acctgcggga aatgagacac agattccaga cacagcaact gctggagatg    2580
tgcaaggacg tgtgcgaggc catggaatac ctggaatcca agcagttcct gcaccgggac    2640
ctggccgcca gaaattgtct ggtgaacgac cagggcgtgg tcaaggtgtc cgacttcggc    2700
ctgagcagat acgtgctgga cgacgaatac accagcagcg tgggcagcaa attccctgtc    2760
agatggagcc ctcctgaagt gctgatgtac agcaagttca gcagcaagag cgacatctgg    2820
gcctttggag tgctgatgtg ggaaatctac tctctgggca gatgccttta cgagagattc    2880
accaacagcg aaaccgccga gcacatcgcc cagggcctgc ggctgtatcg gcctcacctg    2940
gccagcgaga agtgtacac catcatgtat agctgctggc acgagaaggc cgacgagaga    3000 cctacctttta agatcctgct gtccaacatc ctggatgtga tggacgagga atcctga      3057
```

<210> SEQ ID NO 31
<211> LENGTH: 3500
<212> TYPE: DNA
<213> ORGANISM: Artificial Sequence
<220> FEATURE:
<223> OTHER INFORMATION: Synthetic

<400> SEQUENCE: 31

```
cgcaaacacc cgaatcaact tctagtcaaa ttattgttca cgccgcaatg acccaccccct    60 ggcccgcgtc tgtggaactg acccctggtg tacaggagag ttcgctgctg aaagtggtcc    120 caaagggta ctagttttta agctcccaac tcccccctccc ccagcgtctg gaggattcca    180
caccctcgca ccgcaggggc gaggaagtgg gcggagtccg gttttggcgc cagccgctga    240
ggctgccaag cagaaaagcc accgctgagg agactccggt cactgtcctc gccccgcctc    300 cccccttccct cccccttgggg accaccgggc gccacgccgc gaacggtaag tgccgcggtc    360
gtcggcgcct ccgccctccc cctagggccc caattcccag cggggcgcggc gcgcggcccc    420 tcccccccgcc gggcgcgcgc ccgctgcccc gcccttcgtg gccgcccggc gtgggcggtg    480 ccaccccctcc ccccagcggc cccgcgcgca gctcccggct ccctcccccct tcggatgtgg    540 cttgagctgt aggcgcggag ggccggagac gctgcagacc cgcgacccgg agcagctcgg    600
aggcggtgaa gtcggtggct ttccttctct ctagctctcg ctcgctggtg gtgcttcaga    660
tgccacacgc atttcctagg agaatccctg ggggaatcat tgcagttgga gcataatgta    720 ggggggcccct gagaaaacct ccaggcttca agtgacatac ctagtctgct ttaccggttt    780
```

```
acaggactca agagaaaggt ggacattgag agttaatccc tgaggccaaa tcttaaatgg      840
agaaagtcaa catccacaga aaatgggaa gggcacaagt atttctgtgg gcttatattc       900
cgacatttt  atctgtaggg gaaaaatgct ttcttagaaa atgactcagc acggggaagt      960
cttgtctcta cctctgtctt gttttgtcct ttggggtccc ttcactatca agttcaactg     1020
tgtgtccctg agactcctct gccccggagg acaggagact cgaaaaacgc tcttcctggc     1080
cagtctcttt gctctgtgtc tgccagcccc cagcatctct cctctttcct gtaagcccct     1140
ctccctgtgc tgactgtctt catagtactt taggtatgtt gtccctttac ctctgggagg     1200
atagcttgat gacctgtctg ctcaggccag ccccatctag agtctcagtg gccccagtca     1260
tgttgagaaa ggttctttca agatagact caagatagta gtgtcagagg tcccaagcaa      1320
atgaagggcg gggacagttg aggggtgga atagggacgg cagcagggaa ccagatagca      1380
tgctgctgag aagaaaaaaa gacattggtt taggtcagga agcaaaaaaa gggaactgag     1440
tggctgtgaa agggtggggt ttgctcagac tgtccttcct ctctggactg taagaattag     1500
tctcgaggcc gccrccaugg atggccgctg tgatcctgga gagcattttc ctgaagaggt     1560
cccagcagaa aaagaaaacc tctcccctga actttaagaa aagactgttc ctgctgacag     1620
tgcacaagct gtcttactat gagtacgact ttgagcgggg ccgccgagga tcaaaaaagg     1680
ggagcatcga tgtggagaag attacatgcg tggagaccgt ggtccctgaa aagaatccac     1740
cccctgagag gcagatccca agacggggcg aggagtcctc tgagatggag cagattagta     1800
tcattgagcg cttcccctat ccttttcagg tggtgtacga cgagggacca ctgtatgtgt     1860
tctcacccac agaggagctg agaaagaggt ggattcacca gctgaagaac gtgattagat     1920
acaatagcga tctggtgcag aagtatcacc cttgttttg gatcgacggg cagtacctgt      1980
gctgttccca gacagctaag aacgctatgg gatgccagat tctggaaaat cggaacggat     2040
ctctgaaacc agggagttca caccgcaaga ccaaaaagcc cctgcctcca cacccgagg      2100
aggatcagat cctgaaaaag cctctgccac ccgagcctgc tgcagcccca gtcagcactt     2160
ccgaactgaa aaaggtggtg gctctgtatg actacatgcc catgaatgct aacgatctgc     2220
agctgagaaa gggcgacgag tatttcattc tggaagagtc taatctgcct tggtggaggg     2280
ccagagataa gaacggacag gaggggtaca tcccatctaa ttatgtgacc gaggctgagg     2340
actctattga gatgtacgag tggtatagca agcacatgac acggtcccag gctgagcagc     2400
tgctgaagca ggagggcaaa gagggagggt ttatcgtgcg cgattctagt aaggccggca     2460
aatacactgt gtcagtgttc gctaagcaga ccggagaccc ccagggcgtg atcagacact     2520
atgtggtgtg ttccacacct cagtctcagt actatctggc tgagaagcac ctgtttagta     2580
caatcccaga gctgattaac taccaccagc acaattctgc cggcctgatc agcaggctga     2640
agtatcccgt ctcccagcag aacaaaaatg ctccttctac cgctggactg gggtacggca     2700
gttgggagat tgatccaaag gacctgacat tcctgaagga gctgggaact gggcagtttg     2760
gcgtggtgaa gtatgaaaaa tggagagggc agtacgatgt ggccatcaag atgatcaagg     2820
agggctcaat gagcgaggac gagttcatcg aggaggctaa ggtcatgatg aacctgtccc     2880
acgagaaact ggtgcagctg tatggagtgt gcaccaagca gcggcccatt tttatcatta     2940
cagagtacat ggctaatggg tgtctgctga actatctgcg cgagatgaga cacagattcc     3000
agacacagca gctgctggaa atgtgcaagg atgtgtgtga ggctatggag tacctggagt     3060
ctaagcagtt tctgcaccgg gacctggctg ctcgcaattg cctggtgaac gatcagggcg     3120
tggtgaaggt gagtgacttc ggactgtcaa ggtatgtgct ggatgacgag tacaccagct     3180
```

```
ccgtgggctc taagtttcct gtgagatggt ctccacccga ggtgctgatg tatagcaagt    3240
tctcctctaa gagcgatatc tgggcctttg gcgtgctgat gtgggaaatc tacagcctgg    3300
gcaagatgcc ttacgagcgg ttcacaaatt ccgagacagc tgagcacatc gcccagggcc    3360
tgcgcctgta ccggccacat ctggcctctg agaaggtgta caccatcatg tacagctgtt    3420
ggcacgagaa ggccgacgag agacccacat tcaagatcct gctgtccaac attctagatg    3480
tgatggacga ggagagctga                                                3500
```

<210> SEQ ID NO 32
<211> LENGTH: 3186
<212> TYPE: DNA
<213> ORGANISM: Artificial Sequence
<220> FEATURE:
<223> OTHER INFORMATION: Synthetic

<400> SEQUENCE: 32

```
accccatttt ttttgtttgc ttgtttgttt gttttttaga caaaataaag aaaaaaaaat      60
aaggtcctgt tgacttaaaa cttcggatga aattgtagtg ggacctgtga tctgtttcta     120
cattaggata cagtgccttg ggcaaggaaa atatggcagt gcccgaggtg tcaaggtggg     180
caggcagatc agtcagcagg ggctccacca tcatggtctg cattcaatac tggctgcatt     240
tcctaggaga atccctgggg gaatcattgc agttggagca taatgtaggg ggcccctgag     300
aaaacctcca ggcttcaagt gacatcccta gtctgcttta ccggtttaca ggactcaaga     360
gaaaggtgga cattgagagt taatccctga ggccaaatct taaatggaga aagtcaacat     420
ccacagaaaa tggggaaggg cacaagtatt tctgtgggct tatattccga cattttatc      480 tgtaggggaa aaatgctttc ttagaaaatg actcagcacg gggaagtctt gtctctacct     540
ctgtcttgtt ttgtcctttg gggtcccttc actatcaagt tcaactgtgt gtccctgaga     600
ctcctctgcc ccggaggaca ggagactcga aaaacgctct tcctggccag tctctttgct     660
ctgtgtctgc cagcccccag catctctcct cttttcctgta agcccctctc cctgtgctga    720
ctgtcttcat agtactttag gtatgttgtc ccttttacctc tgggaggata gcttgatgac    780
ctgtctgctc aggccagccc catctagagt ctcagtggcc ccagtcatgt tgagaaaggt    840
tctttcaaag atagactcaa gatagtagtg tcagaggtcc caagcaaatg aagggcgggg    900
acagttgagg gggtggaata gggacggcag cagggaacca gatagcatgc tgctgagaag    960
aaaaaaagac attggtttag gtcaggaagc aaaaaaaggg aactgagtgg ctgtgaaagg   1020 gtgggtttg ctcagactgt ccttcctctc tcaactgtaa caatatgtct ccagggccag    1080
tgtctgctgc gatcgagtcc caccttccaa gtcctggcat ctcaatgcat ctggcaagct   1140
acctgcaata agtcaccact gagcacacac aacaactcca caaacaacaa gctgccgccr   1200
ccauggatgg ccgccgtcat cctagagagc atcttcctga agagatctca gcaaagaag    1260 aaaacctccc ctctgaactt caagaagcgg ctgttcctgc tgaccgtgca caactgagc    1320 tactacgagt acgatttcga gcggggaaga agaggaagca agaagggctc tatcgacgtg   1380
gaaaaaatca catgcgtgga gaccgtggtg cccgagaaga accctccacc agaacggcag   1440
atccccagaa gggggagga atctagcgag atggaacaga tcagcatcat cgagaggttt   1500
ccttatcctt tccaggtggt ttacgacgaa ggtcctctgt atgtgttcag ccccacagaa   1560
gaactgcgga agcgctggat ccaccagctg aagaacgtga tcagatacaa cagcgacctg   1620
gtgcagaaat accaccccctg cttctggatc gacggccagt acctctgctg cagccaaaca   1680
```

```
gccaagaatg ctatgggctg ccagatcctg gaaaaccgaa acggctctct gaaacctggc   1740
agcagccatc ggaagaccaa gaagcccctg cctcctaccc ccgaagagga ccaaatcctg   1800
aagaaacctc tgccacctga gccagccgct gctcctgtga gcacctccga gctgaaaaag   1860
gtggtcgccc tgtacgatta catgcctatg aacgccaacg acctccagtt gcgcaagggc   1920
gacgagtact tcattctgga agagtccaac ctgccttggt ggcgggccag agataagaac   1980
ggccaagagg gctatatccc cagcaattac gtgaccgagg ccgaagattc gatcgagatg   2040
tacgagtggt acagcaagca catgaccaga agccaggccg agcagctgct gaagcaggag   2100
ggcaaggaag gcggcttcat cgttagagat tcttctaaag ccggcaagta cacagtgtcc   2160
gtgttcgcca agagcacagg cgatccccag ggagtcattc ggcactacgt ggtgtgtagt   2220 accccctcaga gccagtacta cctggctgag aagcacctgt tctctacaat ccctgagctg   2280
atcaactacc accagcacaa cagcgccggc ctgatcagca gactgaaata ccccgtgagc   2340
caacagaaca gaacgcccc ctctacagcc ggcctgggat atggaagctg ggagatcgac   2400
cccaaggacc tgaccttcct gaaggaactg ggcaccggcc agtttggagt ggtcaagtac   2460
ggcaaatgga gaggccagta cgatgtggcc atcaagatga tcaaggaggg ctctatgagc   2520
gaagatgagt tcatagagga agcgaaagtg atgatgaatc tgtctcatga aagctggtg    2580 cagctgtacg gcgtgtgtac aaaacagaga cctatcttta ttatcaccga gtacatggct   2640
aacggctgtc tgctgaatta cctgcgggaa atgagacaca gattccagac acagcaactg   2700
ctggagatgt gcaaggacgt gtgcgaggcc atggaatacc tggaatccaa gcagttcctg   2760
caccgggacc tggccgccag aaattgtctg gtgaacgacc agggcgtggt caaggtgtcc   2820
gacttcggcc tgagcagata cgtgctggac gacgaataca ccagcagcgt gggcagcaaa   2880
ttccctgtca gatggagccc tcctgaagtg ctgatgtaca gcaagttcag cagcaagagc   2940
gacatctggg cctttggagt gctgatgtgg gaaatctact ctctgggcaa gatgcctac    3000 gagagattca ccaacagcga aaccgccgag cacatcgccc agggcctgcg gctgtatcgg   3060
cctcacctgg ccagcgagaa agtgtacacc atcatgtata gctgctggca cgagaaggcc   3120
gacgagagac ctaccttttaa gatcctgctg tccaacatcc tggatgtgat ggacgaggaa   3180
tcctga                                                              3186
```

<210> SEQ ID NO 33
<211> LENGTH: 3186
<212> TYPE: DNA
<213> ORGANISM: Artificial Sequence
<220> FEATURE:
<223> OTHER INFORMATION: Synthetic

<400> SEQUENCE: 33

```
acccccatttt ttttgtttgc ttgtttgttt gttttttaga caaaataaag aaaaaaaaat    60
aaggtcctgt tgacttaaaa cttcggatga aattgtagtg ggacctgtga tctgtttcta   120
cattaggata cagtgccttg gggcaaggaa atatggcagt gcccgaggtg tcaaggtggg   180
caggcagatc agtcagcagg ggctccacca tcatggtctg cattcaatac tggctgcatt   240
tcctaggaga atccctgggg gaatcattgc agttggagca taatgtaggg ggcccctgag   300
aaaacctcca ggcttcaagt gacatacctga gtctgcttta ccggtttaca ggactcaaga   360
gaaaggtgga cattgagagt taatccctga ggccaaatct taaatggaga aagtcaacat   420
ccacagaaaa tggggaaggg cacaagtatt tctgtgggct tatattccga catttttatc   480
tgtaggggaa aaatgctttc ttagaaaatg actcagcacg gggaagtctt gtctctacct   540
```

```
ctgtcttgtt ttgtcctttg gggtcccttc actatcaagt tcaactgtgt gtccctgaga    600
ctcctctgcc ccggaggaca ggagactcga aaaacgctct tcctggccag tctctttgct    660
ctgtgtctgc cagcccccag catctctcct ctttcctgta agcccctctc cctgtgctga    720
ctgtcttcat agtactttag gtatgttgtc ccttttacctc tgggaggata gcttgatgac    780
ctgtctgctc aggccagccc catctagagt ctcagtggcc ccagtcatgt tgagaaaggt    840
tctttcaaag atagactcaa gatagtagtg tcagaggtcc caagcaaatg aagggcgggg    900
acagttgagg gggtggaata gggacggcag cagggaacca gatagcatgc tgctgagaag    960
aaaaaaagac attggtttag gtcaggaagc aaaaaaaggg aactgagtgg ctgtgaaagg   1020
gtggggtttg ctcagactgt ccttcctctc tggactgtaa gaatatgtct ccagggccag   1080
tgtctgctgc gatcgagtcc caccttccaa gtcctggcat ctcaatgcat ctgggaagct   1140
acctgcatta agtcaggact gagcacacag gtgaactcca gaaagaagaa gctgccgccr   1200
ccauggatgg ccgcagtgat tctggagagc atctttctga agcggtccca gcagaaaaag   1260
aaaacaagcc ctctgaactt caagaagcgg ctgtttctcc tgaccgtgca caaactctcc   1320
tactacgagt acgactttga acgggggcgg cggggcagca agaagggcag catcgatgtg   1380
gagaagatca cctgcgtgga aacagtggtg cctgaaaaga tcctcctcc agaacggcag   1440
attccccggc ggggcgaaga gtccagcgaa atggagcaga ttagcatcat tgaacggttc   1500
ccttacccct tccaggtggt gtacgatgaa gggcctctct acgtcttctc cccaaccgaa   1560
gaactgcgga gcggtggat tcaccagctc aaaaacgtga tccggtacaa cagcgatctg   1620
gtgcagaaat accacccttg cttctggatc gatgggcagt acctctgctg ctctcagaca   1680
gccaaaaatg ctatgggctg ccagattctg gagaaccgga atggaagcct gaaacctggg   1740
agctctcacc ggaagacaaa gaagcctctg ccccaaccc tgaggagga ccagatcctg    1800
aaaaagccac tgcccctga gccagcagca gcaccagtct ccacaagcga gctgaaaaag   1860
gtggtggccc tgtacgatta catgccaatg aatgcaaatg atctgcagct gcggaagggc   1920
gatgaatact ttatcctgga ggaaagcaac ctgccatggt ggcgggcacg ggataaaaat   1980
gggcaggaag gctacattcc tagcaactac gtcaccgaag cagaagactc catcgaaatg   2040
tacgagtggt actccaaaca catgacccgg agccaggctg agcagctgct gaagcaggag   2100
gggaaagaag gaggcttcat tgtccgggac tccagcaaag ctggcaaata cacagtgtct   2160
gtctttgcta aatccacagg ggaccctcag gggtaatcc ggcactacgt ggtgtgctcc   2220
acacctcaga gccagtacta cctggctgag aagcacctgt tcagcaccat ccctgagctc   2280
attaactacc accagcacaa ctctgcagga ctcatctccc ggctcaaata cccagtgtct   2340
cagcagaaca agaatgcacc ttccaccgca ggcctgggat acggaagctg ggaaattgat   2400
ccaaaggacc tgaccttcct gaaggagctg gggaccggac agtttgggt ggtgaagtac   2460
gggaaatggc ggggccagta cgacgtggcc atcaagatga tcaaagaagg ctccatgtct   2520
gaagatgaat tcattgaaga agccaaagtc atgatgaatc tgtcccacga aagctggtg   2580
cagctgtacg gcgtctgcac caagcagcgg cccatcttca tcatcaccga gtacatggcc   2640
aatggctgcc tcctgaacta cctgcgggag atgcggcacc ggttccagac ccagcagctg   2700
ctggagatgt gcaaggatgt ctgcgaagcc atggaatacc tggagagcaa gcagttcctg   2760
caccgggacc tggcagctcg gaactgcctg gtgaacgatc agggagtggt gaaagtgtct   2820
gatttcggcc tgtcccggta cgtcctggat gatgaataca caagcagcgt gggctccaaa   2880
```

```
tttccagtcc ggtggtcccc acccgaagtc ctgatgtaca gcaagttcag cagcaaatct    2940
gacatttggg cttttggggt gctgatgtgg gaaatctatt ccctggggaa gatgccatac    3000
gagcggttta ccaacagcga daccgctgaa cacattgccc agggcctgcg gctctaccgg    3060
cctcacctgg ctagcgagaa ggtgtacacc atcatgtaca gctgctggca cgagaaagca    3120
gatgagcggc ccaccttcaa aattctgctg agcaatattc tggatgtcat ggatgaagaa    3180
tcctga                                                                3186
```

<210> SEQ ID NO 34
<211> LENGTH: 9
<212> TYPE: DNA
<213> ORGANISM: Artificial Sequence
<220> FEATURE:
<223> OTHER INFORMATION: Synthetic

<400> SEQUENCE: 34

```
gccrccaug                                                                9
```

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35

```
agcacgagat aaaaatgggc ag                                                22
```

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36

```
actccgagtc atgtgtttgg aa                                                22
```

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37

```
cagatcctgg aaaaccgaaa                                                   20
```

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38

```
aggtggcaga ggtttcttca                                                   20
```

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
tggattacat caaagcactg aatag                                          25

<210> SEQ ID NO 40
<211> LENGTH: 25
<212> TYPE: DNA
<213> ORGANISM: Artificial Sequence
<220> FEATURE:
<223> OTHER INFORMATION: Synthetic

<400> SEQUENCE: 40
ctttccagtt aaagttgaga gatca                                          25

<210> SEQ ID NO 41
<211> LENGTH: 17
<212> TYPE: DNA
<213> ORGANISM: Artificial Sequence
<220> FEATURE:
<223> OTHER INFORMATION: Synthetic

<400> SEQUENCE: 41
tctcgacgca ggactcg                                                   17

<210> SEQ ID NO 42
<211> LENGTH: 18
<212> TYPE: DNA
<213> ORGANISM: Artificial Sequence
<220> FEATURE:
<223> OTHER INFORMATION: Synthetic

<400> SEQUENCE: 42
tactgacgct ctcgcacc                                                  18

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
tttggcgtac tcaccagtcg cc                                             22

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ttgtgtctcc agtctgcttg                                                20

<210> SEQ ID NO 45
<211> LENGTH: 17
<212> TYPE: DNA
<213> ORGANISM: Artificial Sequence
<220> FEATURE:
<223> OTHER INFORMATION: Synthetic

<400> SEQUENCE: 45
aggtggtggt ggtggta                                                   17

<210> SEQ ID NO 46

```
<211> LENGTH: 26
<212> TYPE: DNA
<213> ORGANISM: Artificial Sequence
<220> FEATURE:
<223> OTHER INFORMATION: Synthetic

<400> SEQUENCE: 46
ccctctcctg gctctaaatg ttgtgt                                              26
```

LENTIVIRAL VECTORS FOR THERAPEUTIC EXPRESSION OF BTK IN HAEMATOPOIETIC CELLS

CROSS-REFERENCE TO RELATED APPLICATIONS

This application claims the benefit of priority of U.S. Provisional Patent Application No. 63/122,017, titled "LENTIVIRAL VECTORS FOR THERAPEUTIC EXPRESSION OF BTK IN HAEMATOPOIETIC CELLS", filed Dec. 7, 2020, and of U.S. Provisional Patent Application No. 63/147,956, titled "LENTIVIRAL VECTORS FOR THERAPEUTIC EXPRESSION OF BTK IN HAEMATOPOIETIC CELLS", filed Feb. 10, 2021, the contents of both applications are incorporated herein by reference in their entirety.

FIELD OF THE INVENTION

The present invention is directed to optimized BTK lentiviral vectors and their use in gene therapy of X-linked agammaglobulinemia.

BACKGROUND OF THE INVENTION

X-linked agammaglobulinemia (XLA) is a primary immunodeficiency resulting from mutations in the Bruton's tyrosine kinase (BTK) gene. These mutations lead to the failure of afflicted individuals to generate mature B cells as well as other immunological dysfunctions such as in NK and myeloid cells. Current therapy has not changed for over 5 decades and consists of immunoglobulin replacement and targeted antimicrobial agents. This therapy is insufficient and treated XLA patients continue to suffer from low quality of life and recurrent complications due to persistent microbial infections.

Over the past decade, third generation self-inactivating (SIN) lentiviral vectors (LVVs) have been used as gene therapy vectors for the treatment of various primary immunodeficiency diseases. The therapy, based on autologous modified hematopoietic stem cells, has proven to be a safe and effective treatment modality with more than 300 subjects treated over several indications. Almost no serious adverse events (SAEs) were recorded to date and most patients demonstrated safe establishment and stable long-term hematopoietic reconstitution with a substantial proportion of gene-modified cells.

In the past decade, various BTK LVVs were developed with a focus on increasing Btk expression to therapeutic levels. These constructs included synthetic promoters, some based on the endogenous BTK promoter and additional cis acting transcription regulatory elements. In addition, the BTK transgene was subjected to codon optimization which, in some cases resulted in a significant increase in Btk protein levels.

Btk expression varies across the different stages of B cell differentiation and in response to BCR activation in mature B cells. Btk is also expressed in NK and myeloid cells and is necessary for their function. Surprisingly, the issue of Btk expression specificity was not the focus of many of past studies. Therefore, the main challenge that remains unsolved is the ability to tightly control the level of Btk that is produced exclusively in target cells. On one hand, there is the need to produce Btk levels that are sufficient for the correction of the phenotype. On the other hand, it has been shown that high levels of Btk may be associated with autoimmunity and carcinogenicity.

Endogenous promoters were previously used in LVV gene therapy clinical trials, and this is a common approach to design expression cassettes that mimic physiological expression patterns. However, early attempts to use the unmodified BTK endogenous promoter have been unsuccessful due to insufficient Btk expression in CD34+ cells. As a result of these studies, the current common notion is that the BTK endogenous promoter must be improved by addition of generic or B cell specific regulatory elements to reach therapeutic Btk levels. This general notion was recently reconfirmed by Seymour et al. (Molecular Therapy: Methods & Clinical Development (2021)) who showed that gene therapy with exclusively endogenous BTK promoter LVV failed to increase the serum concentrations of IgM or IgG in BTK-/TEC-mice, while gene therapy using modified BTK promoter constructs led to increases in antibody production and secretion. However, the inclusion of generic regulatory element as part of the expression cassette, holds a risk in the maintenance of Btk tight regulation.

There remains an unmet need for a BTK expression vector (e.g., LVV) that ensures Btk production with an efficacious and safe expression pattern.

SUMMARY OF THE INVENTION

According to a first aspect, there is provided a polynucleotide comprising: (a) a first nucleic acid molecule comprising a sequence of between 799 to 1,533 nucleotides of a human endogenous Bruton's tyrosine kinase (BTK) promoter; and (b) a second nucleic acid molecule comprising a codon optimized sequence encoding a BTK or a functional analog thereof, wherein the first nucleic acid molecule and the second nucleic acid molecule are operably linked, and wherein the codon optimized is for BTK expression in a subject, cell derived therefrom, or both.

According to another aspect, there is provided an expression vector comprising the polynucleotide of the invention.

According to another aspect, there is provided a hematopoietic stem cell comprising the polynucleotide of the invention.

According to another aspect, there is provided a composition comprising the hematopoietic stem cell of the invention, and a pharmaceutically acceptable carrier.

According to another aspect, there is provided a method for enhancing B cell viability or activity in a subject in need thereof, the method comprising transducing a cell derived or obtained from the subject with the expression vector disclosed herein, thereby enhancing B cell viability or activity in the subject.

In some embodiments, the polynucleotide further comprises a third nucleic acid molecule comprising a sequence of at least one expression regulatory element, wherein the third nucleic acid molecule is contiguous to the first nucleic acid molecule.

In some embodiments, the third nucleic acid molecule is located between the first nucleic acid molecule and the second nucleic acid molecule.

In some embodiments, the expression comprises transcription, translation, or both.

In some embodiments, the regulatory element comprises a sequence derived from an untranslated region (UTR) of a human BTK transcript.

In some embodiments, the first nucleic acid molecule comprises a nucleic acid sequence set forth in any one of SEQ ID Nos: 1-7.

In some embodiments, the second nucleic acid molecule comprises a nucleic acid sequence set forth in any one of SEQ ID Nos: 8-13.

In some embodiments, the sequence derived from a UTR of a human BTK transcript comprises a nucleic acid sequence set forth in SEQ ID Nos: 14-17.

In some embodiments, the polynucleotide comprises a nucleic acid sequence set forth in SEQ ID Nos: 19-30, and 32-33.

In some embodiments, the expression vector is a lentivirus-based expression vector.

In some embodiments, transducing comprises contacting the cell with the expression vector disclosed herein ex vivo.

In some embodiments, the method further comprises a step of selecting a subject in need of enhancement of B cell viability or activity, the selecting comprises determining any one of: B cell survival in the subject, B cell proliferation in the subject, B cell differentiation in the subject, and any combination thereof.

In some embodiments, the viability or activity comprises: survival, proliferation, differentiation, or any combination thereof.

In some embodiments, the method further comprises a step of transplanting the cell transduced with the expression vector disclosed herein to the subject.

In some embodiments, the subject is afflicted with X-linked agammaglobulinemia (XLA).

In some embodiments, the subject is characterized by: reduced B cell survival rate, reduced B cell proliferation and/or differentiation rate, or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A-1D include graphs showing comparison of BTK codon optimized expression cassettes. Transgene and transcript levels were measured 5 days post transduction at Multiplicity of infection (MOI)100 in in CD34+ cells derived from two healthy donors. (1A) Schematic description of the tested vectors. (1B) A vertical bar graph showing GFP mRNA levels relative to NTX101 as measured by real-time qPCR. (1C) A vertical bar graph showing percentage of GFP positive cells as measured by flow cytometry. (1D) A vertical bar graph showing BTK mean fluorescence intensity relative to un-transduced cells. BTK, Bruton's tyrosine kinase; 5'UTR, 5' untranslated region; Tag, FLAG tag; GFP, green fluorescent protein; CO, Codon optimized; 2A, T2A cleavage site and UN, Un-transduced.

FIGS. 2A-2D include a comparison of codon optimized BTK expression cassettes under BTK minimal promoters. GFP and Btk transgene levels were measured 6 days post transduction (MOI25). (2A) Schematic description of the tested vectors. (2B) dot plot of the different expression cassette of donor #6. (2C) GFP % of cell and MFI as measured by flow cytometry. (2D) Btk levels as measured by ELISA.

FIGS. 3A-3D include graphs showing comparison of BTK expression cassettes derived from different BTK minimal promoters in CD34+ cells derived from two healthy donors. Transgene level were measured 5 days post transduction (MOI100). (3A) Schematic description of the tested vectors. (3B) Dot plots of the different expression cassettes of donor 5. (3C) A vertical bar graph showing percentage of GFP positive cells as measured by flow cytometry. (3D) A vertical bar graph showing GFP MFI (mean fluorescence intensity).

FIGS. 4A-4D include a comparison of codon optimized BTK expression cassettes under different BTK minimal promoter in in CD34+ cells derived from 2 different donors. Transgene and transcript levels were measured 6 days post transduction (MOI12.5). (4A) Schematic description of the tested vectors. (4B) Dot plot of the different expression cassette of donor #5. (4C) Relative transcript levels. (4D) GFP MFI as measured by flow cytometry. MFI; mean fluorescence intensity.

FIGS. 5A-5E include a comparison of codon optimized BTK expression cassettes under different BTK 5'UTR in 2 different donors. Transgene and transcript levels were measured 6 days post transduction (MOI12.5). (5A) Schematic description of the tested vectors. (5B) dot plot of the different expression cassette of donor #5. (5C) Relative transcript levels. (5D) Percentage of GFP positive cells as measured by flow cytometry (5E). GFP MFI as measured by flow cytometry.

FIGS. 6A-6C include a comparison of a codon optimized BTK expression cassette to prior art disclosed in international patent application No. PCT/US2018/028331 in CD34 cells derived from two healthy donors. (6A) Schematic description of the tested vectors. (6B) Dot plot of the different expression cassette of the 2 donors. (6C) GFP MFI as measured by flow cytometry.

FIGS. 7A-7D include NTX109 dose response in CD34 cells derived from two healthy donors. Transgene levels were measured 6 days post transduction. (7A) Dot plot of GFP levels at the different MOIs. (7B) Absolute vector copy number. (7C) Percentage of GFP positive cells as measured by flow cytometry. (7D) BTK protein levels.

FIGS. 8A-8D include scatter plots of FACS analyses and a vertical bar graphs of Lin− cells derived from Xid mice post transduction with NTX101 and NTX109. GFP levels were measured 7 days post transduction. (8A) Percentage of GFP positive cells as measured by flow cytometry. (8B) GFP MFI as measured by flow cytometry. (8C) FACS plot analysis gated on B-cells showing in vitro differentiation of Xid lin− cells to B-cells, 17 days following transduction. (8D) FACS plot analysis gated on IgM positive cells showing in vitro differentiation of Xid lin− cells to B-cells, 17 days following transduction.

FIGS. 9A-9G include transplantation of NTX109 transduced Xid Lin− cells to Xid mice. NTX109 was transduced into Xid cells at 12.5-50 MOI and transplanted into Xid mice (n=8) 24 hours post transduction. (9A) A schematic description of a non-limiting study design. (9B) VCN/cell measured ex vivo and in the bone marrow, 6 days post transduction and 14 weeks post transplantation, respectively. (9C) GFP expression of PBMCs subtypes derived from bone marrow tissue. (9D) GFP expression of PBMCs subtypes derived from spleen tissue. (9E) T/B GFP+ cell ratio in spleen tissue. (9F) Plots showing percentage of GFP positive cells in various B cell populations as measured by flow cytometry. (9G) Percentage of mature B cells (B220$^+$IgM$^{low}$) in the spleen.

FIGS. 10A-10D include antibody secretion analysis following in vitro splenocytes stimulation with lipopolysaccharide (LPS) 15 weeks post Xid$^{NTX109}$ transplantation. (10A) A schematic showing a non-limiting description of splenocytes stimulation procedure. (10B) IgM levels Pre stimulation as measured by ELISA. (10C) IgM levels Post stimulation as measured by ELISA (n=8). (10D) Average IgM levels Post stimulation (pg) per NTX109 responding B cell.

DETAILED DESCRIPTION OF THE INVENTION

The present invention, in some embodiments, is directed to a polynucleotide comprising a nucleic acid molecule comprising a sequence encoding a Bruton's tyrosine kinase (BTK) or a functional analog thereof under the regulation of a nucleic acid molecule comprising an optimal sequence of the human endogenous BTK promoter.

The present invention, in some embodiments, is further directed to an expression vector, e.g., a viral-based expression vector, comprising the polynucleotide of the invention, and methods of using same, comprising transducing a cell for treating a subject inflicted with X-linked Agammaglobulinemia (XLA).

The expression of BTK may be improved to better mimic BTK regulation by addition of one or more transcription regulatory sequences derived from the BTK locus, derived from non-BTK locus, or a combination thereof. Such elements may be contiguous to minimal or optimal promoter, as disclosed herein, to optimize the expression module, described herein.

The present invention is based, in part, on the finding that utilizing an LVV based on the endogenous BTK promoter, provides physiological Btk expression levels in CD34+ HSC and functional restoration of Btk in a XLA mouse model with a sustained and specific BTK expression. This approach offers therapeutic benefit while minimizing the risk due to unregulated BTK expression in treated XLA patients.

In some embodiments, the method comprises obtaining a cell from a subject, transducing the cell ex vivo or in vitro, determining that vector copy number (VCN) is below a selected threshold and re-introducing or transplanting the transduced cell back to the subject from which it was obtained.

In some embodiments, the cell is transduced with the expression vector of the invention at an MOI of 10 to 30.

In some embodiments, the transduced cell is characterized by a VCN of not more than 3, of the vector of the invention.

In some embodiments, the method comprises transducing the cell in vitro or ex vivo with the expression vector of the invention at an MOI of 10 to 30, determining that the VCN is equal to or lower than 3, and then re-introducing or transplanting the transduced cell back to the subject from which it was obtained.

Polynucleotides

According to some embodiments, there is provided a polynucleotide comprising: (a) a first nucleic acid molecule comprising a sequence derived from a Bruton's tyrosine kinase (BTK) promoter; and (b) a second nucleic acid molecule comprising a sequence encoding a BTK transgene or a functional analog thereof.

According to some embodiments, there is provided a polynucleotide comprising: (a) a first nucleic acid molecule comprising a sequence derived of a human endogenous Bruton's tyrosine kinase (BTK) promoter; and (b) a second nucleic acid molecule comprising a sequence encoding a BTK or a functional analog thereof.

In some embodiments, the first nucleic acid molecule and the second nucleic acid molecule are operably linked.

As used herein, the term "promoter" refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

The term "optimal BTK promoter" as used herein refers to a nucleotide sequence contiguous to the transcription start site of the BTK gene that elicits therapeutic BTK expression levels and shows specific expression in B and myeloid cells while minimizing expression in T cells. In some embodiments, therapeutic BTK expression levels are at a clinically relevant VCN, as disclosed herein.

As used herein, the term "therapeutic BTK expression" refers to expression levels of BTK that are required to provide or elicit an improvement of the condition of an XLA patient, or to maintain, sustain, preserve, or any combination thereof, a non-pathological state in an XLA patient.

In some embodiments, a therapeutic BTK expression is required in a subject having or characterized by under-expression, downregulation, expression of a non-functional BTK or no expression of BTK.

In some embodiments, a subject in need, as disclosed herein, is characterized by or having under-expression, downregulation, expression of a non-functional BTK or no expression of BTK.

In some embodiments, a therapeutic BTK expression is at least 1.5-fold, 2-fold, 3-fold, 4-fold, 5-fold, 6-fold, 7-fold, 8-fold, 9-fold, or 10-fold higher than the endogenous BTK expression level of a similar cell which does not comprise the vector of the invention. In some embodiments, a therapeutic BTK expression is at least 1.5-fold, 2-fold, 3-fold, 4-fold, 5-fold, 6-fold, 7-fold, 8-fold, 9-fold, or 10-fold higher than the average healthy population endogenous BTK expression level of a specific cell type such as CD34+ or B cell. In some embodiments, a therapeutic BTK expression does not exceed 1.5-fold, 2-fold, 3-fold, 4-fold, 5-fold, 6-fold, 7-fold, 8-fold, 9-fold, or 10-fold higher than the endogenous BTK expression level of a similar cell which does not comprise the vector of the invention. In some embodiments, a therapeutic BTK expression does not exceed 1.5-fold, 2-fold, 3-fold, 4-fold, 5-fold, 6-fold, 7-fold, 8-fold, 9-fold, or 10-fold higher than the average healthy population endogenous BTK expression level of a specific cell type such as CD34+ or B cell which does not comprise the vector of the invention.

In some embodiments, a therapeutic BTK expression as disclosed herein, is provided by a cell transduced with the expression vector of the invention being transduced at an MOI of 1 to 100, 5-95, 10-80, 15-90, 10-70, 15-65, 20-95, 10-50, 5-50, 6-70, 10-40, 5-30, 4-35, 10-35, or 10-30. Each possibility represents a separate embodiment of the invention.

In some embodiments a therapeutic BTK expression as disclosed herein, is provided by a cell transduced with the expression vector of the invention being transduced as disclosed herein and being characterized or determined as having a VCN of 5 at most, 4 at most, 3 at most, 2 at most, 1 at most, or any value and range therebetween. Each possibility represents a separate embodiment of the invention.

In some embodiments a therapeutic BTK expression as disclosed herein, is provided by a cell transduced with the expression vector of the invention being transduced as disclosed herein and being characterized or determined as having a VCN of 1-2, 1-3, or 2-3. Each possibility represents a separate embodiment of the invention.

In some embodiments, a therapeutic BTK expression as disclosed herein, is provided by a cell transduced with the expression vector of the invention being transduced at an MOI of 1 to 100, 5-95, 10-80, 15-90, 10-70, 15-65, 20-95, 10-50, 5-50, 6-70, 10-40, 5-30, 4-35, 10-35, or 10-30, and being determined as having a VCN of 5 at most, 4 at most, 3 at most, 2 at most, 1 at most, or any value and range therebetween. Each possibility represents a separate embodiment of the invention.

In some embodiments, the optimal BTK promoter elicits therapeutic BTK expression levels. In some embodiments, the optimal BTK promoter directs, induces, promotes, activates, any equivalent thereof, or any combination thereof, BTK expression specifically or predominantly in a hematopoietic stem cell (HSC), a B cell, a myeloid cell, or any combination thereof. In some embodiments, the optimal BTK promoter directs, induces, promotes, activates, any equivalent thereof, or any combination thereof, minimal, negligible, or no BTK expression in a T cell.

In some embodiments, the optimal promoter comprises nucleotides from the endogenous BTK promoter.

In some embodiments, the optimal BTK promoter consists of nucleotides from the endogenous BTK promoter.

In some embodiments, the promoter comprises between 799 to 1533 nucleotides of the endogenous BTK promoter. In some embodiments, the promoter comprises between 1,033 to 1,533 nucleotides of the endogenous BTK promoter. In some embodiments, the promoter comprises at least 789 nucleotides, at least 800 nucleotides at least 1,000 nucleotides, at least 1,250 nucleotides, at least 1,500 nucleotides, at least 2,000 nucleotides, at least 2,500 nucleotides, at least 2,750 nucleotides, or at least 2,900 nucleotides, upstream of the transcription start site, or any value and range therebetween. Each possibility represents a separate embodiment of the invention. In some embodiments, the promoter of the invention comprises or is 790 to 3,100 nucleotides long.

In some embodiments, the promoter is further optimized by eliminating at least one potential methylation site. Methylation sites are eliminated by replacement of a C or a G in the promoter sequence.

In some embodiments, the first nucleic acid molecule comprises a nucleic acid sequence set forth in any one of SEQ ID Nos.: 1-4, and 6-7.

In some embodiments, a promoter as disclosed herein, comprises a nucleic acid sequence being listed in table 1 hereinbelow.

TABLE 1

Minimal BTK promoters

| SEQ ID NO: | Construct name | Sequence |
| --- | --- | --- |
| 1 | BTKP 1-180 | GACTCAAGATAGTAGTGTCAGAGGTCCCAAGCAAA TGAAGGGCGGGGACAGTTGAGGGGGTGGAATAGG GACGGCAGCAGGGAACCAGATAGCATGCTGCTGAG AAGAAAAAAAGACATTGGTTTAGGTCAGGAAGCAA AAAAAAGGGAACTGAGTGGCTGTGAAAGGGTGGGGT TTGCTC |
| 2 | BTKP 1-398 | GCTCTTCCTGGCCAGTCTCTTTGCTCTGTGTCTGCCA GCCCCCAGCATCTCTCCTCTTTCCTGTAAGCCCCTC TCCCTGTGCTGACTGTCTTCATAGTACTTTAGGTAT GTTGTCCCTTTACCTCTGGGAGGATAGCTTGATGAC CTGTCTGCTCAGGCCAGCCCCATCTAGAGTCTCAGT GGCCCCAGTCATGTTGAGAAAGGTTCTTTCAAAGAT AGACTCAAGATAGTAGTGTCAGAGGTCCCAAGCAA ATGAAGGGCGGGGACAGTTGAGGGGGTGGAATAG GGACGGCAGCAGGGAACCAGATAGCATGCTGCTGA GAAGAAAAAAAGACATTGGTTTAGGTCAGGAAGCA AAAAAAGGGAACTGAGTGGCTGTGAAAGGGTGGG GTTTGCTC |
| 3 | BTKP 1-588 | GTATTTCTGTGGGCTTATATTCCGACATTTTTATCTG TAGGGGAAAAATGCTTTCTTAGAAAATGACTCAGC ACGGGGAAGTCTTGTCTCTACCTCTGTCTTGTTTTGT CCTTTGGGGTCCCTTCACTATCAAGTTCAACTGTGT GTCCCTGAGACTCCTCTGCCCCGGAGGACAGGAGA CTCGAAAAACGCTCTTCCTGGCCAGTCTCTTTGCTC TGTGTCTGCCAGCCCCCAGCATCTCTCCTCTTTCCT GTAAGCCCCTCTCCCTGTGCTGACTGTCTTCATAGT ACTTTAGGTATGTTGTCCCTTTACCTCTGGGAGGAT AGCTTGATGACCTGTCTGCTCAGGCCAGCCCCATCT AGAGTCTCAGTGGCCCCAGTCATGTTGAGAAAGGT TCTTTCAAAGATAGACTCAAGATAGTAGTGTCAGA GGTCCCAAGCAAATGAAGGGCGGGGACAGTTGAGG GGGTGGAATAGGGACGGCAGCAGGGAACCAGATA GCATGCTGCTGAGAAGAAAAAAAGACATTGGTTTA GGTCAGGAAGCAAAAAAAGGGAACTGAGTGGCTGT GAAAGGGTGGGGTTTGCTC |

TABLE 1-continued

Minimal BTK promoters

| SEQ ID NO: | Construct name | Sequence |
|---|---|---|
| 4 | BTKP 1-1,033 | ACCCCATTTTTTTGTTTGCTTGTTTGTTTGTTTTTA<br>GACAAAATAAAGAAAAAAAAATAAGGTCCTGTTGA<br>CTTAAAACTTCGGATGAAATTGTAGTGGGACCTGTG<br>ATCTGTTTCTACATTAGGATACAGTGCCTTGGGGCA<br>AGGAAATATGGCAGTGCCCGAGGTGTCAAGGTGGG<br>CAGGCAGATCAGTCAGCAGGGGCTCCACCATCATG<br>GTCTGCATTCAATACTGGCTGCATTTCCTAGGAGAA<br>TCCCTGGGGAATCATTGCAGTTGGAGCATAATGT<br>AGGGGGCCCCTGAGAAAACCTCCAGGCTTCAAGTG<br>ACATACCTAGTCTGCTTTACCGGTTTACAGGACTCA<br>AGAGAAAGGTGGACATTGAGAGTTAATCCCTGAGG<br>CCAAATCTTAAATGGAGAAAGTCAACATCCACAGA<br>AAATGGGGAAGGGCACAAGTATTTCTGTGGGCTTA<br>TATTCCGACATTTTTATCTGTAGGGGAAAAATGCTT<br>TCTTAGAAAATGACTCAGCACGGGGAAGTCTTGTCT<br>CTACCTCTGTCTTGTTTTGTCCTTTGGGGTCCCTTCA<br>CTATCAAGTTCAACTGTGTGTCCCTGAGACTCCTCT<br>GCCCCGGAGGACAGGAGACTCGAAAAACGCTCTTC<br>CTGGCCAGTCTCTTTGCTCTGTGTCTGCCAGCCCCC<br>AGCATCTCTCCTCTTTCCTGTAAGCCCCTCTCCCTGT<br>GCTGACTGTCTTCATAGTACTTTAGGTATGTTGTCC<br>CTTTACCTCTGGGAGGATAGCTTGATGACCTGTCTG<br>CTCAGGCCAGCCCCATCTAGAGTCTCAGTGGCCCC<br>AGTCATGTTGAGAAAGGTTCTTTCAAAGATAGACTC<br>AAGATAGTAGTGTCAGAGGTCCCAAGCAAATGAAG<br>GGCGGGGACAGTTGAGGGGGTGGAATAGGGACGG<br>CAGCAGGGAACCAGATAGCATGCTGCTGAGAAGAA<br>AAAAAGACATTGGTTTAGGTCAGGAAGCAAAAAAA<br>GGGAACTGAGTGGCTGTGAAAGGGTGGGGTTTGCT<br>C |
| 5 | BTKP 1-180 &<br>589-1,033 | ACCCCATTTTTTTGTTTGCTTGTTTGTTTGTTTTTA<br>GACAAAATAAAGAAAAAAAAATAAGGTCCTGTTGA<br>CTTAAAACTTCGGATGAAATTGTAGTGGGACCTGTG<br>ATCTGTTTCTACATTAGGATACAGTGCCTTGGGGCA<br>AGGAAATATGGCAGTGCCCGAGGTGTCAAGGTGGG<br>CAGGCAGATCAGTCAGCAGGGGCTCCACCATCATG<br>GTCTGCATTCAATACTGGCTGCATTTCCTAGGAGAA<br>TCCCTGGGGAATCATTGCAGTTGGAGCATAATGT<br>AGGGGGCCCCTGAGAAAACCTCCAGGCTTCAAGTG<br>ACATACCTAGTCTGCTTTACCGGTTTACAGGACTCA<br>AGAGAAAGGTGGACATTGAGAGTTAATCCCTGAGG<br>CCAAATCTTAAATGGAGAAAGTCAACATCCACAGA<br>AAATGGGGAAGGGCACAAGACTCAAGATAGTAGTG<br>TCAGAGGTCCCAAGCAAATGAAGGGCGGGGACAGT<br>TGAGGGGGTGGAATAGGGACGGCAGCAGGGAACC<br>AGATAGCATGCTGCTGAGAAGAAAAAAAGACATTG<br>GTTTAGGTCAGGAAGCAAAAAAAGGG |
| 6 | BTKP 1-798 | GCATTTCCTAGGAGAATCCCTGGGGAATCATTGC<br>AGTTGGAGCATAATGTAGGGGGCCCCTGAGAAAAC<br>CTCCAGGCTTCAAGTGACATACCTAGTCTGCTTTAC<br>CGGTTTACAGGACTCAAGAGAAAGGTGGACATTGA<br>GAGTTAATCCCTGAGGCCAAATCTTAAATGGAGAA<br>AGTCAACATCCACAGAAAATGGGGAAGGGCACAA<br>GTATTTCTGTGGGCTTATATTCCGACATTTTTATCTG<br>TAGGGGAAAAATGCTTTCTTAGAAAATGACTCAGC<br>ACGGGGAAGTCTTGTCTCTACCTCTGTCTTGTTTTGT<br>CCTTTGGGGTCCCTTCACTATCAAGTTCAACTGTGT<br>GTCCCTGAGACTCCTCTGCCCCGGAGGACAGGAGA<br>CTCGAAAAACGCTCTTCCTGGCCAGTCTCTTTGCTC<br>TGTGTCTGCCAGCCCCAGCATCTCTCCTCTTTCCT<br>GTAAGCCCCTCTCCCTGTGCTGACTGTCTTCATAGT<br>ACTTTAGGTATGTTGTCCCTTTACCTCTGGGAGGAT<br>AGCTTGATGACCTGTCTGCTCAGGCCAGCCCCATCT<br>AGAGTCTCAGTGGCCCCAGTCATGTTGAGAAAGGT<br>TCTTTCAAAGATAGACTCAAGATAGTAGTGTCAGA<br>GGTCCCAAGCAAATGAAGGGCGGGGACAGTTGAGG<br>GGGTGGAATAGGGACGGCAGCAGGGAACCAGATA<br>GCATGCTGCTGAGAAGAAAAAAAGACATTGGTTTA<br>GGTCAGGAAGCAAAAAAAGGGAACTGAGTGGCTGT<br>GAAAGGGTGGGGTTTGCTC |

TABLE 1-continued

Minimal BTK promoters

| SEQ ID NO: | Construct name | Sequence |
|---|---|---|
| 7 | BTKP 1-1,533 | CAAATGTGAGTATCAACCACTCTATCATCAGTCTAC<br>AAATACTTTAAATGTTTTTATTTAAAGTCCTGTTGA<br>TGGCTGGGAGAGGTGGCTCACTCCTGTAATCCCTGC<br>ATTTTGGGAGGCCAAGGCAGGAGTATCGCTTGAGC<br>CCAGGAGTTTGAGACCAGCCTGGGCAACATAGTGA<br>AACCCCATCTCTACAAAAAGTAGAAAAATTAGCCC<br>AGCACAGTGATGTGTGCCTATAGTCCCAGGTACTA<br>GGGTGACTGAGGTGAGAGGATCACTTGAGCCCAGG<br>AGGTGGAGGCTGCAGTGAGCCATGATCACGCCACT<br>GCACTCCAACCTGGGCTTCAGAGCAAGACCCTGTC<br>TCAAAAAAAAAAAAAAAAAAAAAAGGTCCCAGGG<br>CCTGTTGGGGCTTGGGGGTGAGGGGAGGGATCTTA<br>GAGGATGGGTCAATAGGTGCAGCAAATCACCATGT<br>CACACATATACCTATGTAACAAACTTGCACCTTCTG<br>CACATATACCCCATTTTTTTTGTTTGCTTGTTTGTTT<br>GTTTTTTAGACAAAATAAAGAAAAAAAAATAAGGT<br>CCTGTTGACTTAAAACTTCGGATGAAATTGTAGTGG<br>GACCTGTGATCTGTTTCTACATTAGGATACAGTGCC<br>TTGGGGCAAGGAAATATGGCAGTGCCCGAGGTGTC<br>AAGGTGGGCAGGCAGATCAGTCAGCAGGGGCTCCA<br>CCATCATGGTCTGCATTCAATACTGGCTGCATTTCC<br>TAGGAGAATCCCTGGGGAATCATTGCAGTTGGAG<br>CATAATGTAGGGGGCCCCTGAGAAAACCTCCAGGC<br>TTCAAGTGACATACCTAGTCTGCTTTACCGGTTTAC<br>AGGACTCAAGAGAAAGGTGGACATTGAGAGTTAAT<br>CCCTGAGGCCAAATCTTAAATGGAGAAAGTCAACA<br>TCCACAGAAAATGGGGAAGGGCACAAGTATTTCTG<br>TGGGCTTATATTCCGACATTTTTATCTGTAGGGGAA<br>AAATGCTTTCTTAGAAAATGACTCAGCACGGGGAA<br>GTCTTGTCTCTACCTCTGTCTTGTTTTGTCCTTTGGG<br>GTCCCTTCACTATCAAGTTCAACTGTGTGTCCCTGA<br>GACTCCTCTGCCCCGGAGGACAGGAGACTCGAAAA<br>ACGCTCTTCCTGGCCAGTCTCTTTGCTCTGTGTCTGC<br>CAGCCCCCAGCATCTCTCCTCTTTCCTGTAAGCCCC<br>TCTCCCTGTGCTGACTGTCTTCATAGTACTTTAGGT<br>ATGTTGTCCCTTTACCTCTGGGAGGATAGCTTGATG<br>ACCTGTCTGCTCAGGCCAGCCCCATCTAGAGTCTCA<br>GTGGCCCCAGTCATGTTGAGAAAGGTTCTTTCAAAG<br>ATAGACTCAAGATAGTAGTGTCAGAGGTCCCAAGC<br>AAATGAAGGGCGGGGACAGTTGAGGGGGTGGAAT<br>AGGGACGGCAGCAGGGAACCAGATAGCATGCTGCT<br>GAGAAGAAAAAAAGACATTGGTTTAGGTCAGGAAG<br>CAAAAAAAGGGAACTGAGTGGCTGTGAAAGGGTG<br>GGGTTTGCTC |

In some embodiments, the use of a longer promoter may improve regulation of gene expression. In contrast, increased size of the lentiviral vectors can significantly reduce lentivirus production. In some embodiments, the use of a longer promoter may improve regulation of gene expression. In contrast, increased size of the lentiviral vectors can significantly reduce lentivirus production efficiency therefore affect the commerciality of such lentiviral vectors. Therefore, both aspects should be optimized for selection of lead BTK lentiviral vectors.

In some embodiments, the first nucleic acid molecule is located at the 5' end of the second nucleic acid. In some embodiments, the 3' end of the first nucleic acid molecule precedes the 5' of the second nucleic acid molecule.

In some embodiments, the second nucleic acid molecule comprises a nucleic acid sequence encoding a BTK protein. In some embodiments, the second nucleic acid molecule comprises a nucleic acid sequence encoding a BTK transgene being optimized for expression in a host cell or a in subject comprising same.

In some embodiments, the codon optimization is a partial, confined, directed, or tailored codon optimization. In some embodiments, the entire second nucleic acid molecule is codon optimized. In some embodiments, portions of the second nucleic acid molecule are codon optimized. In some embodiments, the second nucleic acid molecule is codon optimized in a way wherein sequences which are regulated or configured for regulation at the nucleic acid sequence level are not codon optimized, e.g., as a wild type allele. In some embodiments, the second nucleic acid molecule is codon optimized in a way wherein only sequences which are regulated or configured for regulation at the nucleic acid sequence level are not codon optimized, e.g., as a wild type allele. In some embodiments, the second nucleic acid molecule is codon optimized in a way wherein sequences which are not regulated or not configured for regulation at the nucleic acid sequence level are codon optimized. In some embodiments, the second nucleic acid molecule is codon optimized in a way wherein only sequences which are not regulated or not configured for regulation at the nucleic acid sequence level are codon optimized.

In some embodiments, the second nucleic acid molecule is codon optimized in a way wherein sequences which are regulated or configured for regulation at the nucleic acid sequence level are not codon optimized, e.g., as a wild type allele, and sequences which are not regulated or not configured for regulation at the nucleic acid sequence level are codon optimized. In some embodiments, the second nucleic acid molecule is codon optimized in a way wherein only sequences which are regulated or configured for regulation at the nucleic acid sequence level are not codon optimized, e.g., as a wild type allele, and wherein only sequences which are not regulated or not configured for regulation at the nucleic acid sequence level are codon optimized.

Methods for optimizing a codon according to a codon preference of a host cell are common and would be apparent to one of ordinary skill in the art. While codon optimization may be useful to increase transgene expression, it also introduces base alterations to the original sequence. Such alterations may eliminate important regulatory sequence within the transgene and should be carefully designed. The selected codon optimized BTK sequence should retain a high degree of similarity to the WT BTK nucleotide sequence. In some embodiments, the codon optimized BTK of the invention retains at least 95%, 90%, 85%, 80%, 75% or any value there between to the WT BTK nucleotide sequence. In some embodiments, the second nucleic acid molecule comprises a nucleic acid sequence set forth in any one of SEQ ID Nos.: 8-12.

TABLE 2

BTK coding sequences

| SEQ ID NO: | Construct name | Sequence |
|---|---|---|
| 8 | BTK | ATGGCCGCAGTGATTCTGGAGAGCATCTTTCTGAAG<br>CGATCCCAACAGAAAAAGAAAACATCACCTCTAAA<br>CTTCAAGAAGCGCCTGTTTCTCTTGACCGTGCACAA<br>ACTCTCCTACTATGAGTATGACTTTGAACGTGGGAG<br>AAGAGGCAGTAAGAAGGGTTCAATAGATGTTGAGA<br>AGATCACTTGTGTTGAAACAGTGGTTCCTGAAAAA<br>AATCCTCCTCCAGAAAGACAGATTCCGAGAAGAGG<br>TGAAGAGTCCAGTGAAATGGAGCAAATTTCAATCA<br>TTGAAAGGTTCCCTTATCCCTTCCAGGTTGTATATG<br>ATGAAGGGCCTCTCTACGTCTTCTCCCCAACTGAAG<br>AACTAAGGAAGCGGTGGATTCACCAGCTCAAAAAC<br>GTAATCCGGTACAACAGTGATCTGGTTCAGAAATA<br>TCACCCTTGCTTCTGGATCGATGGGCAGTATCTCTG<br>CTGCTCTCAGACAGCCAAAAATGCTATGGGCTGCC<br>AAATTTTGGAGAACAGGAATGGAAGCTTAAAACCT<br>GGGAGTTCTCACCGGAAGACAAAAAAGCCTCTTCC<br>CCCAACGCCTGAGGAGGACCAGATCTTGAAAAAGC<br>CACTACCGCCTGAGCCAGCAGCAGCACCAGTCTCC<br>ACAAGTGAGCTGAAAAAGGTTGTGGCCCTTTATGA<br>TTACATGCCAATGAATGCAAATGATCTACAGCTGC<br>GGAAGGGTGATGAATATTTTATCTTGGAGGAAAGC<br>AACTTACCATGGTGGAGAGCACGAGATAAAAATGG<br>GCAGGAAGGCTACATTCCTAGTAACTATGTCACTG<br>AAGCAGAAGACTCCATAGAAATGTATGAGTGGTAT<br>TCCAAACACATGACTCGGAGTCAGGCTGAGCAACT<br>GCTAAAGCAAGAGGGGAAAGAAGGAGGTTTCATTG<br>TCAGAGACTCCAGCAAAGCTGGCAAATATACAGTG<br>TCTGTGTTTGCTAAATCCACAGGGGACCCTCAAGGG<br>GTGATACGTCATTATGTTGTGTGTTCCACACCTCAG<br>AGCCAGTATTACCTGGCTGAGAAGCACCTTTTCAGC<br>ACCATCCCTGAGCTCATTAACTACCATCAGCACAAC<br>TCTGCAGGACTCATATCCAGGCTCAAATATCCAGTG<br>TCTCAACAAAACAAGAATGCACCTTCCACTGCAGG<br>CCTGGGATACGGATCATGGGAAATTGATCCAAAGG<br>ACCTGACCTTCTTGAAGGAGCTGGGGACTGGACAA<br>TTTGGGGTAGTGAAGTATGGGAAATGGAGAGGCCA<br>GTACGACGTGGCCATCAAGATGATCAAAGAAGGCT<br>CCATGTCTGAAGATGAATTCATTGAAGAAGCCAAA<br>GTCATGATGAATCTTTCCCATGAGAAGCTGGTGCAG<br>TTGTATGGCGTCTGCACCAAGCAGCGCCCCATCTTC<br>ATCATCACTGAGTACATGGCCAATGGCTGCCTCCTG<br>AACTACCTGAGGGAGATGCGCCACCGCTTCCAGAC<br>TCAGCAGCTGCTAGAGATGTGCAAGGATGTCTGTG<br>AAGCCATGGAATACCTGGAGTCAAAGCAGTTCCTT |

TABLE 2-continued

BTK coding sequences

| SEQ ID NO: | Construct name | Sequence |
|---|---|---|
|  |  | CACCGAGACCTGGCAGCTCGAAACTGTTTGGTAAA<br>CGATCAAGGAGTTGTTAAAGTATCTGATTTCGGCCT<br>GTCCAGGTATGTCCTGGATGATGAATACACAAGCT<br>CAGTAGGCTCCAAATTTCCAGTCCGGTGGTCCCCAC<br>CGGAAGTCCTGATGTATAGCAAGTTCAGCAGCAAA<br>TCTGACATTTGGGCTTTTGGGGTTTTGATGTGGGAA<br>ATTTACTCCCTGGGGAAGATGCCATATGAGAGATTT<br>ACTAACAGTGAGACTGCTGAACACATTGCCCAAGG<br>CCTACGTCTCTACAGGCCTCATCTGGCTTCAGAGAA<br>GGTATATACCATCATGTACAGTTGCTGGCATGAGA<br>AAGCAGATGAGCGTCCCACTTTCAAAATTCTTCTGA<br>GCAATATTCTAGATGTCATGGATGAAGAATCCTGA |
| 9 | COBTK1 | ATGGCCGCCGTCATCCTAGAGAGCATCTTCCTGAAG<br>AGATCTCAGCAAAAGAAGAAAACCTCCCCTCTGAA<br>CTTCAAGAAGCGGCTGTTCCTGCTGACCGTGCACAA<br>ACTGAGCTACTACGAGTACGATTTCGAGCGGGGAA<br>GAAGAGGAAGCAAGAAGGGCTCTATCGACGTGGA<br>AAAAATCACATGCGTGGAGACCGTGGTGCCCGAGA<br>AGAACCCTCCACCAGAACGGCAGATCCCCAGAAGG<br>GGGGAGGAATCTAGCGAGATGGAACAGATCAGCAT<br>CATCGAGAGGTTTCCTTATCCTTTCCAGGTGGTTTA<br>CGACGAAGGTCCTCTGTATGTGTTCAGCCCCACAGA<br>AGAACTGCGGAAGCGCTGGATCCACCAGCTGAAGA<br>ACGTGATCAGATACAACAGCGACCTGGTGCAGAAA<br>TACCACCCCTGCTTCTGGATCGACGGCCAGTACCTC<br>TGCTGCAGCCAAACAGCCAAGAATGCTATGGGCTG<br>CCAGATCCTGGAAAACCGAAACGGCTCTCTGAAAC<br>CTGGCAGCAGCCATCGGAAGACCAAGAAGCCCCTG<br>CCTCCTACCCCGAAGAGGACCAAATCCTGAAGAA<br>ACCTCTGCCACCTGAGCCAGCCGCTGCTCCTGTGAG<br>CACCTCCGAGCTGAAAAAGGTGGTGCCCCTGTACG<br>ATTACATGCCTATGAACGCCAACGACCTCCAGTTGC<br>GCAAGGGCGACGAGTACTTCATTCTGGAAGAGTCC<br>AACCTGCCTTGGTGGCGGGCCAGAGATAAGAACGG<br>CCAAGAGGCTATATCCCCAGCAATTACGTGACCG<br>AGGCCGAAGATTCGATCGAGATGTACGAGTGGTAC<br>AGCAAGCACATGACCAGAAGCCAGGCCGAGCAGCT<br>GCTGAAGCAGGAGGGCAAGGAAGGCGGCTTCATCG<br>TTAGAGATTCTTCTAAAGCCGGCAAGTACACAGTGT<br>CCGTGTTCGCCAAGAGCACAGGCGATCCCCAGGGA<br>GTCATTCGGCACTACGTGGTGTGTAGTACCCCTCAG<br>AGCCAGTACTACCTGGCTGAGAAGCACCTGTTCTCT<br>ACAATCCCTGAGCTGATCAACTACCACCAGCACAA<br>CAGCGCCGGCCTGATCAGCAGACTGAAATACCCCG<br>TGAGCCAACAGAACAAGAACGCCCCCTCTACAGCC<br>GGCCTGGGATATGGAAGCTGGGAGATCGACCCCAA<br>GGACCTGACCTTCCTGAAGGAACTGGGCACCGGCC<br>AGTTTGGAGTGGTCAAGTACGGCAAATGGAGAGGC<br>CAGTACGATGTGGCCATCAAGATGATCAAGGAGGG<br>CTCTATGAGCGAAGATGAGTTCATAGAGGAAGCGA<br>AAGTGATGATGAATCTGTCTCATGAGAAGCTGGTG<br>CAGCTGTACGGCGTGTGTACAAAACAGAGACCTAT<br>CTTTATTATCACCGAGTACATGGCTAACGGCTGTCT<br>GCTGAATTACCTGCGGGAAATGAGACACAGATTCC<br>AGACACAGCAACTGCTGGAGATGTGCAAGGACGTG<br>TGCGAGGCCATGGAATACCTGGAATCCAAGCAGTT<br>CCTGCACCGGGACCTGGCCGCCAGAAATTGTCTGG<br>TGAACGACCAGGGCGTGGTCAAGGTGTCCGACTTC<br>GGCCTGAGCAGATACGTGCTGGACGACGAATACAC<br>CAGCAGCGTGGGCAGCAAATTCCCTGTCAGATGGA<br>GCCCTCCTGAAGTGCTGATGTACAGCAAGTTCAGC<br>AGCAAGAGCGACATCTGGGCCTTTGGAGTGCTGAT<br>GTGGGAAATCTACTCTCTGGGCAAGATGCCTTACG<br>AGAGATTCACCAACAGCGAAACCGCCGAGCACATC<br>GCCCAGGGCCTGCGGCTGTATCGGCCTCACCTGGCC<br>AGCGAGAAAGTGTACACCATCATGTATAGCTGCTG<br>GCACGAGAAGGCCGACGAGAGACCTACCTTTAAGA<br>TCCTGCTGTCCAACATCCTGGATGTGATGGACGAGG<br>AATCCTGA |
| 10 | COBTK2 | ATGGCCGCTGTGATTCTGGAGAGCATCTTCCTCAAG<br>AGGTCCCAGCAGAAGAAGAAGACCAGCCCCCTCAA<br>CTTCAAGAAGAGGCTGTTCCTCCTCACCGTCCATAA |

TABLE 2-continued

BTK coding sequences

| SEQ ID NO: | Construct name | Sequence |
|---|---|---|
| | | GCTGAGCTACTACGAGTACGACTTCGAAAGGGGAA
GAAGGGGCTCCAAAAAGGGCTCCATCGACGTGGAG
AAGATCACATGCGTGGAAACCGTGGTCCCCGAAAA
AAATCCCCCCCCCGAAAGGCAGATCCCCAGAAGGG
GAGAGGAGTCCAGCGAAATGGAGCAGATCTCCATC
ATCGAAAGGTTCCCCTACCCCTTCCAAGTGGTGTAC
GACGAAGGCCCTCTGTACGTGTTCTCCCCCACCGAA
GAACTGAGAAAGAGGTGGATCCACCAGCTGAAGAA
CGTCATTAGATACAACTCCGACCTCGTGCAGAAAT
ACCACCCTTGCTTCTGGATCGACGGCCAGTATCTGT
GTTGCAGCCAAACAGCCAAGAACGCTATGGGCTGC
CAGATTCTGGAGAATAGAAACGGCAGCCTCAAGCC
CGGCAGCAGCCATAGGAAGACCAAAAAGCCTCTGC
CTCCCACCCCCGAGGAGGATCAGATTCTGAAGAAG
CCTCTGCCTCCCGAGCCCGCCGCTGCTCCCGTGAGC
ACATCCGAGCTGAAGAAGGTGGTCGCTCTGTACGA
CTACATGCCCATGAACGCCAATGACCTCCAACTGA
GAAAGGGAGACGAGTACTTTATTCTGGAGGAGAGC
AACCTCCCTTGGTGGAGAGCTAGGGATAAGAATGG
CCAAGAGGGATACATCCCCAGCAACTATGTGACCG
AGGCCGAGGACAGCATTGAGATGTACGAGTGGTAC
AGCAAGCATATGACAAGATCCCAAGCCGAGCAACT
GCTGAAGCAAGAGGGCAAGGAGGGCGGCTTCATTG
TGAGAGACAGCTCCAAGGCTGGCAAATACACCGTG
AGCGTGTTCGCCAAGAGCACCGGCGATCCCCAAGG
CGTGATCAGACATTACGTCGTGTGCAGCACCCCTCA
GTCCCAGTACTACCTCGCCGAGAAACACCTCTTCT
CACAATCCCCGAGCTGATTAACTACCACCAGCACA
ACTCCGCCGGCCTCATTCTAGACTGAAGTACCCCG
TCAGCCAGCAGAATAAGAATGCTCCCTCCACAGCT
GGACTGGGCTACGGAAGCTGGGAGATCGACCCCAA
AGATCTGACCTTTCTGAAAGAATGGGCACCGGCCA
AATTTGGCGTGGTGAAGTACGGCAAGTGGAGGGGC
CAGTACGACGTGGCTATTAAGATGATCAAGGAGGG
AAGCATGTCCGAGGACGAGTTCATCGAGGAAGCTA
AGGTGATGATGAATCTGAGCCACGAGAAGCTGGTG
CAGCTCTACGGCGTGTGTACCAAGCAAAGGCCCAT
CTTCATTATCACAGAGTATATGGCCAATGGCTGCCT
CCTCAACTATCTGAGAGAGATGAGGCATAGATTCC
AGACCCAACAGCTGCTGGAGATGTGCAAAGATGTG
TGCGAGGCCATGGAGTACCTCGAAAGCAAGCAGTT
TCTGCATAGAGACCTCGCCGCTAGAAATTGTCTGGT
GAACGATCAAGGCGTCGTGAAGGTGAGCGATTTTG
GACTGAGCAGATACGTGCTGGACGATGAGTACACC
AGCAGCGTCGGATCCAAGTTCCCCGTGAGATGGAG
CCCTCCCGAGGTGCTGATGTACTCCAAGTTCAGCTC
CAAGTCCGACATCTGGGCCTTTGGCGTGCTGATGTG
GGAGATTTACTCTCTGGGCAAGATGCCCTACGAGA
GGTTTACCAACAGCGAGCAGCCGAACACATCGCC
CAAGGACTGAGGCTGTATAGGCCCCACCTCGCCTC
CGAGAAGGTGTACACCATTATGTACAGCTGCTGGC
ACGAGAAGGCCGACGAGAGGCCCACATTCAAGATT
CTGCTGTCCAACATTCTGGACGTGATGGACGAAGA
GTCCTGA |
| 11 | COBTK3 | ATGGCGGCAGTGATTTTGGAATCCATCTTCCTGAAA
CGCAGTCAGCAGAAGAAAAAACTAGTCCGCTTAA
CTTTAAGAAAAGGCTTTTCTTGTTGACAGTCCACAA
GCTGAGTTATTATGAATACGATTTTGAAAGGGGAA
GGAGGGGCTCCAAGAAAGGGAGTATAGACGTCGA
GAAGATTACATGCGTTGAAACGTGTTGTGCCGGAGA
AGAATCCCCGCCGGAAAGACAAATTCCTCGACGG
GGCGAAGAGTCCAGTGAAATGGAGCAAATTTCTAT
TATCGAGCGCTTCCCTTACCCATTCCAGGTAGTATA
TGACGAAGGGCCCTTGTACGTGTTCTCTCCGACAGA
AGAACTCCGGAAACGCTGGATCCATCAGTTGAAAA
ATGTAATACGCTACAATAGTGACCTGGTACAGAAA
TACCACCCTTGTTTTTGGATTGATGGCCAATACTTG
TGTTGTAGTCAGCCCAAAGATGCAATGGGTTG
CCAAATTTTGGAGAATGAAACGGGAGCCTCAAGC
CAGGAAGCTCTCATCGCAAAACAAAAAAACCCTTG
CCACCGACTCCCGAGGAAGATCAGATCCTGAAGAA
ACCTCTTCCCCCTGAGCCTGCAGCAGCTCCTGTCAG
CACGTCCGAGCTTAAGAAAGTGGTCGCATTGTACG |

| SEQ ID NO: | Construct name | Sequence |
|---|---|---|
| | | ATTACATGCCGATGAACGCTAACGATCTGCAGCTG
AGAAAAGGCGACGAGTACTTTTATCCTCGAGGAATC
TAACCTCCCGTGGTGGAGAGCAAGAGATAAAAACG
GACAAGAGGGGTACATCCCCTCAAATTATGTGACA
GAGGCGGAGGATTCCATCGAGATGTACGAGTGGTA
TTCAAAGCACATGACTCGGAGCCAGGCCGAGCAAT
TGCTTAAACAGGAGGGGAAAAGAAGGTGGCTTTATA
GTGAGGGACTCTAGCAAGGCTGGAAAATACACGGT
GAGCGTATTTGCCAAGTCTACGGGAGATCCCCAAG
GGGTTATAAGGCACTACGTAGTCTGTTCAACTCCCC
AGAGCCAGTACTATCTTGCGGAAAAGCACCTCTTCT
CCACTATTCCTGAGCTGATAAATTACCATCAACATA
ACAGCGCGGGCCTGATAAGCAGGCTCAAATACCCG
GTCTCCCAACAGAACAAGAACGCACCTTCTACCGC
AGGGCTCGGTTATGGCTCATGGGAAATTGACCCGA
AAGATCTTACTTTCCTGAAGGAACTCGGCACTGGCC
AGTTCGGCGTTGTAAAGTACGGAAAATGGAGGGGA
CAATATGACGTCGCGATAAAAATGATCAAAGAGGG
GTCCATGAGTGAGGACGAATTTATTGAGGAGGCGA
AAGTAATGATGAATCTCAGTCATGAAAAACTCGTA
CAATTGTATGGTGTTTGCACCAAACAACGACCAATT
TTTATCATAACCGAGTACATGGCCAACGGTTGTTTG
CTTAATTACCTAGAGAGAAATGCGAACATCGGTTCCA
AACACAACAACTGCTTGAGATGTGTAAGGATGTCT
GCGAAGCAATGGAGTACCTCGAATCAAAACAGTTC
CTTCACAGAGATCTTGCGGCGCGAACTGTCTGGTT
AACGATCAGGCGTAGTTAAGGTCAGCGACTTTGG
GCTCTCACGATATGTTCTTGATGATGAGTATACCAG
CAGTGTTGGATCAAAGTTCCCTGTTAGGTGGTCACC
GCCAGAGGTTCTGATGTATAGCAAGTTCTCTTCTAA
GAGTGACATCTGGGCCTTCGGCGTACTCATGTGGG
AGATCTATTCCCTGGGCAAGATGCCTTACGAGAGA
TTCACCAATAGCGAAACTGCCGAACACATCGCCCA
AGGCCTTAGACTCTATCGGCCGCACCTCGCGAGCG
AAAAGGTCTATACAATCATGTACTCCTGTTGGCATG
AGAAAGCTGATGAGCGCCCAACGTTCAAGATACTT
CTCAGTAATATCCTTGACGTAATGGATGAGGAATCC
TGA |
| 12 | COBTK4 | ATGGCCGCAGTGATTCTGGAGAGCATCTTTCTGAAG
CGGTC

TABLE 2-continued

BTK coding sequences

| SEQ ID NO: | Construct name | Sequence |
|---|---|---|
| | | CAGTTTGGGGTGGTGAAGTACGGGAAATGGCGGGG
CCAGTACGACGTGGCCATCAAGATGATCAAAGAAG
GCTCCATGTCTGAAGATGAATTCATTGAAGAAGCC
AAAGTCATGATGAATCTGTCCCACGAGAAGCTGGT
GCAGCTGTACGGCGTCTGCACCAAGCAGCGGCCCA
TCTTCATCATCACCGAGTACATGGCCAATGGCTGCC
TCCTGAACTACCTGCGGGAGATGCGGCACCGGTTC
CAGACCCAGCAGCTGCTGGAGATGTGCAAGGATGT
CTGCGAAGCCATGGAATACCTGGAGAGCAAGCAGT
TCCTGCACCGGGACCTGGCAGCTCGGAACTGCCTG
GTGAACGATCAGGGAGTGGTGAAAGTGTCTGATTT
CGGCCTGTCCCGGTACGTCCTGGATGATGAATACAC
AAGCAGCGTGGGCTCCAAATTTCCAGTCCGGTGGT
CCCCACCCGAAGTCCTGATGTACAGCAAGTTCAGC
AGCAAATCTGACATTTGGGCTTTTGGGGTGCTGATG
TGGGAAATCTATTCCCTGGGGAAGATGCCATACGA
GCGGTTTACCAACAGCGAGACCGCTGAACACATTG
CCCAGGGCCTGCGGCTCTACCGGCCTCACCTGGCTA
GCGAGAAGGTGTACACCATCATGTACAGCTGCTGG
CACGAGAAAGCAGATGAGCGGCCCACCTTCAAAAT
TCTGCTGAGCAATATTCTGGATGTCATGGATGAAGA
ATCCTGA |
| 13 | BTK ORF disclosed in international patent application No. PCT/US2018/028331 | ATGGCCGCTGTGATCCTGGAGAGCATTTTCCTGAAG
AGGTCCCAGCAGAAAAAGAAAACCTCTCCCCTGAA
CTTTAAGAAAAGACTGTTCCTGCTGACAGTGCACA
AGCTGTCTTACTATGAGTACGACTTTGAGCGGGGCC
GCCGAGGATCAAAAAAGGGGAGCATCGATGTGCA
GAAGATTACATGCGTGGAGACCGTGGTCCCTGAAA
AGAATCCACCCCCTGAGAGGCAGATCCCAAGACGG
GGCGAGGAGTCCTCTGAGATGGAGCAGATTAGTAT
CATTGAGCGCTTCCCCTATCCTTTTCAGGTGGTGTA
CGACGAGGGACCACTGTATGTGTTCTCACCCACAG
AGGAGCTGAGAAAGAGGTGGATTCACCAGCTGAAG
AACGTGATTAGATACAATAGCGATCGGTGCAGAA
GTATCACCCTTGTTTTTGGATCGACGGGCAGTACCT
GTGCTGTTCCCAGACAGCTAAGAACGCTATGGGAT
GCCAGATTCTGAAAATCGGAACGGATCTCTGAAA
CCAGGGAGTTCACACCGCAAGACCAAAAAGCCCT
GCCTCCAACACCCGAGGAGGATCAGATCCTGAAAA
AGCCTCTGCCACCCGAGCCTGCTGCAGCCCCAGTCA
GCACTTCCGAACTGAAAAAGGTGGTGGCTCTGTAT
GACTACATGCCCATGAATGCTAACGATCTGCAGCT
GAGAAAGGGCGACAGTATTTCATTCTGGAAGAGT
CTAATCTGCCTTGGTGGAGGGCCAGAGATAAGAAC
GGACAGGAGGGGTACATCCCATCTAATTATGTGAC
CGAGGCTGAGGACTCTATTGAGATGTACGAGTGGT
ATAGCAAGCACATGACACGGTCCCAGGCTGAGCAG
CTGCTGAAGCAGGAGGCAAAGAGGGAGGGTTTAT
CGTGCGCGATTCTAGTAAGGCCGGCAAATACACTG
TGTCAGTGTTCGCTAAGAGCACCGGAGACCCCCAG
GGCGTGATCAGACACTATGTGGTGTGTTCCACACCT
CAGTCTCAGTACTATCTGGCTGAGAAGCACCTGTTT
AGTACAATCCCAGAGCTGATTAACTACCACCAGCA
CAATTCTGCCGGCCTGATCAGCAGGCTGAAGTATCC
CGTCTCCCAGCAGAACAAAAATGCTCCTTCTACCGC
TGGACTGGGGTACGGCAGTTGGGAGATTGATCCAA
AGGACCTGACATTCCTGAAGGAGCTGGGAACTGGG
CAGTTTGGCGTGGTGAAGTATGGAAAATGGAGAGG
GCAGTACGATGTGGCCATCAAGATGATCAAGGAGG
GCTCAATGAGCGAGGACGAGTTCATCGAGGAGGCT
AAGGTCATGATGAACCTGTCCCACGAGAAACTGGT
GCAGCTGTATGGAGTGTGCACCAAGCAGCGGCCCA
TTTTTATCATTACAGAGTACATGGCTAATGGGTGTC
TGCTGAACTATCTGCGCGAGATGAGACACAGATTC
CAGACACAGCAGCTGCTGGAAATGTGCAAGGATGT
GTGTGAGGCTATGGAGTACCTGGAGTCTAAGCAGT
TTCTGCACCGGGACCTGGCTGCTCGCAATTGCCTGG
TGAACGATCAGGGCGTGGTGAAGGTGAGTGACTTC
GGACTGTCAAGGTATGTGCTGGATGACGAGTACAC
CAGCTCCGTGGGCTCTAAGTTTCCTGTGAGATGGTC
TCCACCCGAGGTGCTGATGTATAGCAAGTTCTCCTC
TAAGAGCGATATCTGGGCCTTTGGCGTGCTGATGTG
GGAAATCTACAGCCTGGGCAAGATGCCTTACGAGC
GGTTCACAAATTCCGAGACAGCTGAGCACATCGCC
CAGGGCCTGCGCCTGTACCGGCCACATCTGGCCTCT
GAGAAGGTGTACACCATCATGTACAGCTGTTGGCA
CGAGAAGGCCGACGAGAGACCCACATTCAAGATCC
TGCTGTCCAACATTCTAGATGTGATGGACGAGGAG
AGCTGA |

In some embodiments, the polynucleotide further comprises a third nucleic acid molecule. In some embodiments, the third nucleic acid molecule comprises a sequence of at least one expression regulatory element. In some embodiments, the first nucleic acid molecule is located at the 5' end of the third nucleic acid. In some embodiments, the polynucleotide comprises the nucleic acid molecules contiguous to one another in the following order from 5' to 3': the 3' end of the first nucleic acid molecule contiguous to the 5' end of the third nucleic acid molecule, and the 3' end of the third nucleic acid molecule contiguous to the 5' end of the second nucleic acid molecule.

In some embodiments, the third nucleic acid molecule is located between the first nucleic acid molecule and the second nucleic acid molecule.

As used herein, the term "expression regulatory element" refers to any compound or agent, whether endogenous or exogenous that is capable of modifying the expression of a gene and therefore, affect the amount of a protein product encoded therefrom. In some embodiments, modifying is increasing or decreasing. In some embodiments, expression comprises gene transcription (e.g., to RNA), mRNA translation (e.g., to peptide), or both.

In some embodiments, a regulatory element comprises a sequence derived from the untranslated region (UTR) of a BTK transcript. In some embodiments, the regulatory element comprises a sequence derived from the 5'UTR of a BTK transcript, a sequence derived from the 3' UTR of a BTK transcript, or any combination thereof. In some embodiments, the regulatory element is a sequence derived from a 5' UTR derived of the full length, natural BTK transcript as presented in SEQ ID No. 14, or a partial sequence thereof comprises a nucleic acid sequence set forth in any one of SEQ ID Nos.: 15-16.

TABLE 3

BTK UTR and UCOE

| SEQ ID NO: | Construct name | Sequence |
|---|---|---|
| 14 | BTK 5'UTR 160 | AGACTGTCCTTCCTCTCTGGACTGTAAGAATATGTCTCCAGG
GCCAGTGTCTGCTGCGATCGAGTCCCACCTTCCAAGTCCTGG
CATCTCAATGCATCTGGGAAGCTACCTGCATTAAGTCAGGAC
TGAGCACACAGGTGAACTCCAGAAAGAAGAAGCT |

TABLE 3-continued

BTK UTR and UCOE

| SEQ ID NO: | Construct name | Sequence |
|---|---|---|
| 15 | BTK 5'UTR 31 | AGACTGTCCTTCCTCTCTGGACTGTAAGAAT |
| 16 | BTK 5'UTR modified | AGACTGTCCTTCCTCTCTCAACTGTAACAATATGTCTCCAGG GCCAGTGTCTGCTGCGATCGAGTCCCACCTTCCAAGTCCTGG CATCTCAATGCATCTGGCAAGCTACCTGCAATAAGTCACCAC TGAGCACACACAACAACTCCACAAACAACAAGCT |
| 17 | BTK 5'UTR disclosed in international patent application No. PCT/US2018 | AGACTGTCCTTCCTCTCTGGACTGTAAGAATTAGTCTCGAG |
| 18 | UCOE disclosed in international patent application No. PCT/US2018/ 028331 | CGCAAACACCCGAATCAACTTCTAGTCAAATTATTGTTCACG CCGCAATGACCCACCCCTGGCCCGCGTCTGTGGAACTGACCC CTGGTGTACAGGAGAGTTCGCTGCTGAAAGTGGTCCCAAAG GGGTACTAGTTTTTAAGCTCCCAACTCCCCCTCCCCCAGCGT CTGGAGGATTCCACACCCTCGCACCGCAGGGGCGAGGAAGT GGGCGGAGTCCGGTTTTGGCGCCAGCCGCTGAGGCTGCCAA GCAGAAAAGCCACCGCTGAGGAGACTCCGGTCACTGTCCTC GCCCCGCCTCCCCCTTCCCTCCCCTTGGGGACCACCGGGCGC CACGCCGCGAACGGTAAGTGCCGCGGTCGTCGGCGCCTCCG CCCTCCCCCTAGGGCCCCAATTCCCAGCGGGCGCGGCGCGC GGCCCCTCCCCCCGCCGGGCGCGCGCCCGCTGCCCCGCCCTT CGTGGCCGCCCGGCGTGGGCGGTGCCACCCCTCCCCCCAGC GGCCCCGCGCGCAGCTCCCGGCTCCCTCCCCCTTCGGATGTG GCTTGAGCTGTAGGCGCGGAGGGCCGGAGACGCTGCAGACC CGCGACCCGGAGCAGCTCGGAGGCGGTGAAGTCGGTGGCTT TCCTTCTCTCTAGCTCTCGCTCGCTGGTGGTGCTTCAGATGCC ACAC |

In some embodiments, the polynucleotide of the invention further comprises a fourth nucleic acid molecule. In some embodiments, the fourth nucleic acid molecule comprises a sequence of a protein translation initiation motif. In some embodiments, a protein translation initiation motif comprises a mammalian, e.g., a human, protein translation initiation motif.

Types of protein translation initiation motif would be apparent to one of ordinary skill in the art, including means for retrieving or obtaining their sequences. In some embodiments, a protein translation initiation motif comprises a Kozak consensus sequence. In some embodiments, the fourth nucleic acid molecule comprises a Kozak consensus sequence or any functional equivalent thereof. In some embodiments, the polynucleotide of the invention comprises a Kozak consensus sequence or any functional equivalent thereof. In some embodiments, a Kozak consensus sequence as disclosed herein comprises the nucleic acid sequence: GCCRCCAUG (SEQ ID NO: 34), wherein R is A or G.

In some embodiments, the fourth nucleic acid molecule is located between the third nucleic acid molecule and the second nucleic acid molecule. In some embodiments, the fourth nucleic acid molecule is contiguous to the third nucleic acid molecule. In some embodiments, the fourth nucleic acid molecule is located at the 5' end of the second nucleic acid. In some embodiments, the fourth nucleic acid molecule is located at the 5' end of the second nucleic acid. In some embodiments, the polynucleotide comprises the nucleic acid molecules in the following order from 5' to 3': the first nucleic acid molecule, the third nucleic acid molecule, the fourth nucleic acid molecule, and the second nucleic acid molecule.

In some embodiments, the 3' end of the first nucleic acid molecule precedes the 5' of the third nucleic acid molecule. In some embodiments, the 3' end of the third nucleic acid molecule precedes the 5' of the fourth nucleic acid molecule. In some embodiments, the 3' end of the fourth nucleic acid molecule precedes the 5' of the second nucleic acid molecule. In some embodiments, the second nucleic acid molecule is contiguous to the fourth nucleic acid molecule. In some embodiments, the polynucleotide comprises the nucleic acid molecules contiguous to one another in the following order from 5' to 3': the 3' end of the first nucleic acid molecule contiguous to the 5' end of the third nucleic acid molecule, the 3' end of the third nucleic acid molecule contiguous to the 5' end of the fourth nucleic acid molecule, and the 3' end of the fourth nucleic acid molecule contiguous to the 5' end of the second nucleic acid molecule.

In some embodiments, the third nucleic acid molecule is contiguous to the first nucleic acid molecule. In some embodiments, the third nucleic acid molecule is located at the 5' end of the second nucleic acid. In some embodiments, the third nucleic acid molecule is located at the 3' end of the first nucleic acid. In some embodiments, the polynucleotide comprises the nucleic acid molecules in the following order from 5' to 3': the first nucleic acid molecule, the third nucleic acid molecule, and the second nucleic acid molecule.

In some embodiments, the 3' end of the first nucleic acid molecule precedes the 5' of the third nucleic acid molecule.

In some embodiments, the 3' end of the third nucleic acid molecule precedes the 5' of the second nucleic acid molecule. In some embodiments, the second nucleic acid molecule is contiguous to the third nucleic acid molecule.

In some embodiments, the polynucleotide of the invention comprises a nucleic acid sequence set forth in any one of SEQ ID Nos.: 19-33.

In some embodiments, the polynucleotide of the invention comprises a BTK expression cassette. In some embodiments, the expression cassette comprises an optimal BTK promoter and a BTK coding sequence. In some embodiments, the expression cassette consists of an optimal BTK promoter and a BTK coding sequence.

According to some embodiments, there is provided an expression cassette comprising an optimal BTK promoter and a codon optimized BTK coding sequence. In some embodiments, the expression cassette further comprises an expression regulatory element, a sequence of a protein translation initiation motif, or both. In some embodiments the regulatory sequence is derived from the BTK transcript 5' UTR. In some embodiments the regulatory comprises the full BTK transcript 5' UTR. In some embodiments, the expression cassette consists of an optimal BTK promoter, a codon optimized BTK coding sequence, an expression regulatory element, and a sequence of a protein translation initiation motif. In some embodiments, the expression cassette consists of the following elements in the following order from 5' to 3': an optimal BTK promoter (e.g., a human endogenous BTK promoter), an expression regulatory element, a sequence of a protein translation initiation motif, and a codon optimized BTK coding sequence.

In some embodiments, a BTK expression cassette as disclosed herein is listed in table 4 herein below.

TABLE 4

BTK expression cassettes

| SEQ ID NO: | Construct elements | Construct Name | Expression assembly order |
|---|---|---|---|
| 19 | P180 + 5'UTR160 + BTK | LV_NTX 104 | SEQ ID NO: 1 + SEQ ID NO: 14 + Kozak Sequence + SEQ ID NO: 8 |
| 20 | P398 + 5'UTR160 + BTK | LV_NTX 103 | SEQ ID NO: 2 + SEQ ID NO: 14 + Kozak Sequence + SEQ ID NO: 8 |
| 21 | P588 + 5'UTR160 + BTK | LV_NTX 102 | SEQ ID NO: 3 + SEQ ID NO: 14 + Kozak Sequence + SEQ ID NO: 8 |
| 22 | P1033 + 5'UTR160 + BTK | LV_NTX 101 | SEQ ID NO: 4 + SEQ ID NO: 14 + Kozak Sequence + SEQ ID NO: 8 |
| 23 | P1033 + 5'UTR160 + COBTK1 | LV_NTX 109 | SEQ ID NO: 4 + SEQ ID NO: 14 + Kozak Sequence + SEQ ID NO: 9 |
| 24 | P1033 + 5'UTR160, COBTK2 | LV_NTX 110 | SEQ ID NO: 4 + SEQ ID NO: 14 + Kozak Sequence + SEQ ID NO: 10 |
| 25 | P1033 + 5'UTR160, COBTK3 | LV_NTX 111 | SEQ ID NO: 4 + SEQ ID NO: 14 + Kozak Sequence + SEQ ID NO: 11 |
| 26 | P1033 + 5'UTR160, COBTK | LV_NTX 112 | SEQ ID NO: 4 + SEQ ID NO: 14 + Kozak Sequence + SEQ ID NO: 13 |
| 27 | P1-180 & 589-1,033 + 5'UTR160 + COBTK1 | LV_NTX 132 | SEQ ID NO: 5 + SEQ ID NO: 14 + Kozak Sequence + SEQ ID NO: 9 |
| 28 | P798 + 5'UTR160 + COBTK1 | LV_NTX 133 | SEQ ID NO: 6 + SEQ ID NO: 14 + Kozak Sequence + SEQ ID NO: 9 |
| 29 | P1533 + 5'UTR160 + COBTK1 | LV_NTX 134 | SEQ ID NO: 7 + SEQ ID NO: 14 + Kozak Sequence + SEQ ID NO: 9 |
| 30 | P1033 + 5'UTR 31 + COBTK1 | LV_NTX 137 | SEQ ID NO: 4 + SEQ ID NO: 15 + Kozak Sequence + SEQ ID NO: 9 |
| 31 | UCOE + P798 + 5'UTR + COBTK | LV_NTX 141 | SEQ ID NO: 18 + SEQ ID NO: 6 + SEQ ID NO: 17 + Kozak Sequence + SEQ ID NO: 13 |

TABLE 4-continued

BTK expression cassettes

| SEQ ID NO: | Construct elements | Construct Name | Expression assembly order |
|---|---|---|---|
| 32 | P1033 + 5'UTRMod + COBTK1 | LV_NTX 142 | SEQ ID NO: 4 + SEQ ID NO: 16 + Kozak Sequence + SEQ ID NO: 9 |
| 33 | P1033 + 5'UTR160, COBTK4 | LV_NTX 143 | SEQ ID NO: 4 + SEQ ID NO: 14 + Kozak Sequence + SEQ ID NO: 12 |

In some embodiments, the polynucleotide further comprises a fifth nucleic acid molecule comprising a sequence of or derived from a viral vector. In some embodiments, the viral vector comprises a lentiviral vector backbone. In some embodiments, a lentiviral vector comprises a third-generation lentiviral vector backbone. In some embodiments, a lentiviral vector comprises a self-inactivating lentiviral vector backbone. In some embodiments, a lentiviral vector comprises a third-generation self-inactivating lentiviral vector backbone.

In some embodiments, the polynucleotide of the invention is devoid of a ubiquitous chromatin opening element (UCOE).

Expression Vectors

According to some embodiments, there is provided an expression vector comprising the polynucleotide the invention.

In some embodiments, the expression vector is or comprises a viral vector.

In some embodiments, the expression vector is or comprises a lentivirus-based expression vector.

In some embodiments, a lentivirus-based vector comprises an inactivated lentiviral vector. In some embodiments, a lentivirus-based vector comprises a third-generation lentiviral vector. In some embodiments, a lentivirus-based vector comprises a self-inactivating lentiviral vector. In some embodiments, a lentivirus-based vector is devoid of a trans-activator of transcription encoding gene (Tat). In some embodiments, a lentivirus-based vector is devoid of one or more viral accessory proteins. In some embodiments, a viral accessory protein is selected from: vif, vpr, vpu, nef, or any combination thereof. In some embodiments, a lentivirus-based vector comprises any lentivirus-based vector suitable for human therapy. In some embodiments, suitable comprises safe for human health.

Lentivirus-based vectors, and specifically, lentivirus-based vectors that are safe for use in therapy of a human subject, are common and would be apparent to one of ordinary skill in the art.

In some embodiments, the gene is operably linked to a promoter. The term "operably linked" is intended to mean that the nucleotide sequence of interest is linked to the regulatory element or elements in a manner that allows for expression of the nucleotide sequence (e.g., in an in vitro transcription/translation system or in a host cell when the vector is introduced into the host cell).

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Numerous methods are known in the art for measuring expression levels of a one or more gene such as by amplification of nucleic acids (e.g., PCR, isothermal methods, rolling circle methods, etc.) or by quantitative in situ hybridization. Design of primers for amplification of specific genes is well known in the art.

RT-qPCR: A common technology used for measuring RNA abundance is RT-qPCR where reverse transcription (RT) is followed by real-time quantitative PCR (qPCR). Reverse transcription first generates a DNA template from the RNA. This single-stranded template is called cDNA. The cDNA template is then amplified in the quantitative step, during which the fluorescence emitted by labeled hybridization probes or intercalating dyes changes as the DNA amplification process progresses. Quantitative PCR provides a measurement of an increase or decrease in copies of the original RNA and has been used to attempt to define changes of gene expression in cancer tissue as compared to comparable healthy tissues.

Droplet digital polymerase chain reaction (ddPCR): a technology that provides absolute and direct quantification of target DNA. The ddPCR measures absolute quantities by counting nucleic acid molecules encapsulated in 20,000 water in oil droplet partitions. PCR amplification is carried out within each droplet using a thermal cycle. After PCR, droplets are streamed in single file on a droplet reader, which count the fluorescent positive and negative droplet to calculate target DNA concentration.

Cells

According to some embodiments, there is provided a cell comprising: (a) the polynucleotide of the invention; (b) the expression vector disclosed herein (e.g., comprising the polynucleotide of the invention); or (c) any combination of (a) and (b).

In some embodiments, a cell comprises a stem cell. In some, embodiments, a cell comprises a hematopoietic stem cell or a progenitor cell. In some embodiments, a cell comprises an immune cell. In some embodiments, a cell comprises a myeloid cell. In some embodiments, a cell comprises a B cell, a B lymphocyte, or a plasma cell.

In some embodiments, a cell is a CD34+ cell.

In some embodiments, the cell is or comprises a CD34+ hematopoietic stem cell.

Methods for determining the type of a cell as well as methods for isolating particular cells, e.g., CD34+, are common and would be apparent to one of ordinary skill in the art. A non-limiting example for such a method includes but is not limited to affinity purification and flow cytometry cell sorting (e.g., Fluorescent-activated cell sorting (FACS)).

In some embodiments, the cell is obtained or derived from a subject. In some embodiments, the cell is obtained or derived from a cell line or culture. In some embodiments, the cell is used for propagating and/or multiplying the polynucleotide of the invention or a vector comprising same. In some embodiments, the cell is used for expression of the polynucleotide of the invention or a vector comprising same.

In some embodiments, a cell comprising the polynucleotide of the invention, or a composition comprising same is characterized by having a BTK expression level comparable or equivalent to the endogenous BTK expression level in a control cell.

In some embodiments, a cell comprising the polynucleotide of the invention, or a composition comprising same is characterized by having a BTK expression level being similar to the endogenous BTK level. In some embodiments the cell is characterized by having a BTK expression level between 1 to 2-fold, 1-3-fold, 1-4-fold, 1-5-fold, 1-6-fold, 1-7-fold, 1-8-fold, 1-9-fold, or 1-10-fold greater than the endogenous BTK expression level in a similar cell which does not comprise the polynucleotide of the invention or an expression vector comprising same, or any value and range therebetween. Each possibility represents a separate embodiment of the invention.

In some embodiments, a cell comprising the polynucleotide of the invention, or a composition comprising same is characterized by having a BTK expression level of at least 30%, 40%, 50%, 60%, 70%, 80%, 90%, or similar levels compared to the endogenous BTK expression level in a similar cell which does not comprise the polynucleotide of the invention, or any value and range therebetween. In some embodiments, a cell comprising the polynucleotide of the invention, or a composition comprising same is characterized by having a BTK expression level of up to 150%, 200%, 300%, 400%, 500% or 1,000% Each possibility represents a separate embodiment of the invention.

In some embodiments, the vector copy number (VCN) of the herein disclosed vector comprising the polynucleotide of the invention in a cell as described herein is: 10 at most, 9 at most, 8 at most, 7 at most, 6 at most, 5 at most, 4 at most, 3 at most, 2 at most, or 1 at most, or any value and range therebetween. Each possibility represents a separate embodiment of the invention.

In some embodiments, the VCN of the herein disclosed vector comprising the polynucleotide of the invention in a cell as described herein is: 1-10, 1-9, 1-8, 1-7, 1-6, 1-5, 1-4, 1-3, or 1-2. Each possibility represents a separate embodiment of the invention.

In some embodiments, a control cell comprises a normal B cell. In some embodiments, a control cell comprises a normal myeloid cell. In some embodiments, a control cell comprises a normal hematopoietic stem cell. In some embodiments, a control cell comprises a B cell obtained or derived from a healthy subject. In some embodiments, a control cell comprises a myeloid cell obtained or derived from a healthy subject. In some embodiments, a control cell comprises any one of: a B cell, a myeloid cell, and both, and obtained or derived form a subject not afflicted with X-linked agammaglobulinemia (XLA).

Compositions

According to some embodiments, there is provided a composition comprising: (a) the polynucleotide of the invention; (b) an expression vector comprising the polynucleotide of the invention; (c) a cell comprising any one of: the polynucleotide of the invention; an expression vector comprising same, and any combination thereof; or any combination thereof.

In some embodiments, the composition further comprises an acceptable carrier.

In some embodiments, the carrier comprises a pharmaceutically acceptable carrier.

In some embodiments, there is provided a pharmaceutical composition comprising a cell as disclosed herein and a pharmaceutically acceptable carrier.

In some embodiments, the cell is a transduced cell.

In some embodiments, transduced comprises being transduced with the expression vector of the invention.

In some embodiments, the transduced cell is characterized by having a VCN of 1 or 2. In some embodiments, the cell is characterized by having a VCN<2, or <3.

In some embodiments, the pharmaceutical composition is for use in transplantation to a subject in need thereof.

In some embodiments, the pharmaceutical composition is for use in transplantation to a subject characterized by a loss of function mutation in the BTK gene, reduced B cell activation rate, reduced B cell proliferation and/or differentiation rate, or any combination thereof.

In some embodiments, reduced is compared to a control. In some embodiments, a control comprises a healthy subject. In some embodiments, a control comprises a subject not afflicted by a mutated BTK gene related disease, or a subject carrying a loss of function mutation in the BTK gene. In some embodiments, a control comprises a subject not afflicted by a loss of function mutation in the BTK gene. In some embodiments, a control comprises a subject not afflicted by a mutated BTK gene related disease. In some embodiments a control is based on published data on BTK expression in a specific cell type. In some embodiments a control is based on an average BTK expression measured in several healthy subjects and set as a baseline.

In some embodiments, a mutated BTK gene related disease comprises any disease involving mutated BTK gene as part of its pathogenesis and/or pathophysiology. In some embodiments, a mutated BTK gene related disease is characterized by reduced, inhibited, minute, non-existing B cell, myeloid cell, Natural killer cell (NK), or any combination thereof, viability and/or activity, or any combination thereof.

In some embodiments, a mutated BTK gene related disease comprises or is X-linked agammaglobulinemia (XLA). In some embodiments the XLA afflicted subject carries a loss of function mutation in the BTK gene.

In some embodiments, "reduced" or "reduction" comprises at least 5%, at least 10%, at least 20%, at least 30%, at least 40%, at least 50%, at least 60%, at least 70%, at least 80%, at least 90%, at least 95%, at least 99%, or 100% reduction, or any value and range therebetween. Each possibility represents a separate embodiment of the invention. In some embodiments, "reduced" or "reduction" comprises 1-20%, 10-50%, 35-75%, 20-97%, 15-80%, 1-75%, or 10-100% reduction. Each possibility represents a separate embodiment of the invention.

In some embodiments, a BTK expression cassette VCN equals to or lower than a predetermined threshold is indicative of the cell being suitable for transplantation to the subject. In some embodiments, a BTK expression cassette VCN above a predetermined threshold is indicative of the cell being unsuitable for transplantation to the subject. In some embodiments, VCN is measured as an average of a population of cells (pVCN). In some embodiments, VCN is measured at a single cell level (sVCN) using ddPCR.

In some embodiments, a VCN pre-determined threshold is a VCN of 1 at most, 2 at most, or 3 at most, including any value and range therebetween. Each possibility represents a separate embodiment of the invention.

In some embodiments, BTK expression equal to or greater than a predetermined threshold is indicative of the cell being suitable for transplantation to the subject. In some embodiments, BTK expression below a predetermined threshold is indicative of the cell being unsuitable for transplantation to the subject.

In some embodiments, a predetermined threshold comprises a ratio of transgene derived BTK (trBTK) expression to endogenous BTK (enBTK) expression being suitable for transplantation to the subject. In some embodiments, a trBTK/enBTK expression ratio indicative of a cell being suitable for transplantation to the subject comprises trBTK/enBTK expression ratio of at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, at least 60:1, at least 70:1, at least 80:1, at least 90:1, at least 100:1, at least 200:1, at least 350:1, at least 500:1, at least 700:1, at least 850:1, at least 1,000:1, or any value and range therebetween. Each possibility represents a separate embodiment of the invention. In some embodiments, a trBTK/enBTK expression ratio indicative of a cell being suitable for transplantation to the subject comprises trBTK/enBTK expression ratio of 2:1 to 20:1, 5:1 to 150:1, 30:1 to 300:1, 50:1 to 750:1, 10:1 to 1,000:1. Each possibility represents a separate embodiment of the invention.

In some embodiments, a predetermined threshold comprises a ratio of expression of the transgene in B-cells (bcBTK) to expression of the transgene in T-cells (tcBTK) being suitable for transplantation to the subject. In some embodiments, a bcBTK/tcBTK expression ratio indicative of a cell being suitable for transplantation to the subject comprises bBTK/tBTK expression ratio of at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, at least 60:1, at least 70:1, at least 80:1, at least 90:1, at least 100:1, at least 200:1, at least 350:1, at least 500:1, at least 700:1, at least 850:1, at least 1,000:1, or any value and range therebetween. Each possibility represents a separate embodiment of the invention.

Methods of Use

According to some embodiments, there is provided a method for enhancing B cell viability or activity in a subject in need thereof, the method comprising contacting a cell derived or obtained from the subject with the expression vector of the invention, thereby enhancing B cell viability or activity in the subject.

According to some embodiments, there is provided a method for enhancing a cell viability or activity in a subject in need thereof, the method comprising contacting a cell derived or obtained from the subject with the expression vector of the invention, thereby enhancing the cell viability or activity in the subject.

In some embodiments, the cell is a hematopoietic stem cell. In some embodiments, the cell is a myeloid cell. In some embodiments, the cell is a B cell.

According to some embodiments, there is provided a method for providing or restoring BTK activity or functionality in a cell, the method comprising contacting the cell with the expression vector of the invention, thereby providing or restoring BTK activity or functionality in the cell.

In some embodiments, the method further comprises a step comprising determining the expression level of BTK in the transduced cell. In some embodiments, the step comprising determining the expression level of the BTK in the transduced cell precedes the transplantation of the cell to the subject.

In some embodiments, the method is for treating or preventing XLA in a subject in need thereof.

In some embodiments, the method further comprises providing a cell derived or obtained from a subject inflicted with XLA.

In some embodiments, the method further comprises a step of obtaining a cell from a subject inflicted with XLA.

In some embodiments, contacting comprises or is contacting ex vivo.

As used herein the term "ex-vivo" refers to a process in which a cell is removed from a living organism and is propagated and/or manipulated outside the organism.

In some embodiments, contacting comprises transducing the cell with the expression vector of the invention. In some embodiments, contacting comprises introducing the expression vector of the invention to the cell with. In some embodiments, transducing comprises introducing the expression vector of the invention to the cell with.

In some embodiments, transducing and/or introducing comprises transferring an expression vector comprising the polynucleotide molecule into a target cell.

In some embodiments, transducing and/or introducing is at a multiplicity of infection (MOI) of at least 5, at least 10, at least 15, at least 20, at least 25, at least 30, at least 35, at least 40, at least 45, at least 50, or any value and range therebetween. Each possibility represents a separate embodiment of the invention.

In some embodiments, transducing and/or introducing is at an MOI of 5-50, 10-50, 10-40, 10-30, 10-25, 15-50, 15-40, 15-35, 20-40, 17-30, or 20-30. Each possibility represents a separate embodiment of the invention.

In some embodiments, the method further comprises a step of dose determination. In some embodiments, dose selection is done by measuring Btk expression in an XLA patient cell e.g. HSC or by measuring VCN in an XLA patient HSC or by measuring in-vitro B cell development of the transduced HSC.

Methods for determining B cell function, proliferation and/or differentiation are common and would be apparent to one of ordinary skill in the art. Non-limiting examples for such methods include, but are not limited to, FACS, antibody specific stains (e.g., with anti CD34+ antibody), MTT assay, XTT assay, ELISA assay, IgM secretion in response to stimulation, some of which are exemplified herein.

In some embodiments, the method further comprises a step comprising determining the Vector Copy Number (VCN) of BTK expression cassette in the transduced cell. In some embodiments, the step comprising determining VCN of BTK in the transduced cell precedes the transplantation of the cell to the subject.

In some embodiments, there is provided a method for treating a subject in need thereof, the method comprising administering to the subject a composition comprising a plurality of cells derived from the subject, wherein the cells are in vitro, ex vivo, or in vivo manipulated such that they are characterized by having bcBTK/tcBTK expression ratio of at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, at least 60:1, at least 70:1, at least 80:1, at least 90:1, at least 100:1, at least 200:1, at least 350:1, at least 500:1, at least 700:1, at least 850:1, at least 1,000:1, or any value and range therebetween, compared to the bcBTK/tcBTK of the subject before being treated according to the herein disclosed method.

In some embodiments, a predetermined threshold comprises a ratio of expression of the transgene in B-cells (bcBTK) to expression of the transgene in myeloid cells (mcBTK) being suitable for transplantation to the subject. In some embodiments, a bcBTK/mcBTK expression ratio indicative of a cell being suitable for transplantation to the subject comprises bcBTK/mcBTK expression ratio of at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, at least 60:1, at least 70:1, at least 80:1, at least 90:1, at least 100:1, at least 200:1, at least 350:1, at least 500:1, at least 700:1, at least 850:1, at least 1,000:1, or any value and range therebetween. Each possibility represents a separate embodiment of the invention.

In some embodiments, the subject is afflicted with a mutated BTK gene related disease. In some embodiments, the subject is afflicted with an immunodeficiency or an immunodeficient disease or disorder. In some embodiments, the subject is afflicted with X-linked agammaglobulinemia (XLA).

In some embodiments, a mutation in the BTK gene as disclosed herein is a loss of function mutation. In some embodiments, the mutation is a nonsense mutation. In some embodiments, the mutation is a missense mutation. In some embodiments, any one of the nonsense or missense mutations, as described herein, render a partial, non-functional, or both, protein product of the mutated BTK gene.

In some embodiments, treating comprises inducing the expression of BTK in a subject. In some embodiments, treating comprises inducing the expression levels of BTK in a B cell of a subject. In some embodiments, treating comprises inducing the expression levels of BTK in a myeloid cell of a subject. In some embodiments, the subject is characterized by no BTK expression or negligible BTK expression. In some embodiments, the subject is characterized by having a non-functional BTK gene or a protein product thereof.

In some embodiments, increasing the expression is to a level of 101%-150%, 150-200%, 200-300%, 101-300%, 101-500%, 101-1000%, 200-1000% compared to the endogenous BTK expression in a control B cell, hematopoietic stem cells (HSC), or a control myeloid cell, or any value and range therebetween. Each possibility represents a separate embodiment of the invention.

EXAMPLES

Various embodiments and aspects of the present invention as delineated herein above and as claimed in the claims section below find experimental support in the following examples. Reference is now made to the following examples, which together with the above descriptions illustrate some embodiments of the invention in a non-limiting fashion.

Generally, the nomenclature used herein, and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

Example 1

Screening for Vector Candidates Based on BTK and GFP Expression in Human Hematopoietic Stem Cells Derived from Healthy Donors The screening system utilizes $CD34^+$ human hematopoietic stem cells (HSCs) derived from mobilized peripheral blood cells (MPBCs). These cells are the most relevant expression system, as HSCs are the target cell population in the clinical setting. It was previously shown that BTK is expressed in $CD34^+$ cells (Rushworth et al. 2014). Therefore, transduction with BTK LVVs should lead to BTK expression in this cell population. Initially, the coding sequence of all expression cassettes includes a BTK-T2A-GFP sequence. Comparison of BTK mRNA and GFP protein levels of transduced and un-transduced $CD34^+$ cells, enables a choice of an initial set of candidate expression cassettes that are further evaluated by additional screening systems.

G-CSF MPBCs were collected by apheresis from healthy donors at the Ezer Mizion Bone Marrow Collection Site. CD34+ cells were purified by CD34 positive selection microbeads (Miltenyi), the purity of the selection process was determined using flow cytometry.

For transduction, human G-CSF MPBC-derived CD34+ cells are cultured in serum-free SCGM medium (CellGenix) supplemented with a cocktail of cytokines: IL-3, TPO, SCF, and FLT-3L (PeproTech) for 16 to 24 h prior to transduction. Transduction is carried out by mixing the viruses with the LentiBOOST (Sirion) transduction enhancer into an appropriate tissue culture dish. The CD34+ cells are added to the well at a high concentration of $0.5-1\times10^6$ cells/ml. Twenty-four (24) hours later, cells are washed to remove any virions left in the media. Cells are maintained and collected for molecular and biochemical studies at days 5-15 post transduction.

For BTK mRNA levels, total RNA is extracted from $0.5\times10^6$ CD34 transduced cells using PureLink RNA mini kit (Invitrogen) followed by RT reaction using High-capacity RNA to cDNA kit (Applied biosystems). Five (5) ng cDNA are used for the real time qPCR reaction (CFX96 touch deep well, Bio-rad). Hypoxanthine phosphoribosyl transferase (HPRT) is used as a reference gene. Primers sequences that are used to identify the different transcripts are described in Table 5.

TABLE 5

Primers sequences to measure transcript levels by real time PCR

| Target gene | Primer orientation | Sequence | SEQ ID NO: |
|---|---|---|---|
| BTK | Forward | 5'-AGCACGAGATAAAAATGGGCAG-3' | 35 |
|  | Reverse | 5'-ACTCCGAGTCATGTGTTTGGAA-3' | 36 |
| BTKCO | Forward | 5'-CAGATCCTGGAAAACCGAAA-3' | 37 |
|  | Reverse | 5'-AGGTGGCAGAGGTTTCTTCA-3' | 38 |
| HPRT1 | Forward | 5'-TGGATTACATCAAAGCACTGAATAG-3' | 39 |
|  | Reverse | 5'-CTTTCCAGTTAAAGTTGAGAGATCA-3' | 40 |

For GFP protein levels, $0.1-0.5\times10^6$ cells were collected and incubated with 7AAD viability dye (Beckman Culture) to eliminate any dead cells. Cells were filtered and screened for GFP levels using CytoFlex flow cytometry. Flow cytometry analysis was done using CytExpert. For Vector copy number (VCN) levels, gDNA is extracted from CD34 transduced cells using QiaAmp DNA micro kit (Qiagen). For each ddPCR reaction, 60 ng of DNA are used as a multiplex assay reaction comprising one lentiviral target, labeled with fluorescein amidite (FAM), and the PCBP2 human/mouse reference gene, labeled with HEX. Custom-made primers are stocked at 20× concentration, corresponding to a concentration of 900 nM for the primers and 250 nM for the hydrolysis probe. Sequences that are used to identify the different transcripts are described in Table 6.

TABLE 6

Primers and probe sequences to measure VCN by ddPCR

| Target gene | Primer orientation/ Probe | Sequence | SEQ ID NO: |
|---|---|---|---|
| HIV-gag | Forward | 5'-TCTCGACGCAGGACTCG-3' | 41 |
|  | Reverse | 5'-TACTGACGCTCTCGCACC-3' | 42 |
|  | Probe | 5'-TTTGGCGTACTCACCAGTCGCC-3' | 43 |
| PCBP2 IVS 13 | Forward | 5'-TTGTGTCTCCAGTCTGCTTG-3' | 44 |
|  | Reverse | 5'-AGGTGGTGGTGGTGGTA-3' | 45 |
|  | Probe | 5'-CCCTCTCCTGGCTCTAAATGTTGTGT-3' | 46 |

For each LVV, BTK expression levels were measured in HSCs of several healthy donors. LVV candidates that show high expression levels in CD34+ cells were selected for further characterization. In addition, the ratio of transgene derived BTK (trBTK) expression to endogenous BTK (enBTK) expression will be measured and used for selection of optimal LVV candidates. To measure BTK levels in different cell types, human BTK ELISA Kit was used (Abcam). Fifty (50) μl of cell lysate diluted in extraction buffer and 5 μl of antibody cocktail were added to a pre-coated 96-well ELISA plate and were incubated for 1 hour. Plates were washed 3 times with 1× PT wash buffer and TMB development solution were added for 10 min, Reaction was stopped, and OD was read at 450 nm using ELISA plate reader. BTK levels were quantified by comparison with titrated BTK standards.

The inventors tested several codon optimized BTK coding sequences having the sequences set forth in SEQ ID Nos: 9-12. SEQ ID NO: 13 (when including further features as part of an expression vector, is referred to herein as NTX112; SEQ ID NO: 26) is a codon optimized BTK ORF disclosed in international patent application No. PCT/US2018/028331. SEQ ID NO: 12 is a codon optimized BTK with high homology to the wt BTK sequence (90.9% homology). For comparison, homology of wt BTK to SEQ ID NO: 9 is 77.7% and for SEQ ID NO: 13 is 78.5%. These sequences were cloned under control of the 1,033 bp BTK promoter and the level of expression was compared to that of a construct with WT BTK coding sequence (SEQ ID NO: 8). To compare between WT BTK coding sequence and the different codon optimized expression cassettes, human CD34+ cells were transduced with the different BTK LVVs at MOI100. Five days post transduction, GFP mRNA levels were compared using real time qPCR and BTK and GFP protein levels were measured using flow cytometry (FIGS. 1A-1D). NTX143, under the 1,033 bp BTK promoter was compared to NTX109 in human CD34+ cells at MOI of 25. Six days post transduction, GFP and Btk protein levels were compared using flow cytometry and ELISA respectively (FIGS. 2A-2C).

SEQ ID NO: 23, also referred to herein as NTX109 showed higher BTK levels than SEQ ID NO: 22 across all tested subjects (two human donors). Relative VCN for this study showed a 1-2-fold difference between the various constructs. These results suggest that NTX109 may be suitable for use as an expression cassette for XLA gene therapy.

To this end, it is generally acceptable that minimal promoters of 200-300 bp are sufficient to induce gene transcription. Further, others have previously reported that a 798 bp long BTK promoter was required for expression of the BTK gene, which is the longest recombinant BTK promoter reported thus far.

With this respect, the inventors have designed and examined a set of LVVs that included four minimal BTK promoters having the sequences set forth in SEQ ID Nos: 1-4 and the BTK coding sequence having the sequence set forth in SEQ ID NO: 8. To characterize expression level derived from the minimal BTK promoter expression cassette, human CD34 cells were transduced with the different LV_NTX at MOI100. Relative VCN was determined using real time qPCR and showed a 1-2-fold difference between the various constructs. Six (6) days post transduction GFP protein levels were measured using flow cytometry (FIG. 3). SEQ ID NO: 22, also referred to herein as NTX101 showed higher BTK levels than SEQ ID Nos: 19-21 in two human healthy donors. To expand the characterization of the BTK promoter, the 1,033 bp promoter was further compared to other BTK promoters of various lengths SEQ ID Nos: 5-7. Promoter designs include a long version of the BTK promoter (1,533 bp), a mid-size version of 798 bp as was used in the disclosed international patent application No. PCT/US2018/028331 and a synthetic promoter in which internal 409 bp were removed. In this described case, expression derived from the codon optimized BTK transgene was measured (NTX 132-NTX134). Integration events measured for these constructs were between 0.4 to 1 VCN per cell. Similarly, to previous results, expression levels derived from the 1,033 bp promoter length were higher in comparison to the other tested promoters in the two healthy human donors tested (FIG. 4).

These results suggest that the 1,033 bp of the promoter of SEQ ID NO: 4 surpasses SEQ ID Nos.: 1-3, and 5-7 as an optimal BTK promoter with respect to BTK expression levels.

Therefore, the inventors have shown that in contrast to the state of the art at the time of filing, a longer version of the BTK promoter, e.g., 1,033 bp long, is required so as to control the expression of a codon optimized BTK construct (as exemplified herein using NTX109; SEQ ID NO: 23), as disclosed herein, in a manner that provides 2-3 fold greater expression levels compared to the endogenous BTK expression level. This 2-3 fold increase in expression was further found to be optimal for therapeutic purposes. To this end, such increased BTK expression levels are unprecedented, and were not previously reported when the endogenous promoter was employed.

To test the regulatory effect of the BTK 5'UTR on BTK expression, the inventors have compared the full length (total of 160 bp) to a dissected version of the BTK 5'UTR that includes only 31 bp. As a reference, in international patent application No. PCT/US2018/028331, the length of the 5'UTR used was 41 bp. Also, a modified 5'UTR with altered thermodynamic characteristics was included. This version contained 14 mismatch mutations in comparison to the wt 5'UTR and was designed based on the RNAfold thermodynamic ensemble predictor (http://rna.tbi.univie.a- c.at/cgi-bin/RNAWebSuite/RNAfold.cgi). All constructs contained the 1,033 bp BTK promoter and the GFP and codon optimized BTK transgenes separated by T2A. Six (6) days post transduction into CD34 cells, GFP protein levels and mRNA transcript levels were measured (FIG. 5). Expression derived from NTX137 which contain the short 5'UTR version, was lower than NTX109 (0.7-fold in protein levels and 0.4-fold in transcript levels). Significant decrease in expression was measured when the 5'UTR was modified with missense mutations (0.19-fold in protein levels and 0.06-fold in transcript levels in comparison to NTX109). Integration events for NTX109, NTX137 and NTX142 were measured 15 days post transduction and corresponded to 1, 0.5 and 0.1 VCN/cell, respectively. This study demonstrates the importance of inclusion of the full length BTK 5'UTR for maintaining BTK expression levels and regulation.

Lastly, the inventors have compared SEQ ID NO: 23, also referred to herein as NTX109 to the expression cassette disclosed in international patent application No. PCT/US2018/028331 SEQ ID NO: 31, also referred to herein as NTX141. Six (6) days post transduction into CD34 cells, GFP protein levels were measured at a range of MOI (5-50) (FIGS. 6A-6C). At MOI of 25, expression derived from NTX141 was lower than NTX109 (0.6-fold in percentage of positive GFP levels and 0.23-fold in mean fluorescence intensity). Integration events for NTX109 and NTX141 were measured 13 days post transduction and corresponded to an average of 2.6 and 1.15 respectively.

Example 2

Dose Response Test of NTX109 in Human HSCs

From a safety perspective, it is important to define the minimal number of transduced virions required for therapeutic effect. In this study, the inventors transduced human CD34+ cells with NTX109 at reducing MOIs of, 100, 50, 25, 12.5 and 5. VCN/cell measured in this study showed consistency with the dose response design and was between 0.3±0.15 for the lowest dose (MOI5) reaching up to 1.5±0.16 for the highest dose (MOI100) (FIG. 7B). Six (6) days post transduction GFP and Btk transgene protein levels were measured using flow cytometry and ELISA (FIGS. 7A, 7C and 7D). These results demonstrated that at MOI of 25, CD34+ cells transduced with NTX109 have reached near saturation levels in both number of positive transgene cells and the amount of total BTK.

Example 3

Selection Based on BTK Function Restoration in BTK Deficient Cells Derived from X-Linked Immune Deficient (Xid) Mice LVV candidates can be tested for Btk function restoration using several assays. For example, B-cell receptor stimulation is evaluated by restoration of B-cell development and maturation in-vitro, B-cell proliferation in culture, measurement of $Ca^{2+}$ flux, as well as phosphorylation of downstream effectors.

In addition, further selection is done by testing Btk expression and function in Btk deficient cells. Lineage negative HSPCs (Lin−) derived from the bone marrow of murine X-linked immunodeficiency (Xid; CBA/CaHN-Btk xid/J, Jackson Laboratories) were selected for these studies.

Xid mice have a spontaneous missense mutation in the PH domain. The mutant protein is inefficiently recruited to the plasma membrane and fails to enter the BCR signalosome. The phenotype of both Xid and $BTK^{-/-}$ mice is less severe than that of XLA, presumably due to a redundancy of other Tec kinases. Xid mice are unable to mount an antibody response to thymus-independent type II antigens, although they do produce normal amounts of antibody in response to some protein antigens. They have low serum IgM and IgG3 and a reduced number of B-cells. Moreover, the B-cells that are present have a reduced surface IgM to IgD ratio, which suggests a disorder in B-cell maturation. BTK-deficient transitional 2 (T2) immature B cells fail to generate the BCR-dependent pro-survival, proliferative, and differentiation signals required to produce mature B cells. Consistent with these findings, the BCR-dependent calcium signal is markedly reduced in BTK-deficient B cells (Ng et al. 2010; Yu et al. 2004).

To screen for LVV candidates, which restore both the expression and function of Btk in Xid Lin− cells, LVV transduced cells are cultured in conditions which support B cell differentiation. Immunophenotyping analysis of B cell subtype development is done by flow cytometry. To demonstrate B cell activity of these cells, differentiated B cells are stimulated in vitro with lipopolysaccharide (LPS) for 3-4 days and secretion of IgM antibody to the medium is detected using enzyme-linked immunosorbent assay (ELISA). These cell assays provide means for further valuation of LVV candidates as they enable to accurately measure Btk function and B cells differentiation competency, as these outcomes necessarily result from gene modified cells.

BTK LVV candidates NTX101 and NTX109 were assayed as described above for their capacity to correct the B-cell development defect in Xid Lin− cells in vitro. Both NTX101 and NTX109 drive GFP expression in Xid Lin− cells as shown in FIGS. 8A-8B, with NTX109 expressed in a higher percentage of cells and with higher mean fluorescence intensity (MFI). Furthermore, as shown in FIG. 8C, both NTX101 and NTX109 improved the rate of in-vitro differentiation of Xid Lin− cells to B-cells, bringing the percentage of B-cells from 5.2% in un-transduced Xid to 28.4% in $Xid^{NTX101}$ and 42.6% in $Xid^{NTX109}$. Moreover, as shown in FIG. 8D, IgM positive cells were elevated in $Xid^{NTX101}$ and $Xid^{NTX109}$ transduced cells from 2.2% in un-transduced cells to 19.8% and 25.6% respectively, providing further demonstration of the capacity of NTX109 to correct the B-cell differentiation deficiency of Xid mice.

Example 4

Potency Test for Optimized LV_NTX Vectors Based on Function Restoration of BTK Activity in Murine Xid Model In-Vivo The Xid mouse model was used to assess the in-vivo capacity of the herein disclosed lead LVV candidate NTX109 to restore BTK function. Importantly, this study facilitated measurement of the efficacy and specificity of the transduced LVV. NTX109 was transduced ex-vivo to HSPCs (Lin−) derived from the bone marrow of a cohort of Xid donor mice. The Transduced cells were transplanted to a second cohort of lethally irradiated Xid recipient mice.

To test the function of NTX109 in Xid mice in-vivo, $Xid^{NTX109}$Lin− cells were transplanted to eight lethally irradiated Xid mice. The study was terminated 14 weeks following transplantation and cells isolates from blood, BM and spleen were collected from each transplanted mouse and control animals (FIG. 9A). For negative control, Xid mice were transplanted with Xid cells transduced with a BTK-less LVV. CBA/Ca naïve mice served as a positive control. Reconstitution of the hematopoietic lineages (B, T and Myeloid) was assessed as well as expression of the Btk transgene in these lineages. VCN/cell was measured ex vivo 6 days post transduction and was found to be 1.17±0.2. At time of termination, VCN/cell in the bone marrow exhibited a moderate increase reaching to 2.3±0.5 VCN/cell (FIG. 9B). This clinically relevant VCN value demonstrate the safety of the therapy.

Btk transgene expression is presented by percentage of GFP expressing cells, as can be seen in FIGS. 9C and 9D, GFP expression was detected in the BM and spleen at 15 weeks post transplantation. Specificity of NTX109 expression pattern aligned with the endogenous Btk expression pattern as was determined based on the high GFP levels measured in Myeloid and B cells, while T cells had very low percentage of GFP positive cells. T cells expressing GFP to B cells expressing GFP ratio (TB GFP+) was found to be 0.1 in the spleen. This low value indicates that NTX109 physiologically regulates BTK expression in Xid mice (FIGS. 9C-9E).

As published previously, the Xid splenic B cells show a block in B cell maturation, with a significant reduction in mature B cells and an increase in transitional stage cells (T2). Therefore, restoration of B cell functionality was tested by comparing the ratio between Pro and Pre B cells as well as immature and mature B cells. Indeed, NTX109 has the capacity to rescue this phenotype, as transplantation of $Xid^{NTX109}$ Lin– cells removed the blockade of the T2 stage and shifted the B cell population towards the mature state (FIGS. 9F-9G).

Ultimately, to test for antibody secretion, splenocytes were isolated 14 weeks post transduction and stimulated in vitro using lipopolysaccharide (LPS). IgM levels were measured pre and post stimulation (FIG. 10A) To measure total IgM levels in serum, MABTECH IgM ELISA Kit was used. 96-well ELISA plates (Danyel Biotech) were coated with 100 μl of capture anti-mouse IgM and diluted to a concentration of 2 μg/ml in PBS. Plates were incubated over night at 4° C. Next, ELISA plates were blocked for 1 hr in PBS containing 0.05% Tween 20 plus 0.1% BSA (Incubation buffer) at RT and washed 5 times in PBS with 0.05% Tween (wash buffer). Serum was added to a fresh incubation buffer and incubated for 2 hrs at RT. The plates were washed, and detection biotinylated antibody was added, followed by streptavidin HRP diluted 1:1,000 in incubation buffer. After 1 hour of incubation at RT, plates were washed and TMB substrate was added (Mabtech). The reaction was stopped by the addition of 0.2 M $H_2SO_4$, and the OD was read at 450 nm using ELISA plate reader. IgM levels were quantified by comparison with titrated IgM standards. Antibody secretion activity post transplantation of $Xid^{NTX109}$ Lin– cells in response to LPS stimulation was partially rescued at the whole organ level (FIGS. 10B-10C). This partial rescue in the Xid animals aligned with previous publications where's the Xid mice served to model XLA. This partial rescue could be explained by the fact that in contrast to XLA patients, Xid mice exhibit nearly normal early B cell development, therefore lacking the early B cell selective advantage. From that reason it is important to test for antibody secretion at the cellular level. For this calculation only NTX109 responding B cell (67% of cells) were taken into consideration and demonstrated significantly higher antibody secretion activity than $Xid^{mock}$ treated animals and comparable secretion to wt (FIG. 10D). Based on these measurements, the inventors concluded that NTX109 has the potential to reach the therapeutic window and to be used as a therapy for XLA patients.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A polynucleotide comprising:
   a) a first nucleic acid molecule comprising a sequence of between 799 to 1,533 nucleotides of a human endogenous Bruton's tyrosine kinase (BTK) promoter; and
   b) a second nucleic acid molecule comprising a codon optimized sequence encoding a BTK or a functional analog thereof, wherein said first nucleic acid molecule and said second nucleic acid molecule are operably linked, and wherein said codon optimized sequence is for BTK expression in a human subject, cell derived therefrom, or both, and wherein said polynucleotide comprises the nucleic acid sequence set forth in SEQ ID NO: 23.

2. An expression vector comprising the polynucleotide of claim 1.

3. The expression vector of claim 2, being a lentivirus-based expression vector.

4. A hematopoietic stem cell comprising the polynucleotide of claim 1.

5. A composition comprising the hematopoietic stem cell of claim 4, and a pharmaceutically acceptable carrier.

6. A method for enhancing B cell viability or activity in a human subject that is afflicted with X-linked agammaglobulinemia (XLA), the method comprising a step of transplanting an autologous hematopoietic stem cell transduced with the expression vector of claim 2 ex vivo to said subject.

7. The method of claim 6, wherein said viability or activity comprises: survival, proliferation, differentiation, or any combination thereof.

* * * * *